United States Patent
Roy

(10) Patent No.: US 11,185,824 B2
(45) Date of Patent: Nov. 30, 2021

(54) HEMOFILTRATION DEVICE AND METHODS OF USE THEREOF

(71) Applicant: The Regents of the University of California, Oakland, CA (US)

(72) Inventor: Shuvo Roy, San Ramon, CA (US)

(*) Notice: Subject to any disclaimer, the term of this patent is extended or adjusted under 35 U.S.C. 154(b) by 120 days.

(21) Appl. No.: 16/098,708

(22) PCT Filed: May 2, 2017

(86) PCT No.: PCT/US2017/030597
§ 371 (c)(1),
(2) Date: Nov. 2, 2018

(87) PCT Pub. No.: WO2017/192556
PCT Pub. Date: Nov. 9, 2017

(65) Prior Publication Data
US 2019/0134568 A1    May 9, 2019

Related U.S. Application Data

(60) Provisional application No. 62/350,553, filed on Jun. 15, 2016, provisional application No. 62/332,333, filed on May 5, 2016.

(51) Int. Cl.
*B01D 63/08* (2006.01)
*A61M 1/36* (2006.01)
(Continued)

(52) U.S. Cl.
CPC ......... *B01D 63/085* (2013.01); *A61M 1/1631* (2014.02); *A61M 1/3655* (2013.01);
(Continued)

(58) Field of Classification Search
CPC .. B01D 63/085; B01D 63/084; B01D 61/243; B01D 61/28; B01D 71/02;
(Continued)

(56) References Cited

U.S. PATENT DOCUMENTS 3,485,902 A * 12/1969 Critchell ............... B01D 61/28
156/70
4,038,192 A   7/1977 Serur
(Continued)

FOREIGN PATENT DOCUMENTS

DE    10017690    10/2001

OTHER PUBLICATIONS

Kim et al. (2016) "Preliminary Diffusive Clearance of Silicon Nanopore Membranes in a Parallel Plate Configuration for Renal Replacement Therapy" published as ASAIO J 62(2): 169-175, 16 pages.

*Primary Examiner* — Liam Royce
(74) *Attorney, Agent, or Firm* — Edward J. Baba; Shweta Chandra; Bozicevic, Field & Francis LLP

(57) ABSTRACT

Parallel plate devices for hemofiltration or hemodialysis are provided. A parallel plate device includes a parallel plate assembly having an aligned stack of stackable plate subunits, each stackable plate subunit having a through channel for blood, where the blood channels are opened up at opposite ends of the parallel plate assembly. The parallel plate assembly is configured to form filtrate/dialysate channels interleaved with the blood channels, adjacent channels being separated by a silicon nanoporous filtration membrane. A blood conduit adaptor is attached to the parallel plate assembly at each of the ends, and is configured to distribute blood to or collect blood from the blood channels. Also provided are systems and methods for using the parallel plate devices.

26 Claims, 44 Drawing Sheets

(51) Int. Cl.
    *B01D 61/24* (2006.01)
    *B01D 61/28* (2006.01)
    *B01D 71/02* (2006.01)
    *A61M 1/16* (2006.01)

(52) U.S. Cl.
    CPC ........... *B01D 61/243* (2013.01); *B01D 61/28* (2013.01); *B01D 63/084* (2013.01); *B01D 71/02* (2013.01); *A61M 2205/04* (2013.01); *A61M 2205/75* (2013.01); *A61M 2207/00* (2013.01); *B01D 2325/04* (2013.01)

(58) Field of Classification Search
    CPC ............ B01D 2325/04; A61M 1/3655; A61M 1/1631; A61M 2205/04; A61M 2205/75; A61M 2207/00
    See application file for complete search history.

(56) References Cited

U.S. PATENT DOCUMENTS

| | | | |
|---|---|---|---|
| 7,048,856 B2 | 5/2006 | Fissell, IV et al. | |
| 2005/0131332 A1* | 6/2005 | Kelly | A61M 1/1633 604/4.01 |
| 2009/0131858 A1 | 5/2009 | Fissell et al. | |
| 2010/0326914 A1 | 12/2010 | Drost et al. | |
| 2012/0152747 A1* | 6/2012 | Eisaman | B01D 63/085 204/631 |
| 2012/0289881 A1 | 11/2012 | Lyu et al. | |
| 2013/0218070 A1 | 8/2013 | Burnett et al. | |
| 2014/0238235 A1 | 8/2014 | Liu et al. | |

\* cited by examiner

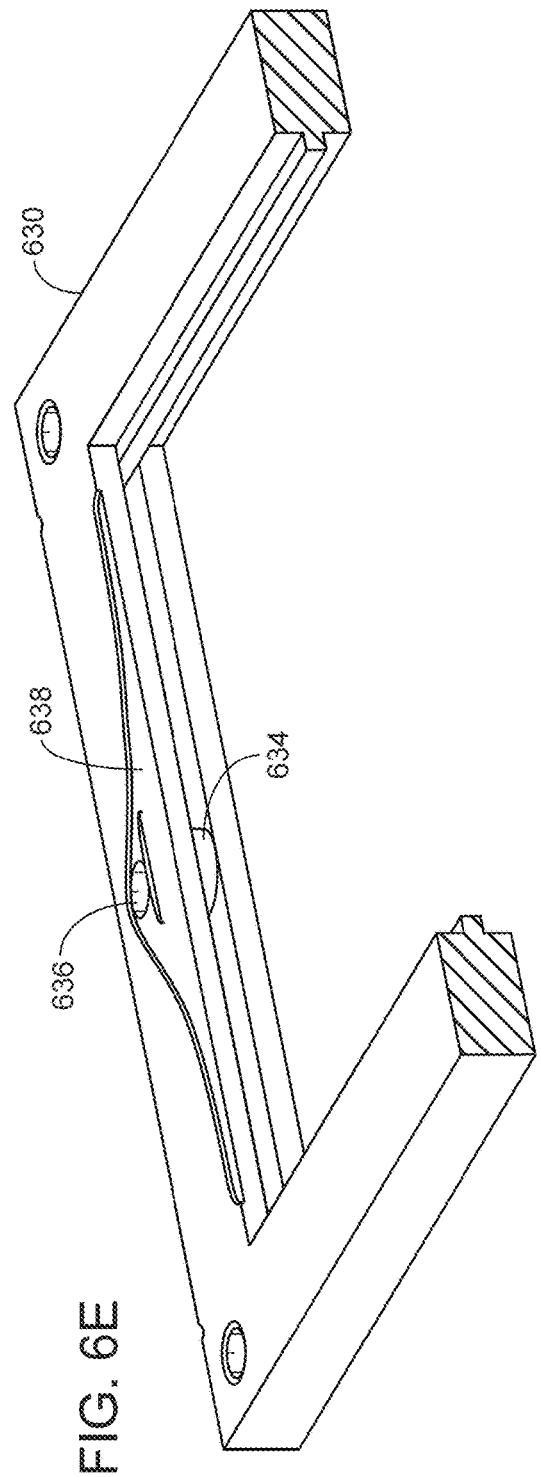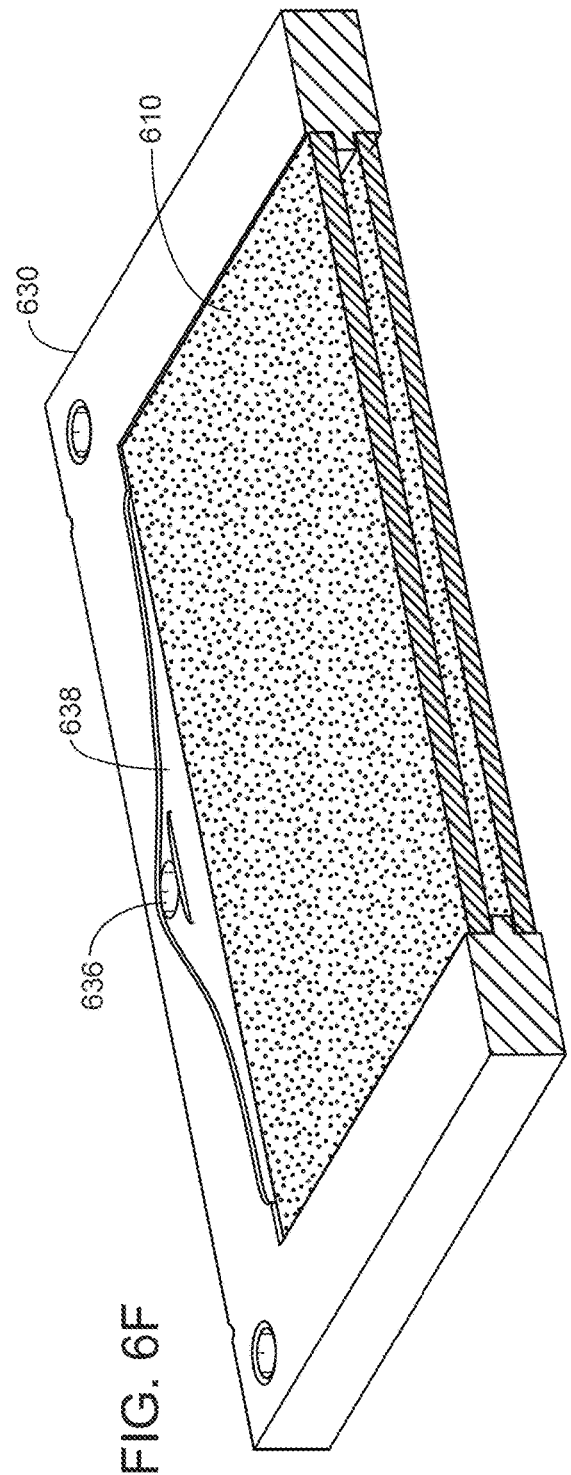

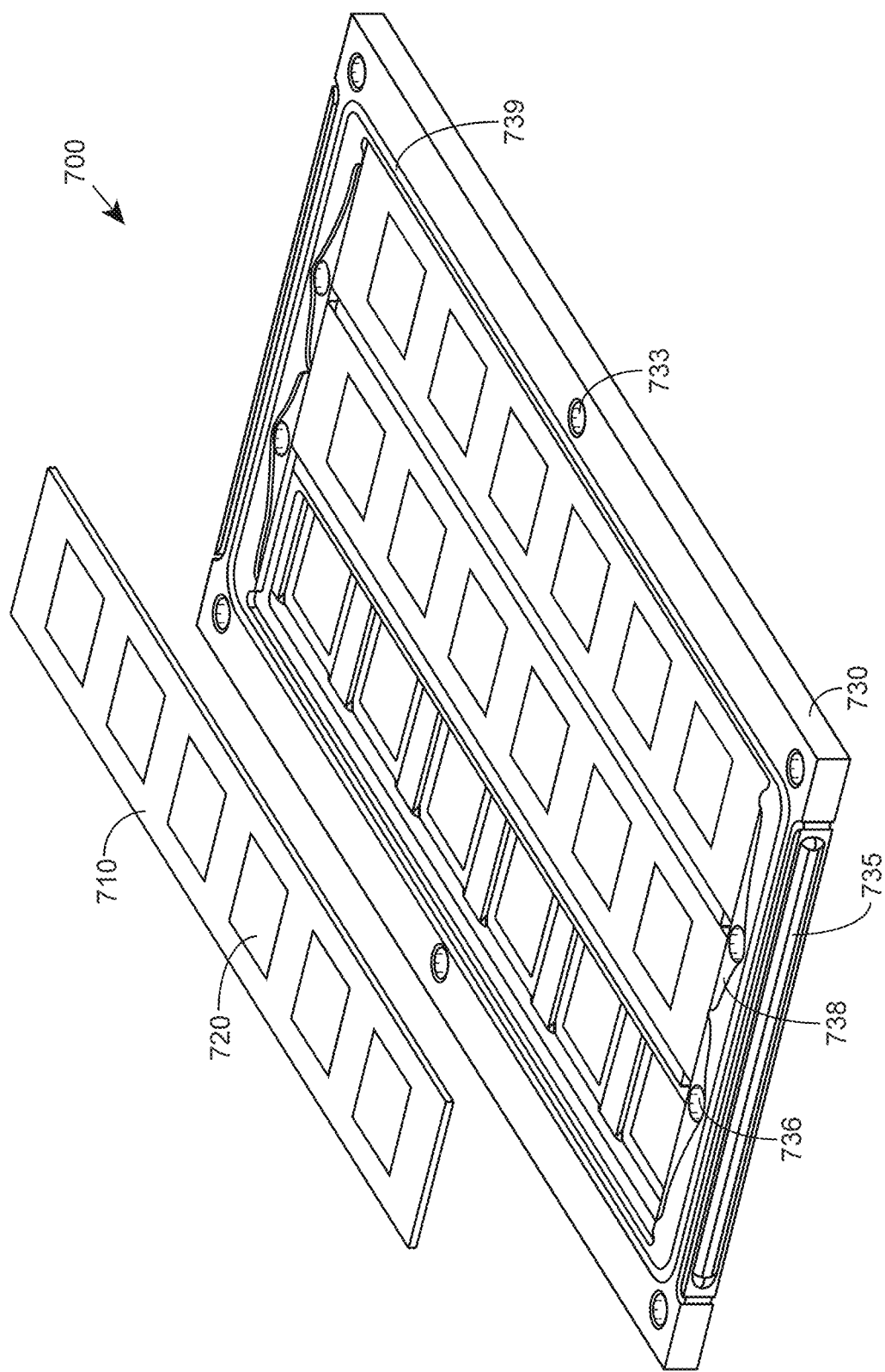

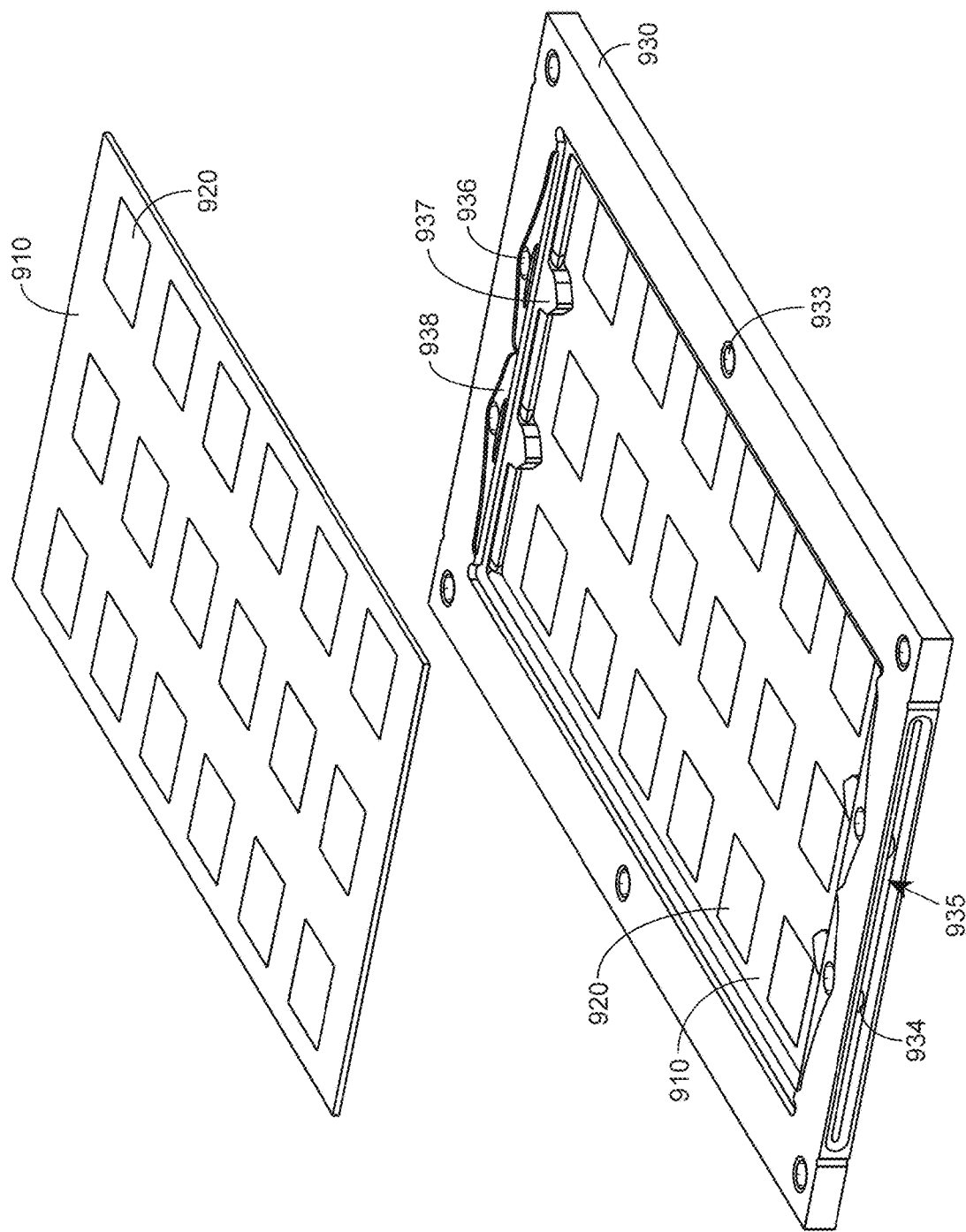

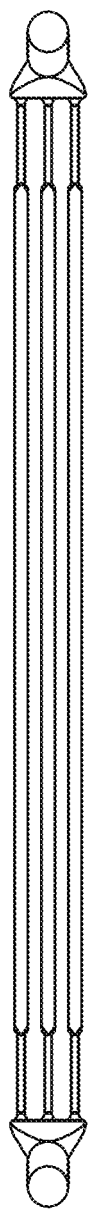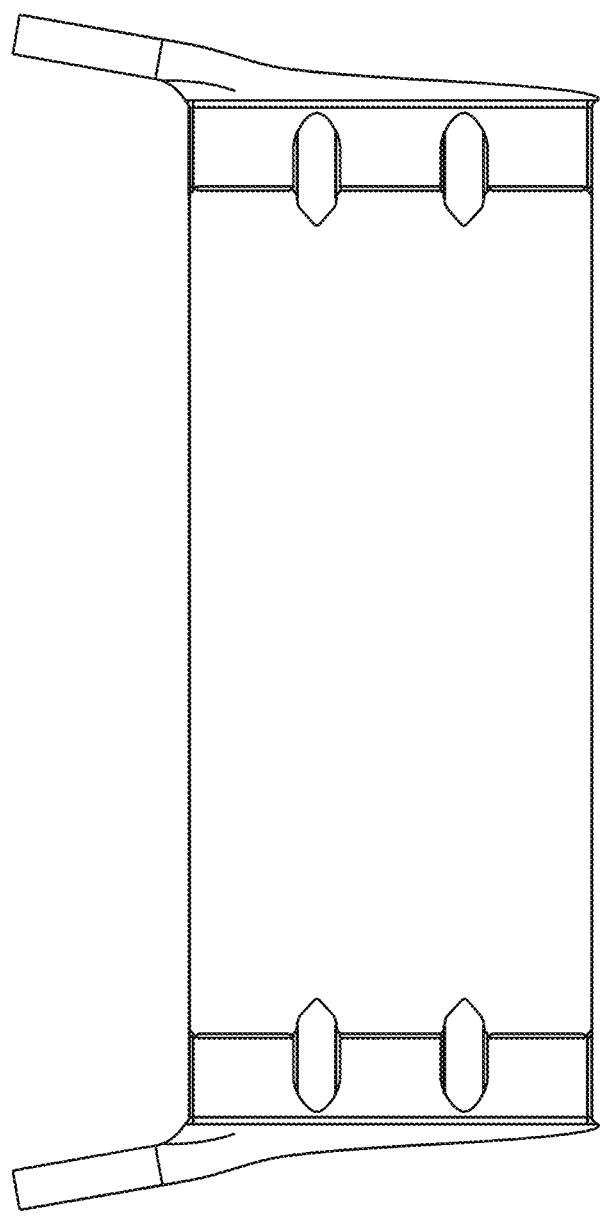
FIG. 11B
FIG. 11D
FIG. 11C

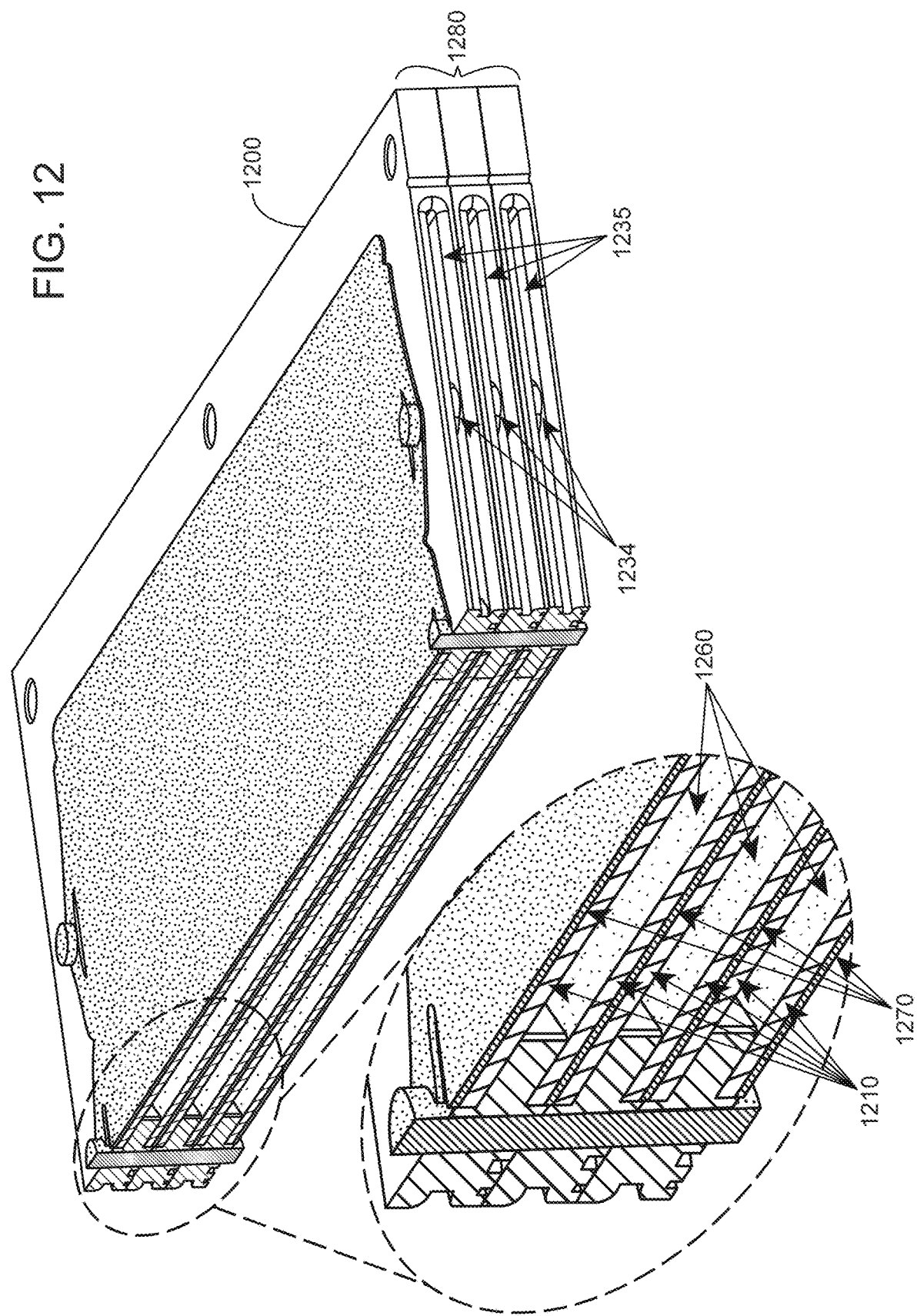

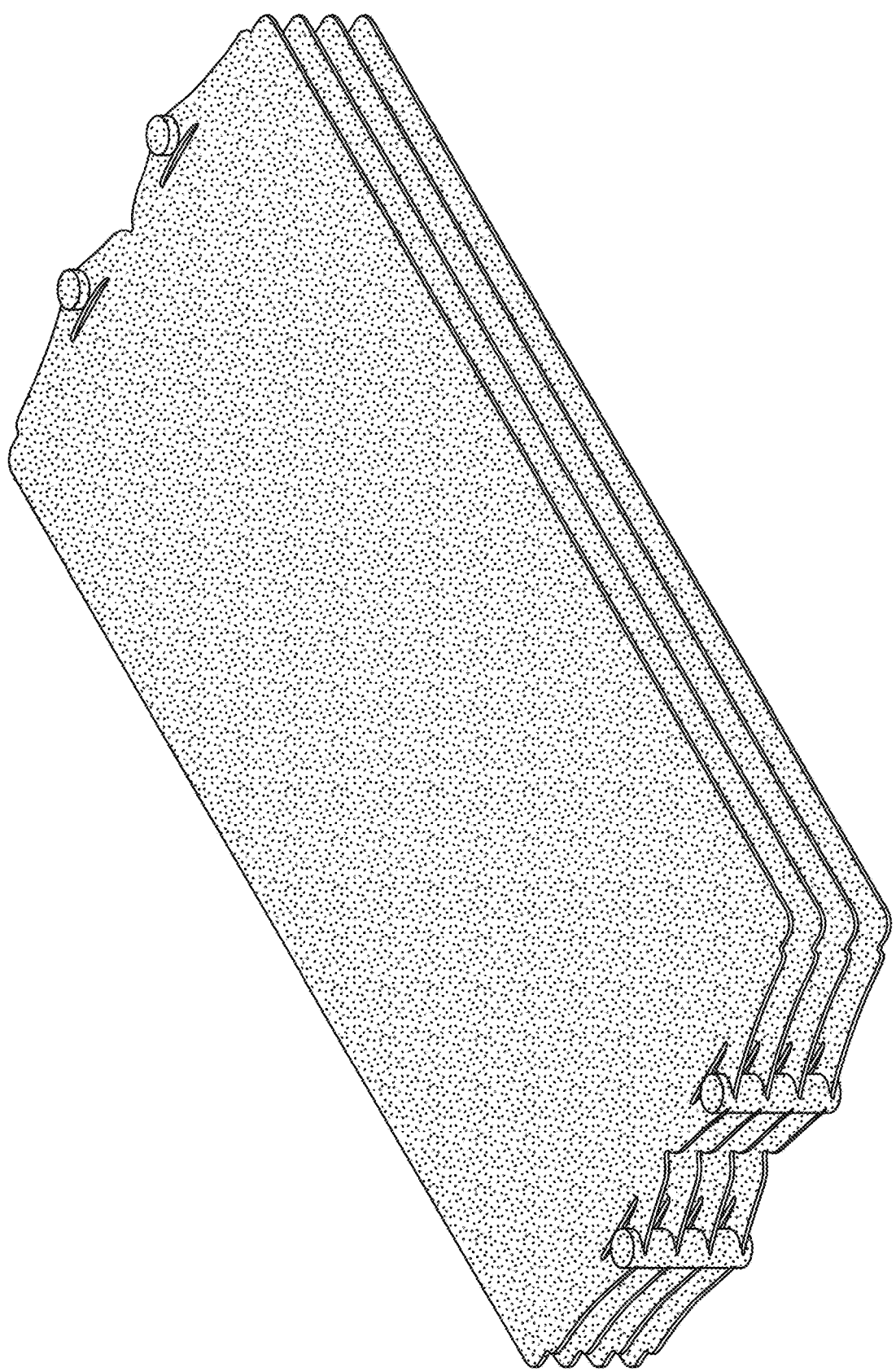

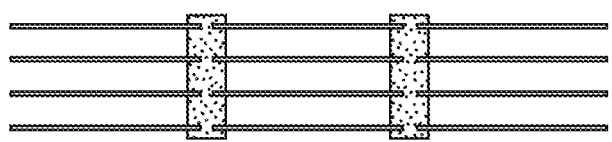
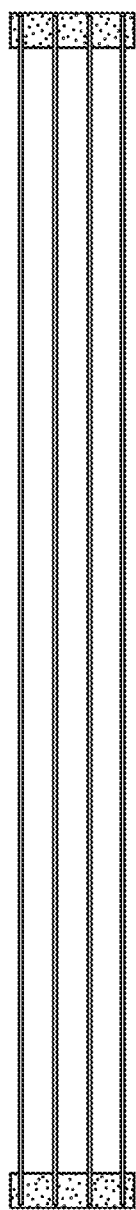
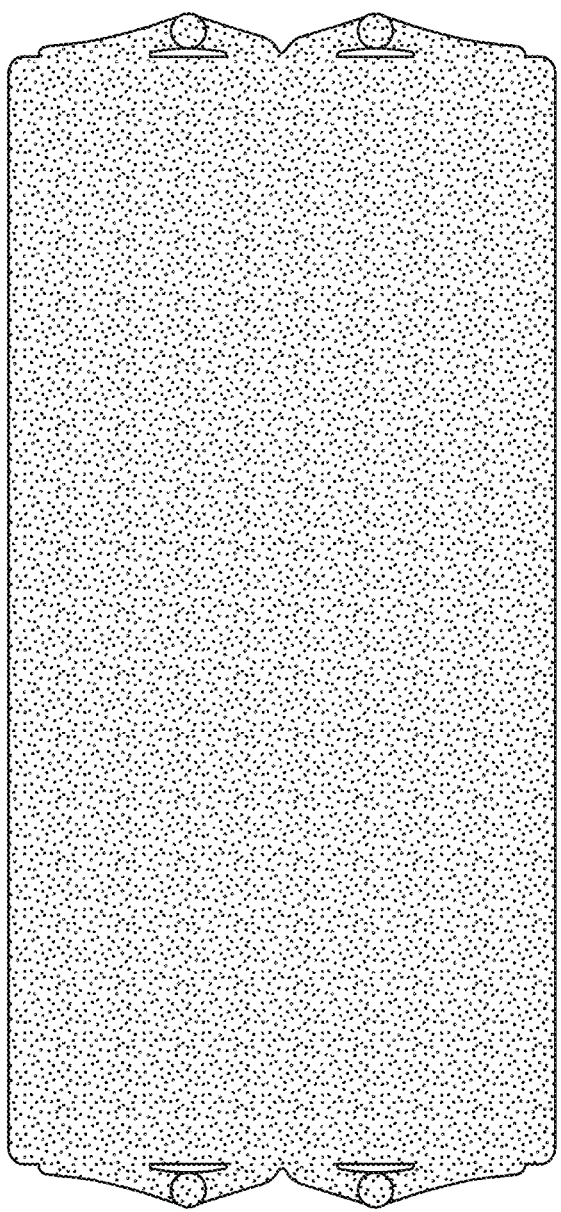

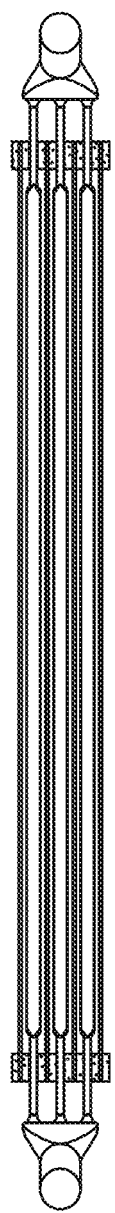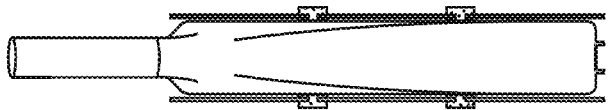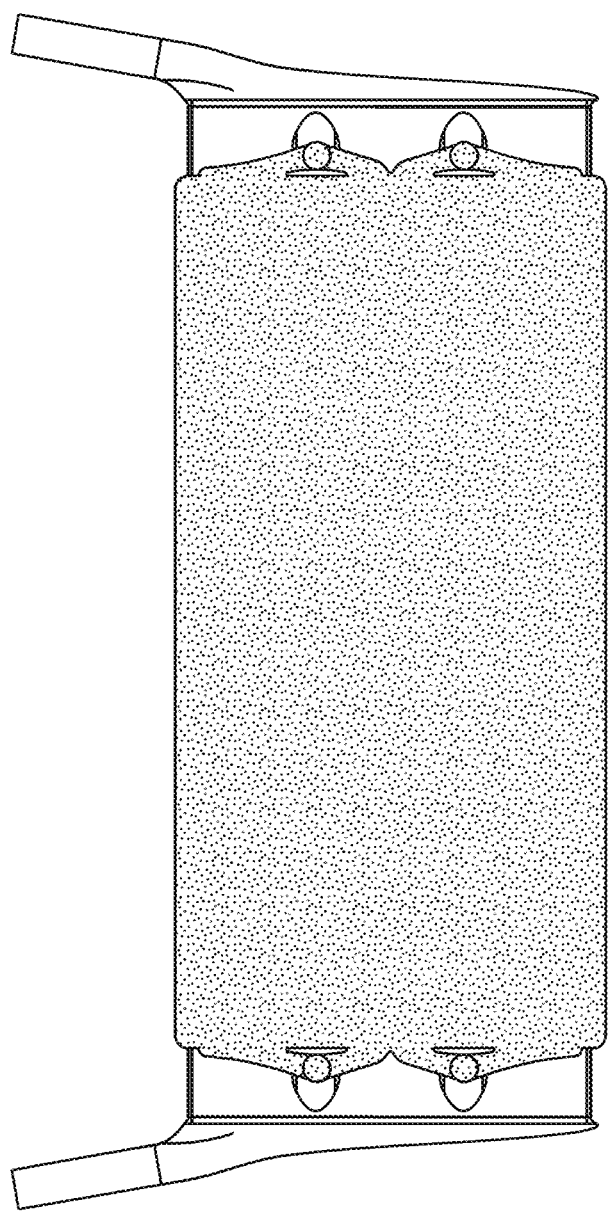

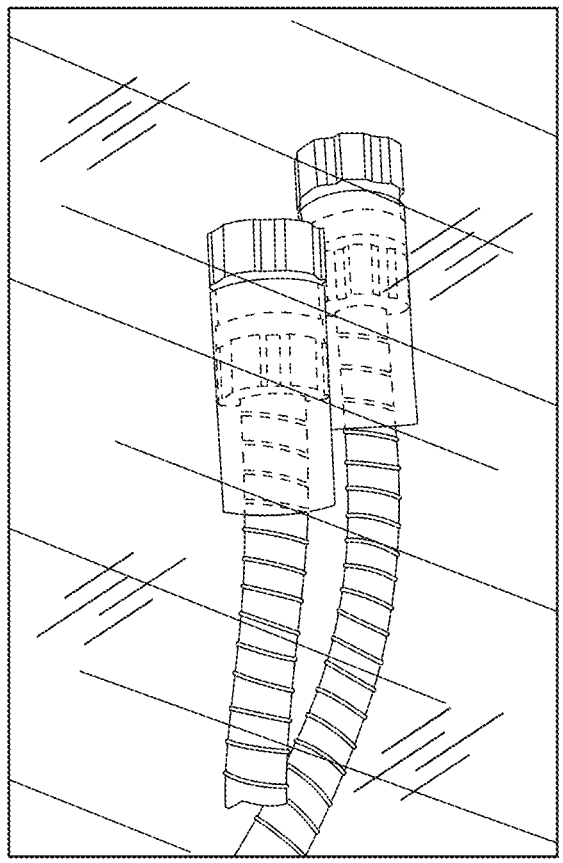
FIG. 26A
FIG. 26B
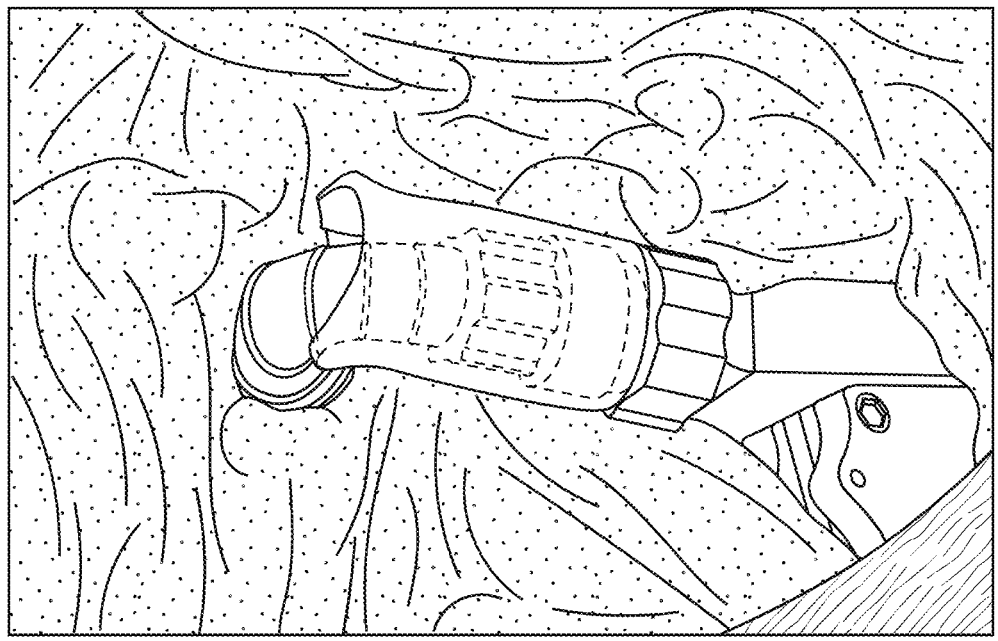

HEMOFILTRATION DEVICE AND METHODS OF USE THEREOF

CROSS-REFERENCE TO RELATED APPLICATIONS

This application claims priority to U.S. Provisional Application No. 62/332,333 filed May 5, 2016 and to U.S. Provisional Application No. 62/350,553 filed Jun. 15, 2016, which are both herein incorporated by reference in their entirety.

BACKGROUND

End Stage Renal Disease (ESRD) remains a major public health problem in the United States, afflicting over 615,000 people with nearly 116,000 new patients initiating treatment each year. Due to the shortfall in organ availability, the majority of ESRD patients in the United States undergo in-center, 3-4 hour, thrice weekly dialysis, such as hemodialysis or peritoneal dialysis.

Hemodialysis involves passing a patient's blood against a synthetic or semisynthetic membrane and inducing diffusive transport of toxins from the blood into a bath of dialysate on the other side of the membrane. In peritoneal dialysis, the patient's parietal peritoneal epithelium performs the function of the dialysis membrane.

SUMMARY

Parallel plate devices for hemofiltration or hemodialysis are provided. A parallel plate device includes a parallel plate assembly having an aligned stack of stackable plate subunits, each stackable plate subunit having a through channel for blood, where the blood channels are opened up at opposite ends of the parallel plate assembly. The parallel plate assembly is configured to form filtrate/dialysate channels interleaved with the blood channels, adjacent channels being separated by a silicon nanoporous filtration membrane. A blood conduit adaptor is attached to the parallel plate assembly at each of the ends, and is configured to distribute blood to or collect blood from the blood channels.

A stackable plate subunit of the present disclosure includes a planar through channel defined by two silicon nanoporous membranes positioned in a stackable frame such that the membranes are substantially parallel to each other and in a spaced apart configuration.

BRIEF DESCRIPTION OF THE FIGURES

The skilled artisan will understand that the drawings, described below, are for illustration purposes only. The drawings are not intended to limit the scope of the present teachings in any way.

FIGS. 6A-6F are schematic diagrams showing a plate subunit (FIGS. 6A-6C, 6E and 6F) and a parallel plate assembly (FIG. 6D) of a parallel plate device, according to embodiments of the present disclosure.

FIGS. 7A and 7B are a collection of drawings showing a plate subunit of a parallel plate device, according to embodiments of the present disclosure.

FIGS. 9A and 9B are a collection of drawings showing a plate subunit of a parallel plate device, according to embodiments of the present disclosure.

FIGS. 11A-11D are a collection of drawings showing the blood compartment of a parallel plate device, according to embodiments of the present disclosure.

FIG. 12 is a drawing showing the filtrate/dialysate compartment of a parallel plate device, according to embodiments of the present disclosure.

FIGS. 13A-13D are a collection of drawings showing the filtrate/dialysate compartment of a parallel plate device, according to embodiments of the present disclosure.

FIGS. 14A-14D are a collection of drawings showing the filtrate/dialysate compartment and the blood compartment of a parallel plate device, according to embodiments of the present disclosure.

FIGS. 26A and 26B are a collection of images showing silicone sleeve-reinforced vascular graft connectors, according to embodiments of the present disclosure.

DEFINITIONS

Figure 1:
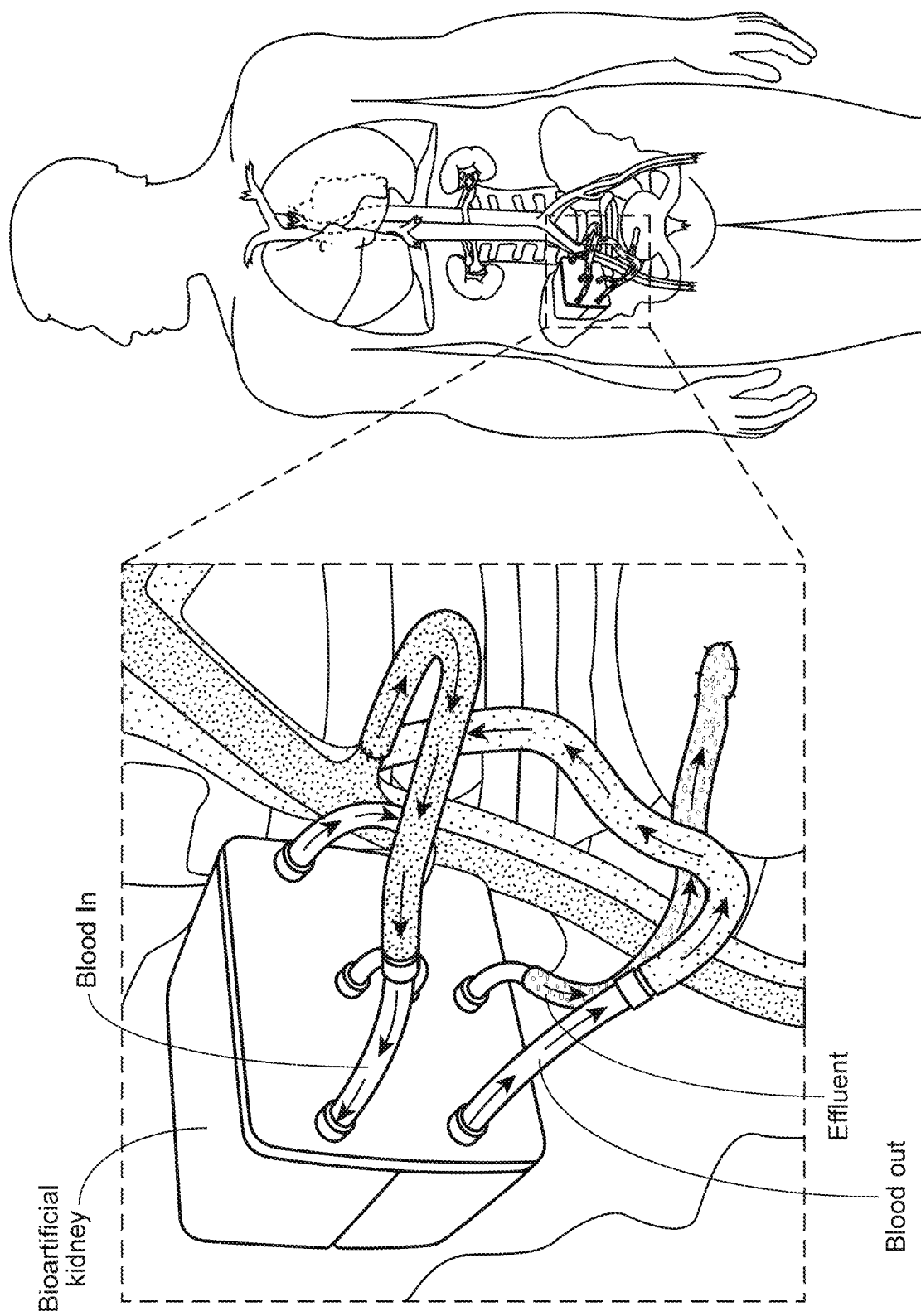
FIG. 1 is a schematic diagram showing an implantable bioartificial kidney, according to embodiments of the present disclosure.

The term "about" as used herein when referring to a measurable value such as a physical quantity, a temporal duration, and the like, is meant to encompass variations of ±20%, such as ±10%, such as ±5%, ±1%, including ±0.1% from the specified value, as such variations are typical of measurements characterizing the disclosed devices or appropriate to perform the disclosed methods.

As used herein "substantially", may be applied to modify any quantitative representation that could permissibly vary without resulting in a change in the basic function to which it is related. For example, two silicon nanoporous membranes may be somewhat non-parallel to each other if the stackable structure of the plate subunit, and the hydrodynamic and/or filtration properties of the silicon nanoporous membranes are not materially altered.

A "plurality" contains at least 2 members. In certain cases, a plurality may have at least 10, at least 100, at least 1000, at least 10,000, at least 100,000, at least $10^6$, at least $10^7$, at least $10^8$ or at least $10^9$ or more members.

As used herein, the term "individual" refers to any animal, such as a mammal like a dog, cat, livestock (e.g., pig), non-human primate, and including a human. The individual may be a patient with a compromised kidney function and/or in need of dialysis.

"Biocompatible," as used herein, refers to a property of a material that allows for prolonged contact with a tissue in a subject without causing toxicity or significant damage.

"Planar" as used herein, may be applied to describe a three dimensional shape of any object, where the length scale of two dimensions that are substantially perpendicular to each other (e.g., length and width) is longer than the length scale of a third dimension (e.g., thickness) that is substantially perpendicular to both of the other two dimensions. The length scale of one of the two longer dimensions may be similar to or different from the other longer dimension. The first two dimensions may define a plane.

"Through channel" or "through hole" is used herein to describe a channel or hole that connects one side of the structure in which the channel or hole is formed, to another side of the structure. The first side and the second side are generally opposite sides of the structure.

"Bound" as used herein, may be applied to describe a physical limit in the spatial extent.

"Latent" as used in reference to a device of the present disclosure, is meant to indicate a functional structure, such as a filtrate/dialysate channel, that emerges is not present in individual components of the device, typically with respect to "Interface" as used herein, may describe a boundary region between two different structures, where the structures are at least partly in direct physical contact with each other over a surface from each structure. The boundary region may include surfaces from each structure that face each other without any other intervening structures there between, but are not in direct physical contact. For stackable plates subunits that are stacked, the boundary region having physical contact between the stacked plates may include a stacking surface of each subunit.

"Nanopore" as used herein, refers to a pore that penetrates a substrate from one side to another, where the pore has at least one lateral dimension (e.g., width and/or length, but not the height/thickness of the pore across the substrate) that is in the nanometer range, e.g., in the range of 1.0 nm to 1,000 nm.

As used herein, the term "polysilicon" refers to a polycrystalline form of silicon that is deposited as a thin film. It is used in microelectronics for transistors and wiring. In MEMS, polysilicon is usually used as structural material for devices.

"Pumpless" as used in reference to a blood circuit is meant to refer to the absence of a pump mechanism other than the pump mechanism (e.g., the heart) that drives blood flow through the circulatory system of an individual.

As used herein, the term "filtration" refers to a process of separating particulate matter from a fluid, such as a liquid, by passing the fluid carrier through a medium that will not pass the particulates.

As used herein, the term "ultrafiltration" refers to subjecting a fluid to filtration, where the filtered material is very small; typically, the fluid includes colloidal, dissolved solutes or very fine solid materials, and the filter is a microporous, nanoporous, or a semi-permeable medium. A typical medium is a membrane. The fluid to be filtered is referred to as the "feed fluid." During ultrafiltration, the feed fluid is separated into a "permeate" or "filtrate" or "ultrafiltrate," which has been filtered through the medium, and a "retentate," which is that part of the feed fluid which did not get filtered through the medium, or which is retained by the medium.

As used herein, the term "dialysis" refers to a form of filtration, or a process of selective diffusion through a membrane; it is typically used to separate low-molecular weight solutes that diffuse through the membrane from the colloidal and high-molecular weight solutes which do not. In some embodiments, a feed of fluid is passed over a semi-permeable membrane, and a feed of dialysate is passed over the other side of that membrane; the membrane is wetted by one or both solvents, and then there is diffusive transport of dissolved solutes between the fluids. The composition of one fluid, the dialysate, may be used to deplete the composition of the other fluid, the feed fluid, of some molecule or molecules.

As used herein, the term "dialysate" is used to refer to the fluid into which low-molecular weight solutes diffuse through a membrane from another fluid (typically, the feed fluid) initially containing these solutes.

"Fluidic communication" as used herein, is meant to refer to accessibility of a body of fluid, e.g., an aqueous fluid (such as water, serum, blood, etc.) to different areas under normal operating conditions (e.g., physiological temperature and blood pressure, etc.).

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Where a range of values is provided, it is understood that each intervening value, to the tenth of the unit of the lower limit unless the context clearly dictates otherwise, between the upper and lower limit of that range and any other stated or intervening value in that stated range is encompassed within the present disclosure.

Certain ranges are presented herein with numerical values being preceded by the term "about." The term "about" is used herein to provide literal support for the exact number that it precedes, as well as a number that is near to or approximately the number that the term precedes.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

It must be noted that as used herein and in the appended claims, the singular forms "a," "an," and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

One with skill in the art will appreciate that the present invention is not limited in its application to the details of construction, the arrangements of components, category selections, weightings, pre-determined signal limits, or the steps set forth in the description or drawings herein. The invention is capable of other embodiments and of being practiced or being carried out in many different ways.

DETAILED DESCRIPTION

As summarized above, parallel plate devices for hemofiltration or hemodialysis, and stackable plate subunits for making the same are provided. The parallel plate devices provide planar filtrate/dialysate channels interleaved with planar through channels for blood, adjacent channels being separated by a silicon nanoporous filtration membrane. Filtration or dialysis of blood is achieved by diffusive transport of permeable components across the silicon nanoporous membrane. The planar flow of blood across the blood channels in the present device provides for a sufficiently low resistance such that a desirable blood flow rate is achieved by the blood pressure in the circulatory system of an individual. Thus, the present parallel plate devices may be a pumpless system for hemofiltration or hemodialysis.

Figure 5A:
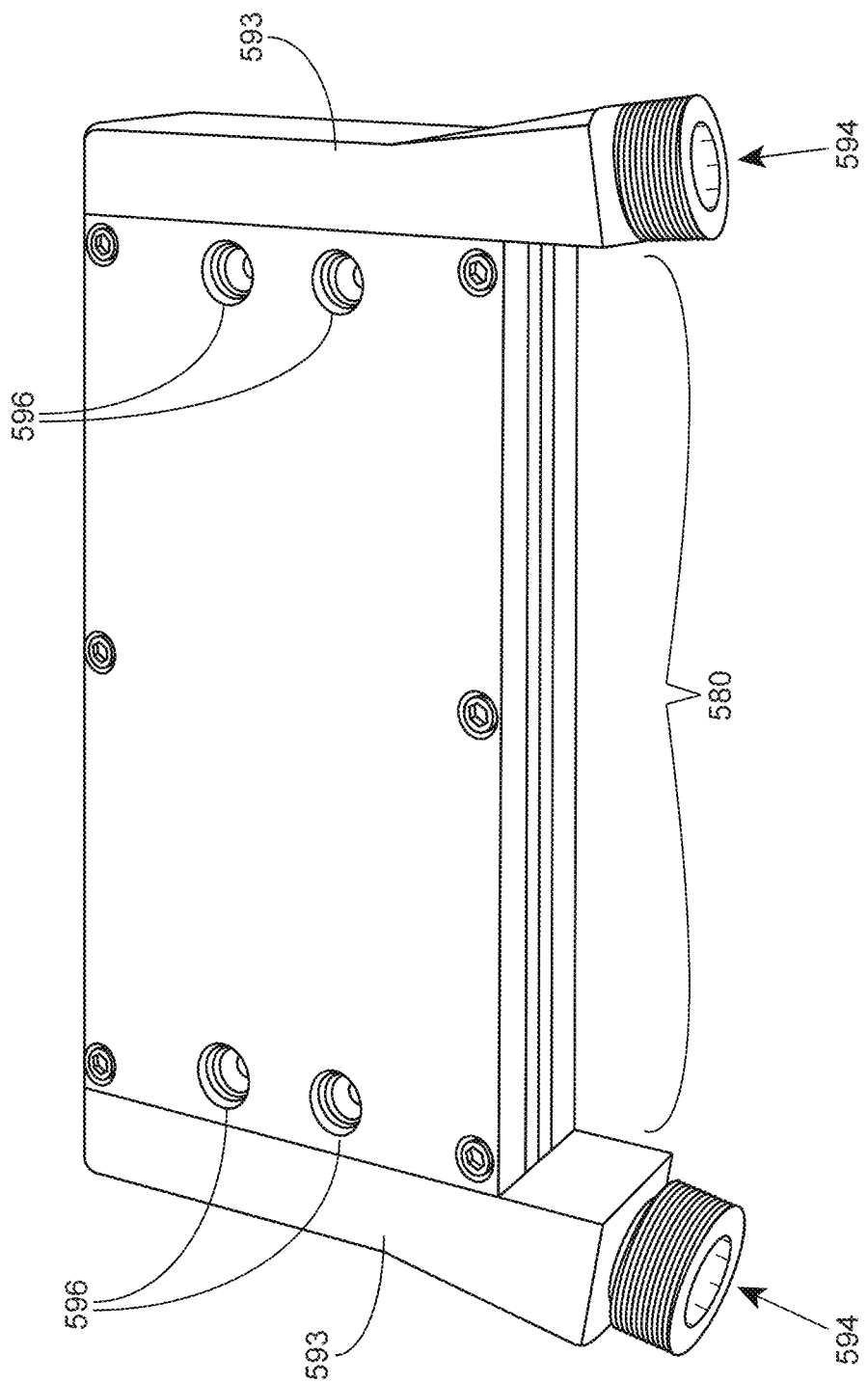
FIGS. 5A and 5B are a collection of drawings showing a parallel plate device, according to embodiments of the present disclosure.
Figure 5B:
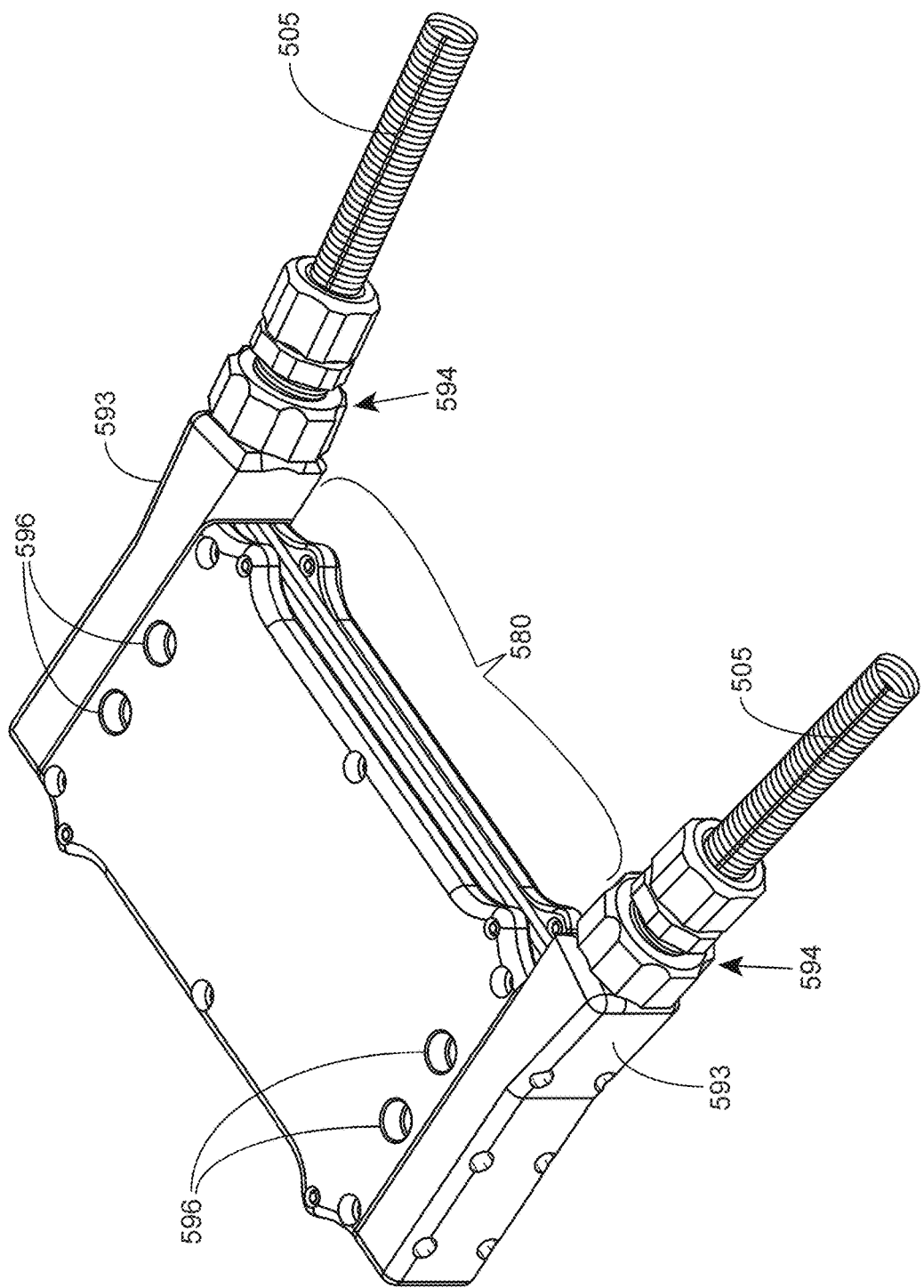
Figure 6A:
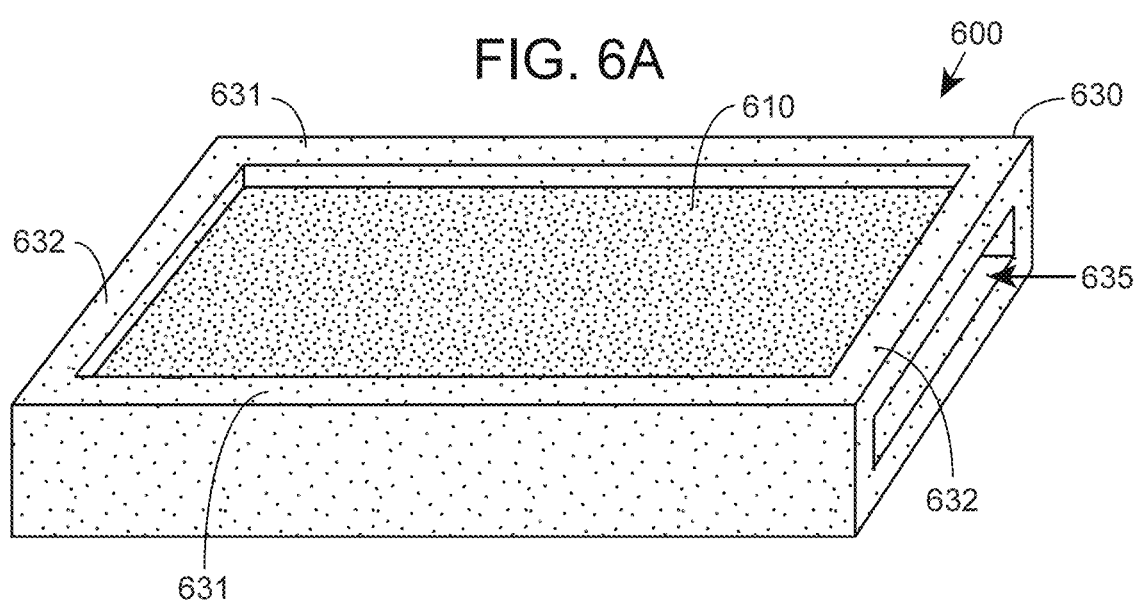
Figure 6B:
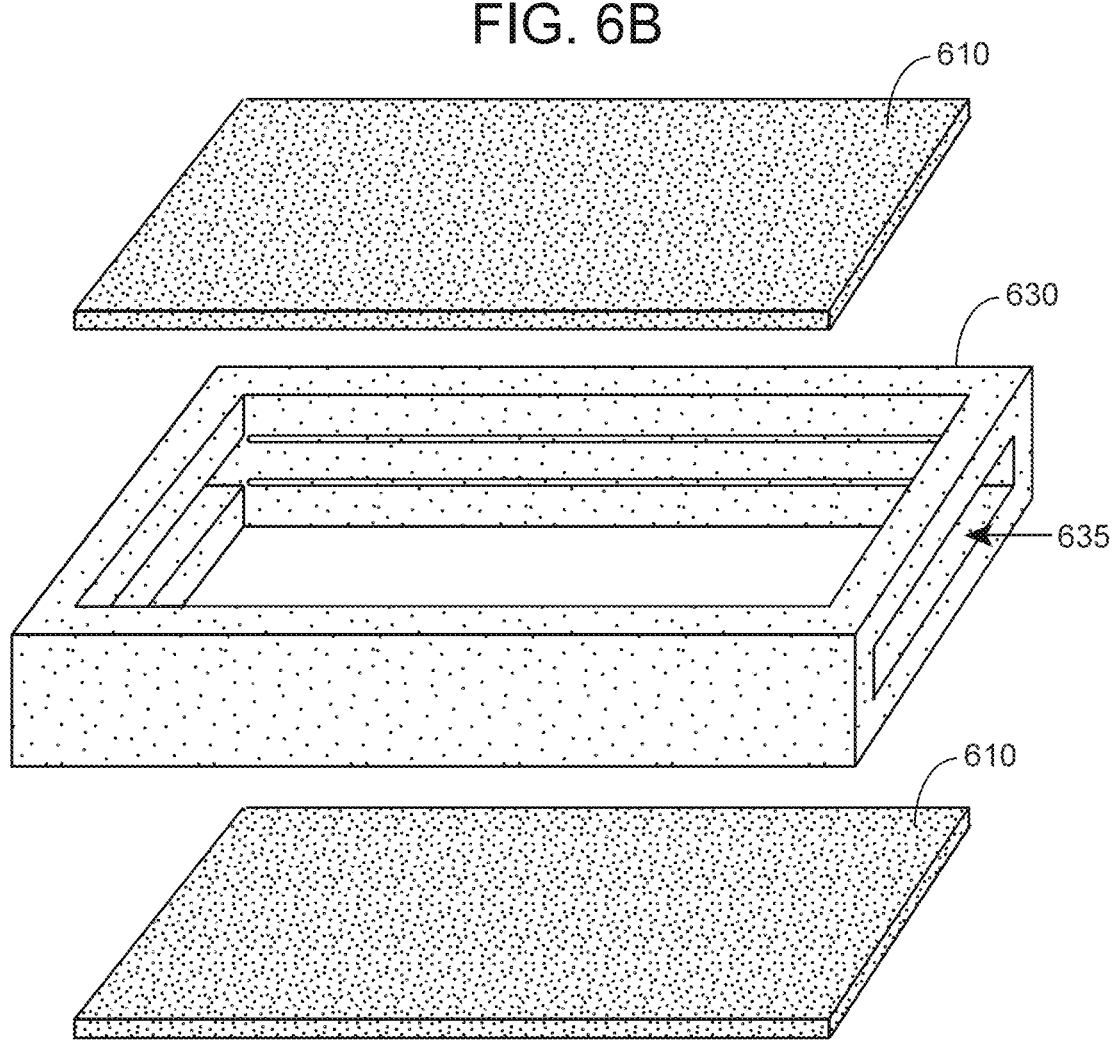
Figure 6C:
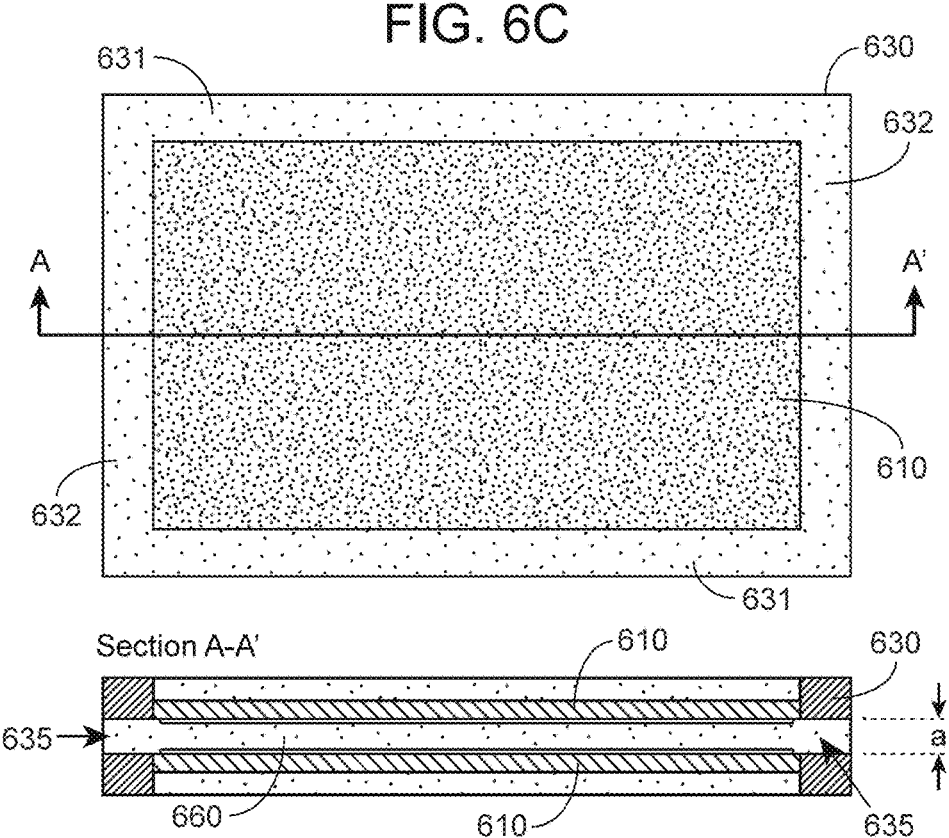
Figure 6D:
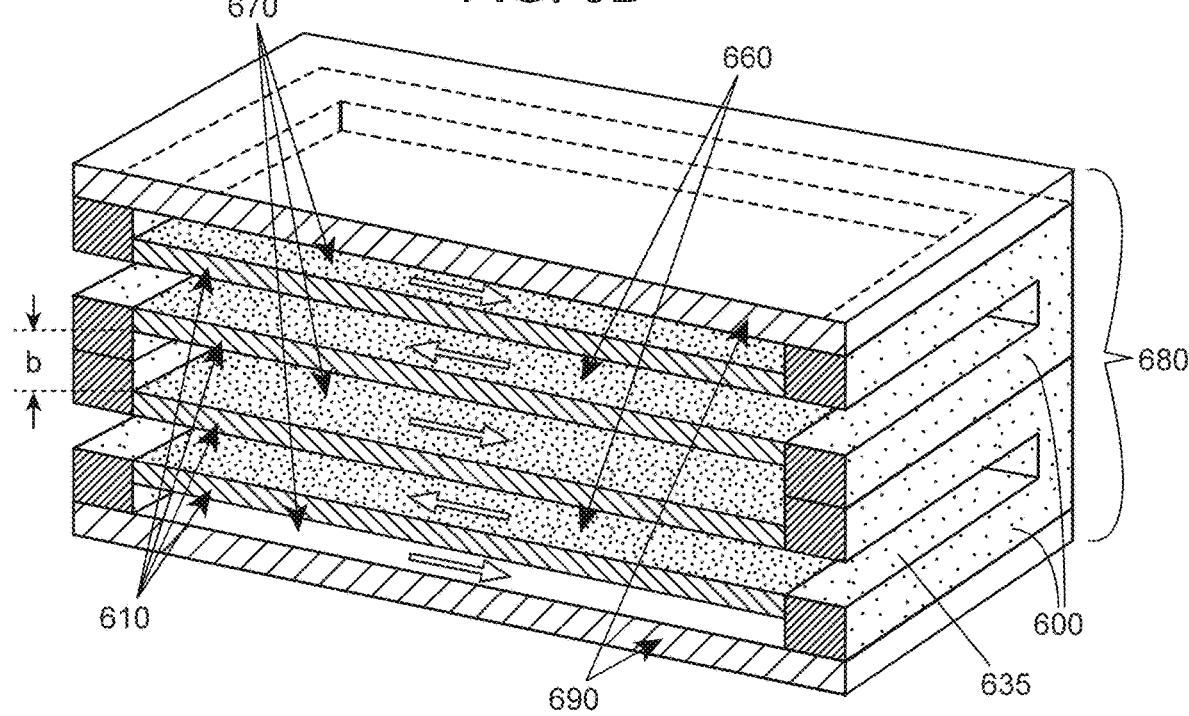

With reference to FIGS. 5A and 5B, a parallel plate device includes a parallel plate assembly 580, having a stack of stackable plate subunits and cover plates capping the top and bottom of the assembly. The cover plates may include access ports 596 that are in fluidic communication with filtrate/dialysate channels formed as a result of stacking the plate subunits and capping them (i.e., latently formed). The plate subunits may have a modular design such that any suitable number of subunits may be combined to form alternating parallel rows of blood channels and filtrate/dialysate channels. Thus, n stackable plate subunits may be stacked and each of the outer-most plate subunits capped with a cover plate to form a parallel plate assembly having n+2 filtrate/dialysate channels interleaved with n blood channels.

The parallel plate device further includes a blood conduit adaptor 593 attached to the ends of the parallel plate assembly 580. The blood conduit adaptors provide an access port 594 for blood to flow into and out of the parallel plate assembly, where each stackable plate subunit provides a blood channel through which blood flows. The blood access port may be configured to receive a vascular graft connector 505 to establish a blood circuit, from and back to a circulatory system of an individual, e.g., an individual in need of hemodialysis.

The present parallel plate devices may achieve a desirable rate of diffusive clearance of components in whole blood. In some cases, the parallel plate device achieves a diffusive clearance of about 25 ml/min/m$^2$ or more, e.g., about 50 ml/min/m$^2$ or more, about 75 ml/min/m$^2$ or more, about 100 ml/min/m$^2$ or more, about 120 ml/min/m$^2$ or more, about 150 ml/min/m$^2$ or more, including about 200 ml/min/m$^2$ or more. In some embodiments, the parallel plate device achieves a diffusive clearance of from about 25 ml/min/m$^2$ to about 250 ml/min/m$^2$, e.g., from about 50 ml/min/m$^2$ to about 200 ml/min/m$^2$, from about 75 ml/min/m$^2$ to about 175 ml/min/m$^2$, including from about 100 ml/min/m$^2$ to about 150 ml/min/m$^2$. The diffusive clearance may be measured with respect to, e.g., creatinine, urea or phosphate ($PO_4^{3-}$).

Figure 2:
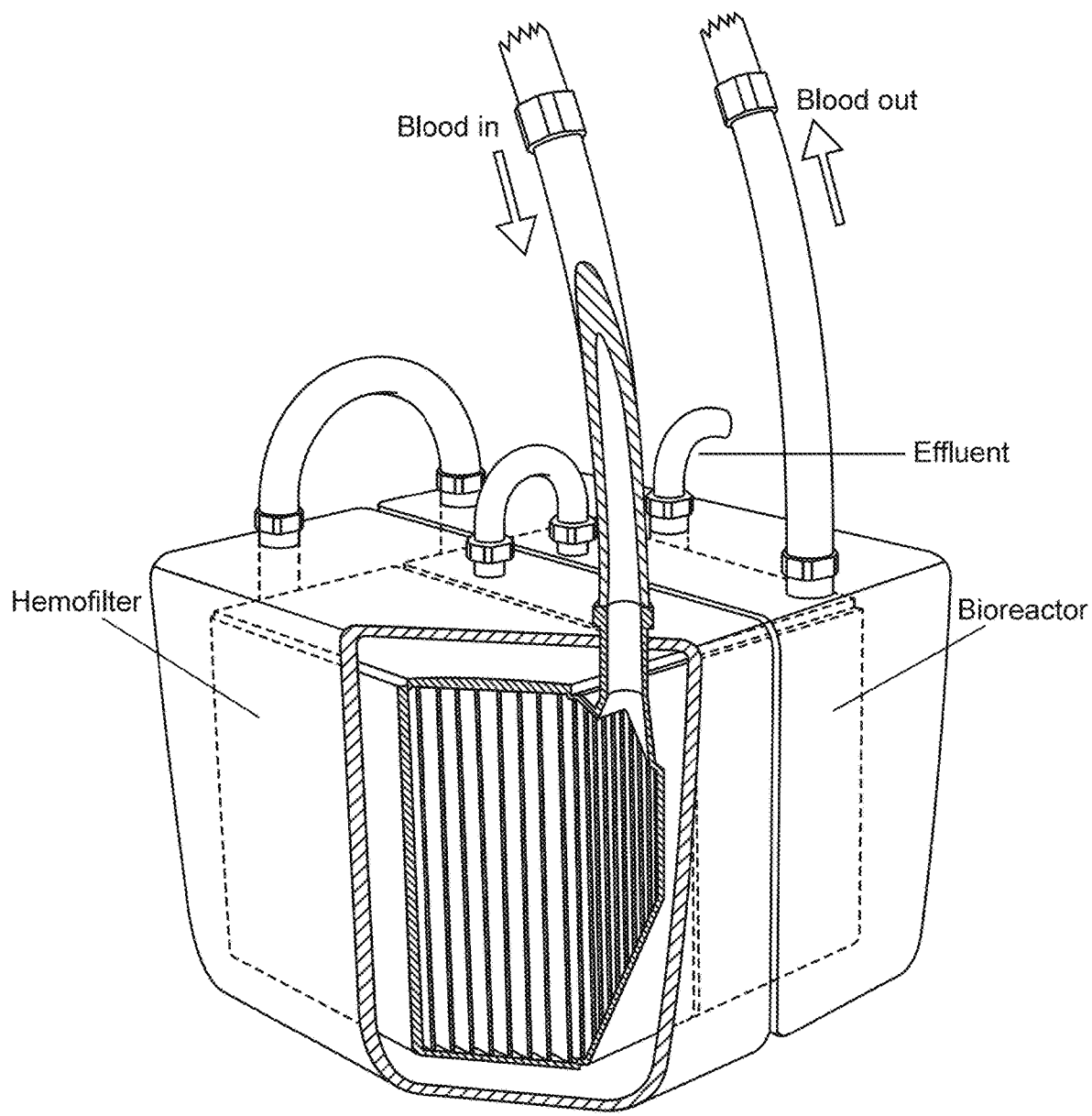
FIG. 2 is a schematic diagram showing an implantable bioartificial kidney containing a hemofiltration device, according to embodiments of the present disclosure.

In some cases, the parallel plate device may be integrated in an artificial kidney, e.g., as depicted in FIGS. 1 and 2, where the parallel plate device may be used to filter blood, and the filtrate may then be directed to a bioreactor to return desirable components in the filtrate back to the blood before it is returned to the circulation.

Further aspects of the present disclosure are now described.

Devices

Plate Subunits and Parallel Plate Assembly

A plate subunit and a parallel plate assembly may be described with reference to FIGS. 6A-6F. The plate subunit 600 includes a pair of silicon nanoporous membranes 610, positioned in a window of a frame 630 such that the two membranes are oriented substantially parallel to each other in a spaced apart configuration. The pair of membranes bound two opposite faces of a planar through channel 660, which may be a blood channel, and the distance (a) between the pair of membranes defines a height of the through channel along the plates. The through channel is further bound by at least part of longitudinal struts 631 of the frame. The through channel opens externally at both ends of the subunit via slots 635 in the transverse struts 632 of the frame. In use, blood may be directed to flow through the blood channel (i.e., the planar through channel) by entering through the slot at one end of the frame, flow along the surface of the membranes (and therefore along the surface of the one or more silicon nanoporous membranes contained therein) towards the opening slot at the other end of the frame and exit there through.

The through channel 660, e.g., blood channel, has a planar configuration such that the height (a) is significantly smaller than the other two mutually orthogonal dimensions (i.e., the length and the width) of the channel. The frame 610 has outer dimensions that in general conform to the dimensions of the through channel. The length of the plate subunit 600 may be defined along a dimension defined by the general direction of flow of through the blood channel. Thus, the length of the blood channel may be substantially the same as the length (i.e., longitudinal length) of the frame. In other words, the through channel and the frame may be coextensive in length.

Two or more plate subunits 600 may be combined to form a parallel plate assembly 680. In the parallel plate assembly, the plate subunits may be aligned and stacked on top of each other, such that a surface of the frame 630 from a first plate subunit interfaces with a surface of the frame from a second plate subunit, and a membrane 610 from the first plate subunit and a membrane from the second plate subunit are oriented substantially parallel to each other, in a spaced apart configuration. The two membranes bound two opposite sides of a dialysate/filtrate channel 670, and the distance (b) between the two membranes defines a height of the dialysate/filtrate channel along the plates. The dialysate/filtrate channel is further bound by the longitudinal struts 631 and the transverse struts 632 of the frame. See also, FIG. 12. The parallel plate assembly may also include cover plates 690, each cover plate being oriented substantially parallel to and in a spaced apart configuration with an outer-most membrane of the stack of plate subunits, to form a dialysate/filtrate channel. Thus, a surface of the frame of an outer-most plate subunit of the stack may interface the cover plate to form the dialysate/filtrate channel.

The frame 630 may be configured in any suitable manner to provide for the height (b) of the dialysate/filtrate channel 670. For example, as shown in FIGS. 6A-D, the frame from the first plate subunit may be configured such that when a membrane is positioned in the frame, a level of the dialysate/filtrate channel side of the membrane is offset from the level of the surface of the frame interfacing the frame of the second plate subunit whose membrane with which the dialysate/filtrate channel is formed. In some cases, the interface along two plate subunits includes a gasket that is compressed upon stacking the plate subunits, and the height of the compressed gasket provides the height (b) of the dialysate/filtrate channel.

Thus, the dialysate/filtrate channel 670 of the parallel plate assembly 680 is latently formed by combining structural features at the interface of two different plate subunits 600 when the plate subunits are aligned and stacked, or at the interface of a plate subunit (i.e., an outer-most plate subunit of a stack of subunits) and a cover plate 690. In contrast, the blood channels 660 are integral to each plate subunit.

The frame 630 further includes one or more through holes 636 that are in fluid communication with dialysate/filtrate channels in the parallel plate assembly. The through holes may further be in fluid communication with an inlet and/or outlet for the dialysate/filtrate to enter and/or exit the present device. The frame may also include recessed areas 638 around each through hole, where the recessed areas provide fluid connectivity between a through hole and the dialysate/filtrate channel. The recessed areas may aid in evenly distributing fluid from the through hole to the dialysate/filtrate channel, or to collect fluid in the dialysate/filtrate channel into the through hole. The through holes may be positioned at any suitable location along the frame, and generally at least a pair of through holes is located on opposing struts of the frame to provide access for the dialysate/filtrate into and out of the dialysate/filtrate channel. In some cases, the through holes are located on the longitudinal struts 631, in which case the blood flow through the through channel 660 and the dialysate/filtrate flow through the dialysate/filtrate channel may be substantially orthogonal to each other. In some cases, the through holes are positioned on the transverse struts 632, in which case the blood flow through the through channel and the dialysate/filtrate flow through the dialysate/filtrate channel may be substantially parallel (e.g., concurrent or countercurrent) to each other. When the through holes are positioned on the transverse struts, the through hole may be configured to pass through a pillar structure 634 that is interposed between transverse struts 632 that form the slot 635 in the frame. Thus, the pillar structures may split a flow of blood through the opening into segments according the number, shape and position of the pillar structures (see also, FIG. 8B).

The number of through holes 636 in a plate subunit 600 may be any suitable number for distributing the dialysate/filtrate to and through each dialysate/filtrate channel 670. In some cases, the plate subunit includes 1 or more, e.g., 2 or more, 3 or more, 4 or more, 5 or more, including 6 or more through holes on one side of the frame 630, and in some cases includes 10 or fewer, e.g., 9 or fewer, 8 or fewer, 7 or fewer, including 6 or fewer through holes on one side of the frame. In some cases, the plate subunit includes from 1 to 10 through holes, e.g., 2 to 9 through holes, 2 to 8 through holes, 2 to 7 through holes, including 2 to 6 through holes. The through holes may generally be positioned in each plate subunit of a parallel plate assembly 680 such that through holes of one plate subunit are aligned with the corresponding through holes of an adjacent plate subunit. In cases where one or more pillar structures 634 are provided to allow the through holes to pass from one dialysate/filtrate channel side to the other dialysate/filtrate channel side, it may be desirable that the number of through holes be kept as low as possible to minimize dividing the through channel opening, but high enough to provide efficient distribution of the dialysate/filtrate through the dialysate/filtrate channel.

The diameter of a through hole 636 may vary depending on the desired flow rate of the dialysate/filtrate, the number of through holes, etc. In some embodiments, the through hole has a diameter of about 0.1 mm or more, e.g., about 0.2 mm or more, about 0.5 mm or more, about 0.75 mm or more, about 1.0 mm or more, about 1.25 mm or more, about 1.5 mm or more, including about 2.0 mm or more, and in some cases may have a diameter of about 5.0 mm or less, e.g., about 4.0 mm or less, about 3.5 mm or less, about 3.0 mm or less, about 2.5 mm or less, including about 2.0 mm or less. In some embodiments, the through hole has diameter of from about 0.1 mm to about 5.0 mm, e.g., from about 0.2 mm to about 4.0 mm, from about 0.5 mm to about 3.5 mm, from about 0.5 mm to about 3.0 mm, including from about 0.75 mm to about 2.5 mm.

The dimensions of the through channel 660 (i.e., blood channel) may vary and may depend on the desired filtration rate and/or dialysis adequacy of the device, which may in turn depend on factors such as the properties of the silicon nanoporous membranes, the total effective area of membrane for filtration/dialysis, the flow rate of the blood, the blood pressure, the number of through channels in a device, etc. In some embodiments, the through channel has a height of about 0.5 mm or more, e.g., about 1.0 mm or more, about 1.5 mm or more, about 2.0 mm or more, including 2.5 mm or more, and in some cases a height of about 5.0 mm or less, e.g., about 4.0 mm or less, about 3.5 mm or less, about 3.0 mm or less, including about 2.5 mm or less. In some embodiments, the through channel has a height of from about 0.5 mm to about 5.0 mm, e.g., from about 1.0 mm to about 4.0 mm, from about 1.5 mm to about 3.5 mm, including about 2.0 mm to about 3.0 mm.

In some cases, the through channel 660 (i.e., blood channel) has a length (i.e., longitudinal length along the general direction of flow of blood through the channel) of about 10 mm or more, e.g., about 20 mm or more, about 30 mm or more, about 40 mm or more, about 50 mm or more, including about 60 mm or more, and in some cases, a length of about 100 mm or less, e.g., 90 mm or less, 80 mm or less, 70 mm or less, including 60 mm or less. In some cases, the through channel has a length of from about 10 mm to about 100 mm, e.g., from about 20 mm to about 90 mm, from about 30 mm to about 80 mm, including about 40 mm to about 70 mm.

In some cases, the through channel 660 (i.e., blood channel) has a width of about 10 mm or more, e.g., about 15 mm or more, about 20 mm or more, about 25 mm or more, about 30 mm or more, including about 35 mm or more, and in some cases, a width of about 100 mm or less, e.g., 80 mm or less, 60 mm or less, 50 mm or less, including 40 mm or less. In some cases, the through channel has a width of from about 10 mm to about 100 mm, e.g., from about 15 mm to about 80 mm, from about 20 mm to about 60 mm, including about 25 mm to about 50 mm.

The dimensions of the dialysate/filtrate channel 670 may vary and may depend on the desired filtration rate and/or dialysis adequacy of the device, which may in turn depend on factors such as the properties of the silicon nanoporous membranes, the total effective area of membrane for filtration/dialysis, the flow rate of the blood, the blood pressure, the number of blood channels in a device, etc. In some embodiments, the dialysate/filtrate channel has a height of about 0.1 mm or more, e.g., about 0.15 mm or more, about 0.2 mm or more, about 0.25 mm or more, including 0.3 mm or more, and in some cases a height of about 5.0 mm or less, e.g., about 2.0 mm or less, about 1.0 mm or less, about 0.8 mm or less, including about 0.6 mm or less. In some embodiments, the dialysate/filtrate channel has a height of from about 0.1 mm to about 5.0 mm, e.g., from about 0.15 mm to about 2.0 mm, from about 0.2 mm to about 1.0 mm, including about 0.25 mm to about 0.8 mm.

The length of the dialysate/filtrate channel 670 (e.g., as defined by the distance between a through hole 636 on one side of the frame 630 to another through hole on the opposite side of the frame) may in general be shorter than the length of the blood channel 660. In some embodiments, The length of the dialysate/filtrate channel may be shorter than the length of the blood channel by from about 1.0 mm to about 10 mm, e.g., from about 2.0 mm to about 8.0 mm, from about 3.0 mm to about 7.0 mm, including about 4.0 mm to about 7.0 mm.

In some embodiments the length of the dialysate/filtrate channel 670 is about 10 mm or more, e.g., about 20 mm or more, about 30 mm or more, about 40 mm or more, about 50 mm or more, including about 60 mm or more, and in some cases, a length of about 100 mm or less, e.g., 90 mm or less, 80 mm or less, 70 mm or less, including 60 mm or less. In some cases, the dialysate/filtrate channel has a length of from about 10 mm to about 100 mm, e g, from about 20 mm to about 90 mm, from about 30 mm to about 80 mm, including about 40 mm to about 70 mm.

In some cases, the dialysate/filtrate channel 670 has a width of about 10 mm or more, e.g., about 15 mm or more, about 20 mm or more, about 25 mm or more, about 30 mm or more, including about 35 mm or more, and in some cases, a width of about 100 mm or less, e.g., 80 mm or less, 60 mm or less, 50 mm or less, including 40 mm or less. In some cases, the dialysate/filtrate channel has a width of from about 10 mm to about 100 mm, e.g., from about 15 mm to about 80 mm, from about 20 mm to about 60 mm, including about 25 mm to about 50 mm.

The frame 630 and the cover plate 690 may be made of any suitable, biocompatible material, and in some cases, may be an implantable, non-biodegradable material. Suitable material for use as the frame includes, without limitation, biocompatible metals (e.g., titanium and alloys thereof), and biocompatible plastics (e.g., polyether ether ketone (PEEK)). In some cases, the frame is a biocompatible metal (e.g., titanium), and the cover plate is a biocompatible plastic (e.g., PEEK).

The number of plate subunits 600 in the parallel plate assembly 680 may vary and may depend on the desired filtration rate and/or dialysis adequacy of the device, which may in turn depend on factors such as the properties of the silicon nanoporous membranes, the total effective area of membrane for filtration/dialysis, the flow rate of the blood, the blood pressure, the dimensions of the blood channel and the dialysate/filtrate channel, etc. In some cases, the parallel plate assembly includes 2 or more, e.g., 3 or more, 4 or more, 5 or more, 7 or more, 10 or more, 15 or more, 20 or more, including 25 or more plate subunits, and in some cases, includes 50 or less, e.g., 40 or less, 35 or less, 30 or less, including 25 or less plate subunits. In some embodiments, the parallel plate assembly includes from 2 to 50 plate subunits, e.g., from 2 to 40 plate subunits, from 3 to 35 plate subunits, from 5 to 35 plate subunits, from 10 to 35 plate subunits, including from 15 to 30 plate subunits.

Figure 7A:
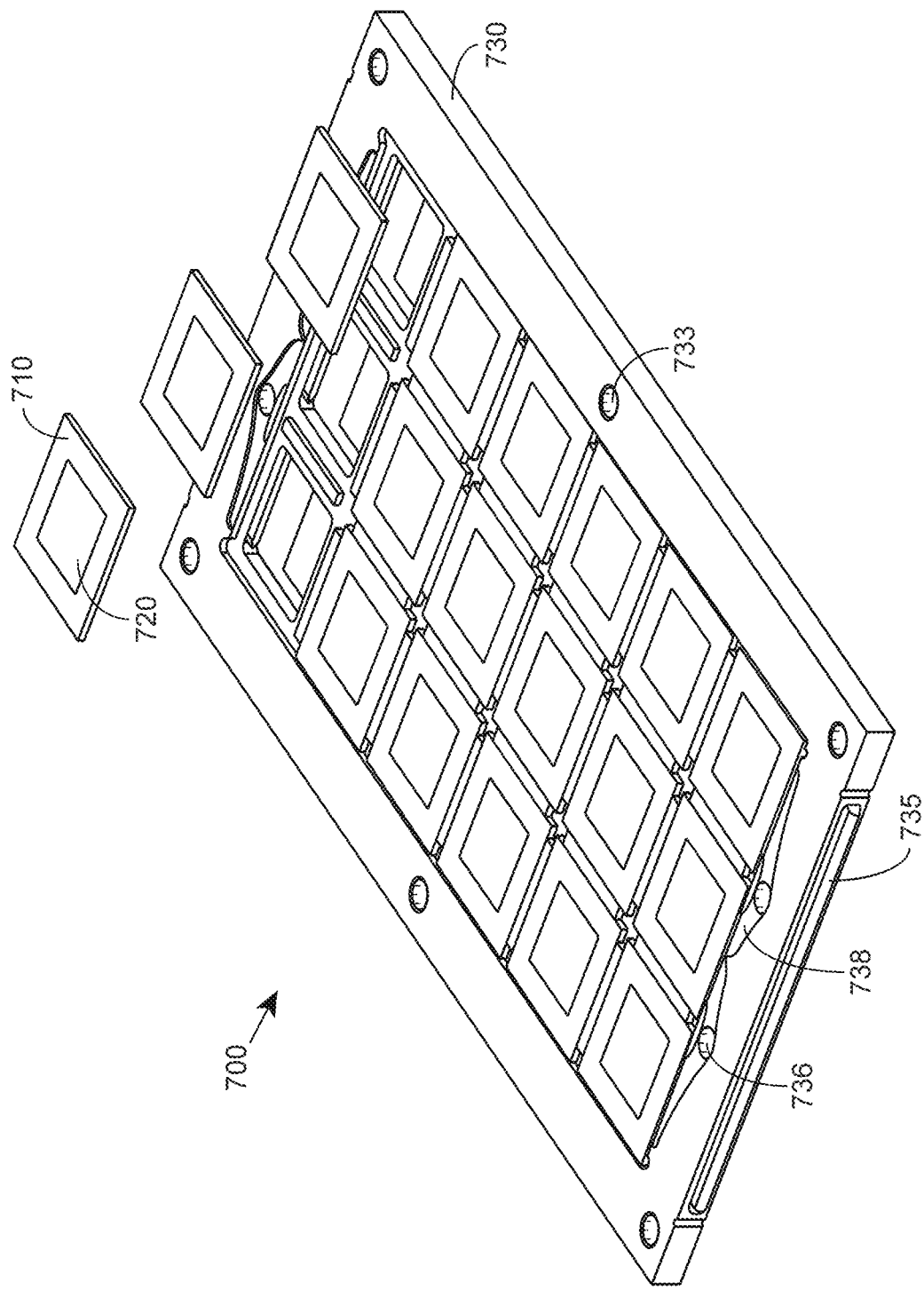

An embodiment of a plate subunit is described with reference to FIGS. 7A and 7B. The plate subunit 700 includes an array (e.g., a 3×8 array) of individual silicon nanoporous membranes 710, each membrane having an effective membrane area 720 that is substantially square (FIG. 7A). Alternatively, the plate subunit may include strips (e.g., two or more, or three or more strips) of silicon nanoporous membranes, each strip having a plurality (e.g., two or more, three or more, four or more, 5 or more, or 6 or more) of effective membrane areas arranged in single file along the strip (FIG. 7B). The effective membrane area may have any suitable lateral dimensions, and in some embodiments, the width and length of the effective membrane area is from about 5.0 mm to about 30 mm, such as about 10 mm. In some cases, the through channel is divided according to the silicon nanoporous membrane strips, such that, e.g., three silicon nanoporous membrane strips bound three parallel through channels separated lengthwise by two dividers (FIG. 7B).

In some embodiments, the plate subunit 700 includes two through holes 736, each associated with recessed areas 738, positioned along each transverse strut of the frame 730. Thus, the filtrate/dialysate channel, when provided within a stack of the plate subunit with another plate subunit or a cover plate, as described above, may have a direction of flow that is substantially parallel to the direction of flow of the blood in a through channel (as indicated by the location of the slots 735). The frame may further include features for aligning and assembling the parallel plate assembly, such as alignment holes 733. In some cases, the frame of the plate subunit includes a groove 739 formed on a surface that interfaces another plate subunit or a cover plate stacked on the plate subunit in the parallel plate assembly. The groove may outline an area of the frame encompassing the filtrate/dialysate flow path (i.e., the area defined by the silicon nanoporous membrane(s), the through hole(s) and any grooves in fluid communication therewith. The groove may be suitable for placing a gasket therein, such that the gasket contacts and is compressed by the surface of a stacked frame, and forms a fluid-tight seal at the plate-plate interface. In some cases, the height of the compressed gasket provides at least part of the height (b) of the filtrate/dialysate channel, as described above.

Figure 8A:
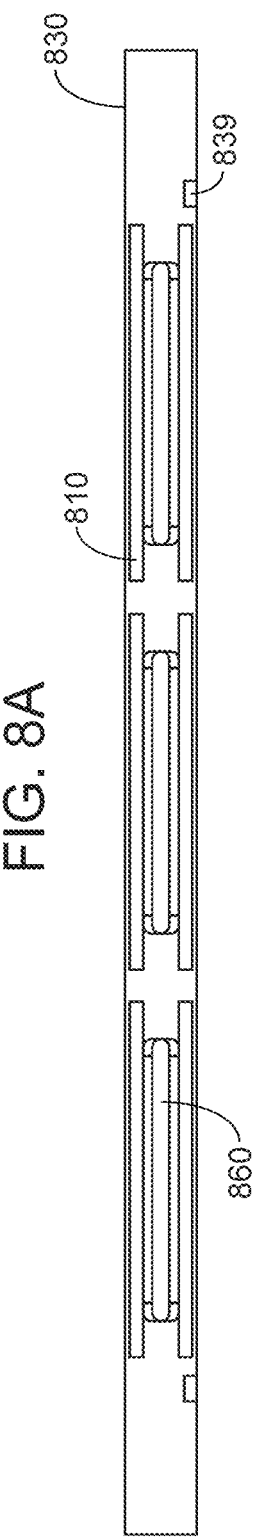
FIGS. 8A and 8B are a collection of drawings showing an end view of a plate subunit (FIG. 8A) and a parallel plate assembly (FIG. 8B), according to embodiments of the present disclosure.
Figure 8B:
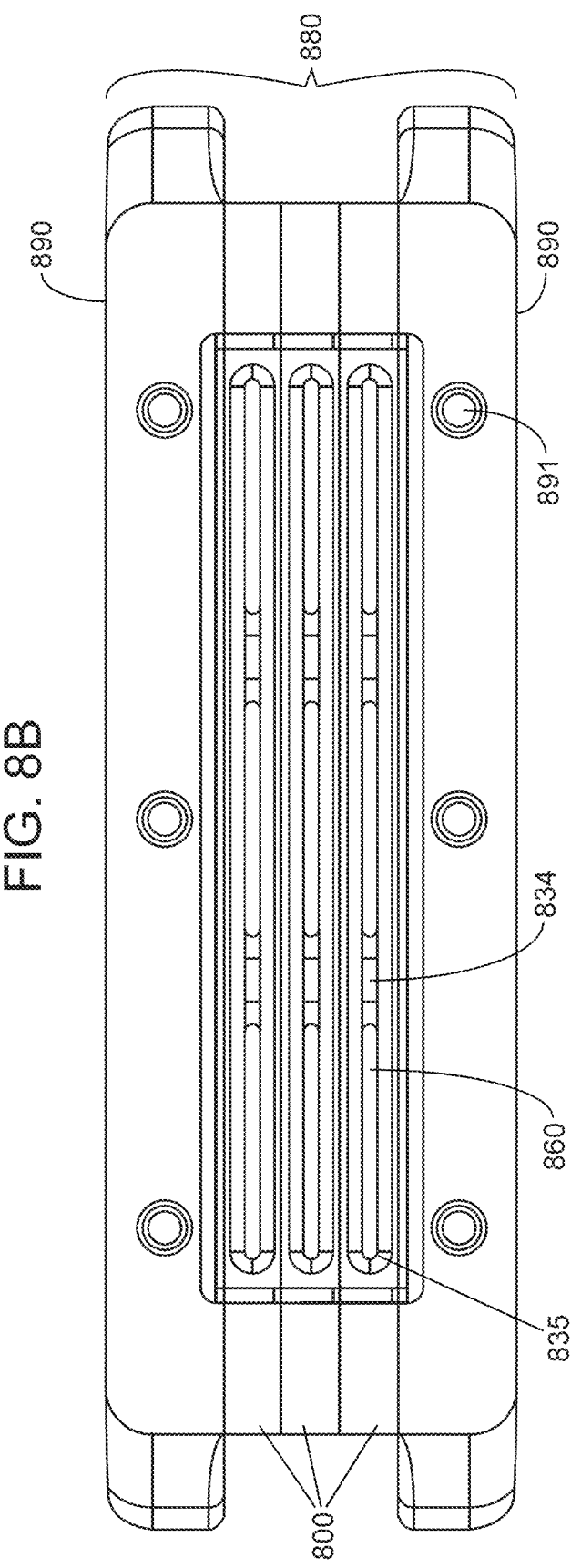

FIGS. 8A and 8B show an end view of a plate subunit (FIG. 8A) and a parallel plate assembly (FIG. 8B), according to embodiments of the present disclosure. In some embodiments, the opening of the through channel 860 in the frame 830 is divided into segments. As described above, the plate subunit may include a groove 839 on one side of the plate subunit, for holding a gasket. The parallel plate assembly 880 may include a two or more, e.g., three or more, 4 or more, 5 or more, 10 or more, 15 or more, or 20 or more plate subunits 800 aligned and stacked on top of each other to provide alternating parallel rows of through channels and latently formed channels. The parallel plate assembly may include cover plate 890 for capping the outer-most plate subunits and thereby forming the outer filtrate/dialysate channels of the alternating parallel rows (see also, FIG. 12). The cover plate may include one or more features 891 (e.g., screw holes) for aligning and securing a blood conduit adaptor to the parallel plate assembly.

Figure 9B:
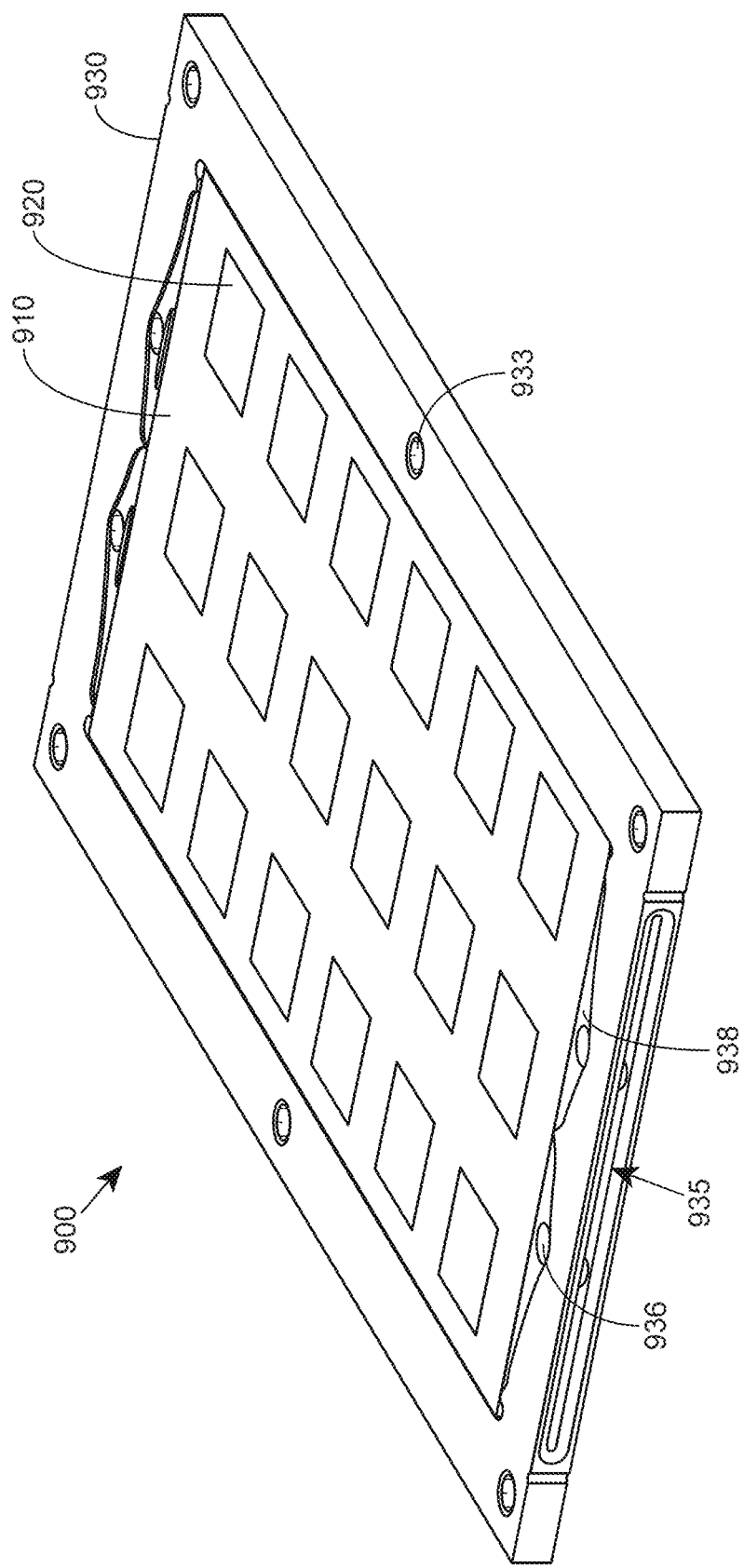

In some embodiments, the silicon nanoporous membrane 910 is a single, monolithic piece, where a pair of the silicon nanoporous membranes are oriented substantially parallel to each other in a spaced apart configuration in the frame 930, to form the plate subunit 900. The silicon nanoporous membrane may include an array (e.g., a 3×8 array) of effective membrane areas 920 (FIGS. 9A and 9B). The array may have any suitable number of rows and/or columns, and may have 2 or more, e.g., 3 or more, 4 or more, 5 or more, including 6 or more rows and/or columns. The effective membrane area may have any suitable lateral dimensions, and in some embodiments, the width and length of the effective membrane area is from about 5.0 mm to about 30 mm, such as about 10 mm. In some embodiments, the frame 930 includes a supporting structure 937 that provides structural support to the silicon nanoporous membrane 910 when positioned in the frame.

Silicon Nanoporous Membranes

The silicon nanoporous membrane 610, 710, 810, 910, 1210 may be any suitable membrane having desirable properties (e.g., hydraulic permeability, sieving coefficient, mechanical integrity, etc.) for use in the present devices. The silicon nanoporous membrane may generally include one or more effective membrane areas where filtration/dialysis can occur across the membrane (i.e., regions that contain the nanopores and allow substance exchange between fluid in the through channel (e.g., blood channel) and fluid in the latently formed channel (e.g., filtrate/dialysate channel)). Suitable silicon nanoporous membranes and methods of making the same are described in, e.g., US20090131858, which is incorporated herein by reference.

In some cases, the silicon nanoporous membrane is a composite membrane of a nanoporous polysilicon layer deposited on a non-porous silicon substrate, where the effective membrane area maybe defined by windows created by selective removal of the silicon substrate. Thus, the thickness of the membrane may be thinner across the effective membrane area than it is across the other areas supported by the silicon substrate. In some embodiments, the thickness of the silicon nanoporous membrane (i.e., including the silicon substrate) is about 10 µm or more, e.g., about 20 µm or more, about 50 µm or more, about 100 µm or more, including about 200 µm or more, and in some embodiments, is about 1,000 µm or less, e.g., about 750 µm or less, about 500 µm or less, about 400 µm or less, including about 300 µm or less. In some cases, the thickness of the silicon nanoporous membrane is from about 10 µm to about 1,000 µm, e.g., from about 20 µm to about 750 µm, from about 50 µm to about 500 µm, including from about 100 µm to about 400 µm.

In some embodiments, the thickness of the silicon nanoporous membrane across the effective membrane area (i.e., the thickness of the polysilicon layer) is about 50 nm or more, e.g., about 100 nm or more, about 150 nm or more, about 200 nm or more, including about 250 nm or more, and in some embodiments, is about 1,000 nm or less, e.g., about 800 nm or less, about 600 nm or less, about 450 nm or less, including about 400 nm or less. In some cases, the thickness of the silicon nanoporous membrane across the effective membrane area is from about 50 nm to about 1,000 nm, e.g., from about 100 nm to about 800 nm, from about 150 nm to about 600 nm, including from about 200 nm to about 400 nm.

The nanopores may have any suitable dimensions to provide for desirable properties (e.g., hydraulic permeability, sieving coefficient) of the membrane. In some cases, the nanopores are slit-shaped, when viewed from above the plane of the membrane, the slit having a length (in the plane of the membrane) that is longer than a width. In some embodiments, the nanopores have a length of about 1.0 µm or more, e.g., about 2.0 µm or more, about 3.0 µm or more, about 4.0 µm or more, including about 5.0 µm or more, and in some cases, a length of about 50 µm or less, e.g., about 25 µm or less, about 20 µm or less, about 15 µm or less, about 10 µm or less, including about 5.0 µm or less. In some cases, the nanopores have a length of from about 1.0 µm to about 50 µm, e.g., from about 2.0 µm to about 25 µm, from about 3.0 µm to about 20 µm, from about 3.0 µm to about 15 µm, from about 3.0 µm to about 10 µm, including from about 4.0 µm to about 5.0 µm.

In some embodiments, the nanopores have a width of about 1.0 nm or more, e.g., about 2.0 nm or more, about 3.0 nm or more, about 5.0 nm or more, including about 7.5 nm or more, and in some cases, a width of about 100 nm or less, e.g., about 75 nm or less, about 50 nm or less, about 40 nm or less, about 30 nm or less, including about 20 nm or less. In some cases, the nanopores have a width of from about 1.0 nm to about 100 nm, e.g., from about 2.0 nm to about 75 nm, from about 3.0 nm to about 50 nm, from about 5.0 nm to about 40 nm, from about 5.0 nm to about 30 nm, including from about 7.5 nm to about 20 nm.

Figure 3A:
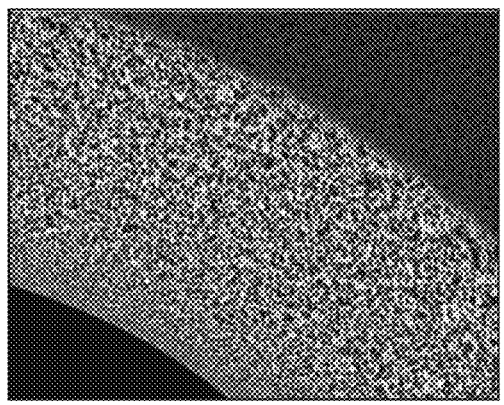
FIGS. 3A and 3B are a collection of images showing different filtration substrates, according to embodiments of the present disclosure.
Figure 3B:
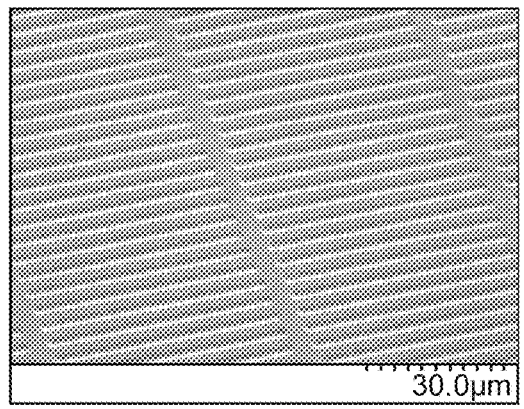
Figure 4:
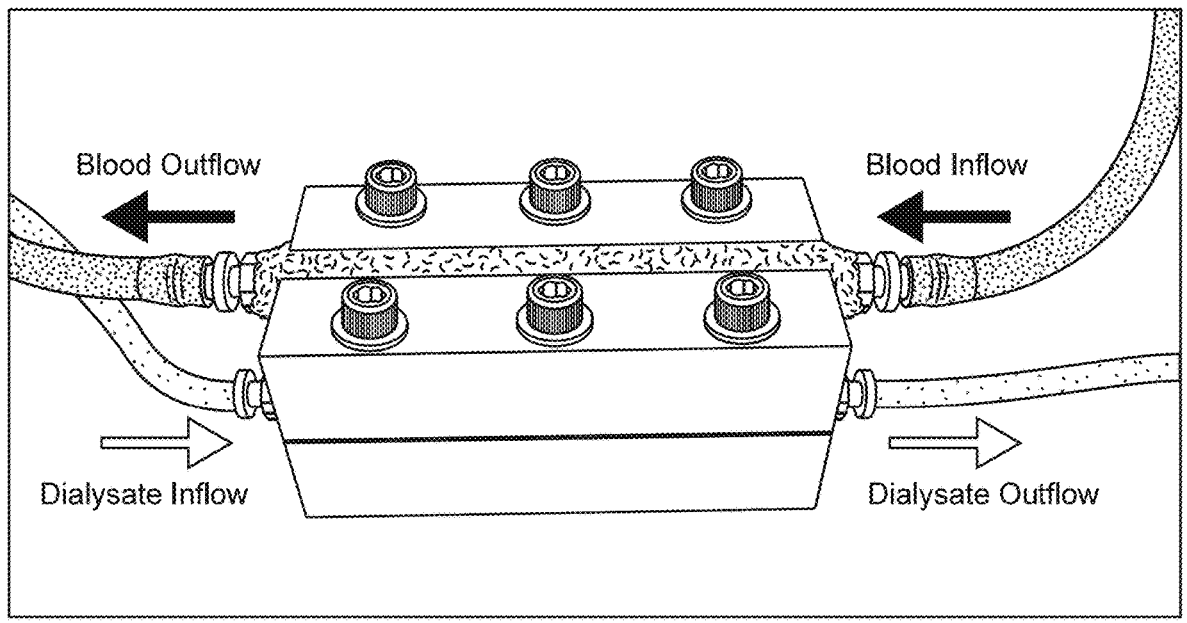
FIG. 4 is a drawing showing a hemodialysis system with a silicon nanoporous membrane, according to embodiments of the present disclosure.

The nanopores may be arranged in any suitable manner, and in some cases, may be arranged in a regular pattern. In some cases, the nanopores are arranged in an array (e.g., of two or more rows and two or more columns of nanopores spaced regularly apart) (see, e.g., FIG. 3B). Adjacent nanopores (e.g., slit-shaped nanopores lying parallel next to each other) may be spaced apart by any suitable distance In some cases, adjacent nanopores may be spaced apart by about 1.0 nm or more, e.g., about 3.0 nm or more, about 5.0 nm or more, about 7.5 nm or more, including about 10 nm or more, and in some cases may be spaced apart by about 1,000 nm or less, e.g., about 500 nm, about 200 nm or less, 100 nm or less, 50 nm or less, including 20 nm or less. In some cases, adjacent nanopores may be spaced apart by from about 1.0 nm to about 1,000 nm, e.g., from about 3.0 nm to about 500 nm, from about 5.0 nm to about 200 nm, from about 7.5 nm to about 100 nm, including from about 7.5 nm to about 20 nm.

The shape of an individual effective membrane area may vary, e.g., depending on the manner in which the silicon substrate is removed from a composite membrane and/or how the nanopores are fabricated on the polysilicon layer. Thus in some cases, an area of a composite silicon nanoporous membrane from which a contiguous block of the silicon substrate is removed may define an individual effective membrane area. In some cases, the individual effective membrane area is substantially square, or substantially rectangular. In some cases, the nanopores are arranged to form concentric circles. Where the individual effective membrane area is substantially square or rectangular, the length or width of the area may be any suitable size. In some cases, the individual effective membrane area has a length and/or width of about 0.1 cm or more, e.g., about 0.2 cm or more, about 0.3 cm or more, about 0.5 cm or more, about 0.75 cm or more, including about 1.0 cm or more, and in some cases, a length and/or width of about 5.0 cm or less, e.g., about 4.0 cm or less, about 3.0 cm or less, about 2.5 cm or less, about 2.0 cm or less, including about 1.5 cm or less. In some embodiments, the individual effective membrane area has a length and/or width of from about 0.1 cm to about 5.0 cm, e.g., from about 0.2 cm to about 4.0 cm, from about 0.3 cm to about 3.0 cm, from about 0.5 cm to about 2.5 cm, including from about 0.75 cm to about 2.0 cm.

The number of effective membrane areas in a silicon nanoporous membrane may vary depending on the desired properties (e.g., hydraulic permeability, sieving coefficient, mechanical integrity, etc.) of the silicon nanoporous membrane. In some embodiments, the silicon nanoporous membrane contains a single effective membrane area (see, e.g., FIG. 7A). In some embodiments, the silicon nanoporous membrane contains a single strip of multiple (e.g., 2 or more, 3 or more, 4 or more, 5 or more, 6 or more, 8 or more or 10 or more) individual effective membrane areas. In some embodiments, the silicon nanoporous membrane contains an array of individual effective membrane areas spaced apart at regular intervals. In some embodiments, the array may include 2 or more, e.g., 3 or more, 4 or more, 5 or more, or 6 or more rows of individual effective membrane areas, and may include 2 or more, 4 or more, 6 or more, 8 or more, or 10 or more columns of individual effective membrane areas.

The silicon nanoporous membrane may have any suitable hydraulic permeability for use in the present devices. In some cases, the hydraulic permeability of the silicon nanoporous membrane is about 50 ml/h/mmHg/m$^2$ or greater, e.g., about 75 ml/h/mmHg/m$^2$ or greater, about 100 ml/h/mmHg/m$^2$ or greater, about 150 ml/h/mmHg/m$^2$ or greater, about 200 ml/h/mmHg/m$^2$ or greater, about 250 ml/h/mmHg/m$^2$ or greater, including about 300 ml/h/mmHg/m$^2$ or greater, and in some cases, is about 1,000 ml/h/mmHg/m$^2$ or less, e.g., about 900 ml/h/mmHg/m$^2$ or less, about 800 ml/h/mmHg/m$^2$ or less, about 700 ml/h/mmHg/m$^2$ or less, about 600 ml/h/mmHg/m$^2$ or less, including about 500 ml/h/mmHg/m$^2$ or less. In some embodiments, the hydraulic permeability of the silicon nanoporous membrane is from about 50 ml/h/mmHg/m$^2$ to about 1,000 ml/h/mmHg/m$^2$, e.g., from about 100 ml/h/mmHg/m$^2$ to about 900 ml/h/mmHg/m$^2$, from about 150 ml/h/mmHg/m$^2$ to about 800 ml/h/mmHg/m$^2$, from about 200 ml/h/mmHg/m$^2$ to about 700 ml/h/mmHg/m$^2$, including from about 200 ml/h/mmHg/m$^2$ to about 600 ml/h/mmHg/m$^2$.

The silicon nanoporous membrane may be surface treated to provide desirable surface properties (e.g., antifouling, anticoagulant, protein and/or cell non-adhesive properties, etc.). In some embodiments, the surface treatment or modification promotes attachment of specific animal cells to the membrane, promotes attachment of desirable proteins, inhibits undesirable protein deposition on the membrane, or inhibits blood coagulation on or in the vicinity of the membrane. Such treatments or modifications may include but are not limited to patterned or unpatterned adsorption or covalent linkage to the membrane surface of RGD peptide moieties, integrins, fibronectin, laminin, collagens, oligosaccharides, or polyethylene glycol moieties. Particular cells or molecules attached to or located at the membrane surface and/or within the pores may be used to render the porous membrane more biocompatible, less thrombogenic, or may be used to alter the filtration characteristics of the pores. Furthermore, the cells may be used to process or modify the filtrate produced by the membrane. In some embodiments, modification of the pores includes but is not limited to covalent attachment of peptides or proteins, either alone or selected to promote attachment of cells such as endothelial or epithelial cells.

In some embodiments, the surface of the silicon nanoporous membranes of the present invention are modified with polyethylene glycol (PEG) or related compounds (e.g., oligosaccharide surfactant polymer monolayers). In some embodiments, the surface of the silicon nanoporous membranes of the present invention are modified with a zwitterionic polymer or copolymer, such as a polymer containing repeat units derived from sulfobetaine-containing and/or carboxybetaine-containing monomers. Suitable monomers include, without limitation, sulfobetaine methacrylate (SBMA), sulfobetaine acrylamide, sulfobetaine methacrylamide, carboxybetaine methacrylate (CBMA), carboxybetaine acrylamide and carboxybetaine methacrylamide. Examples of suitable zwitterionic polymers or copolymers include, without limitation, poly-sulfobetaine methacrylate (pSBMA), poly(carboxy betaine methacrylate) (polyCBMA), poly(carboxybetaine acrylamide), poly(carboxybetaine methacrylamide), poly(sulfobetaine acrylamide), and poly(sulfobetaine methacrylamide).

Parallel Plate Devices

Figure 10A:
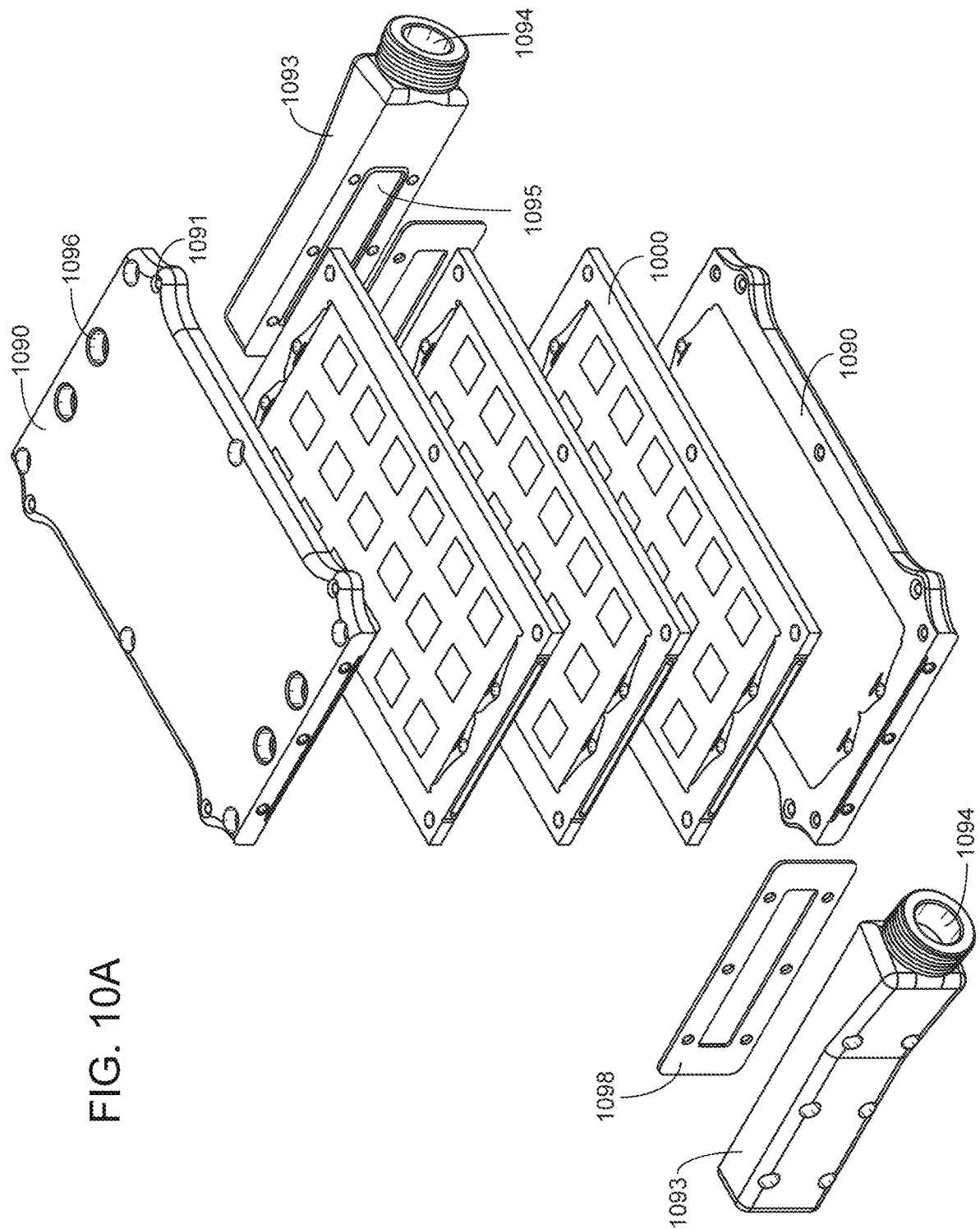
FIGS. 10A-10C are a collection of drawings showing a parallel plate device, according to embodiments of the present disclosure.
Figure 10B:
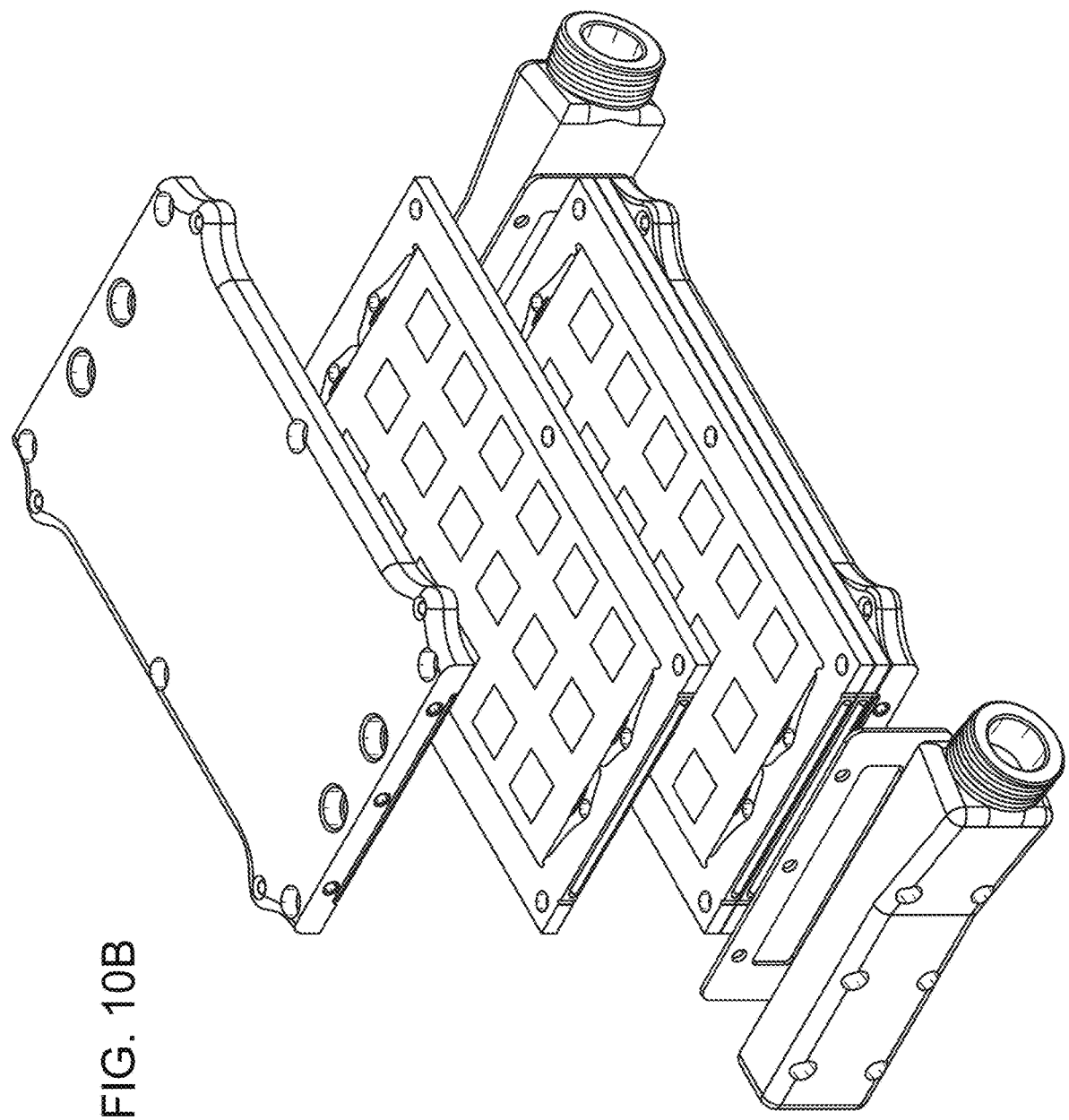
Figure 10C:
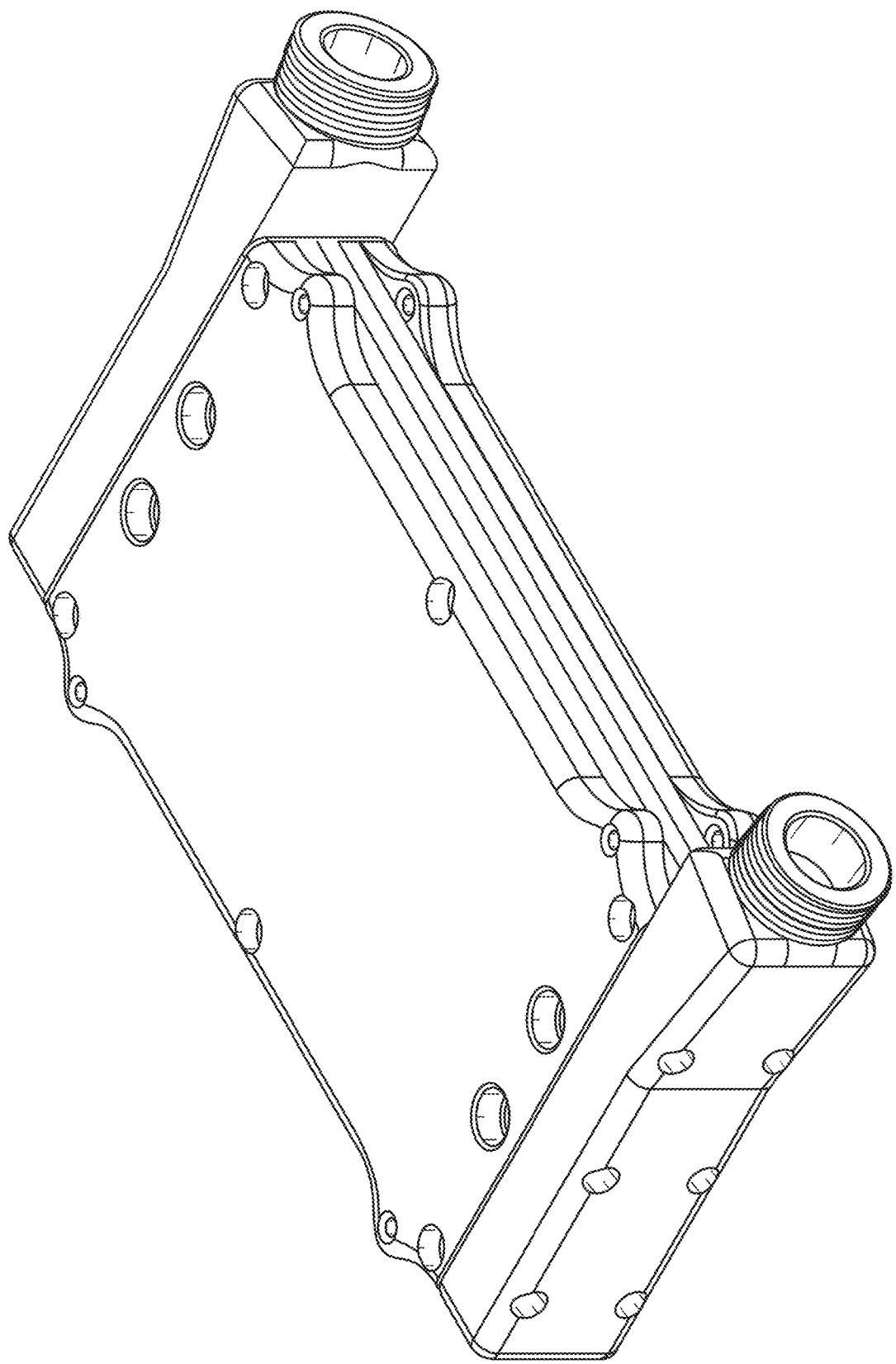

FIGS. 10A-10C depict an embodiment of a parallel plate device. The parallel plate device includes a parallel plate assembly having a plurality of (e.g., two or more, three or more, 5 or more, 10 or more, or 20 or more) plate subunits 1000, each having a blood channel, as described above, aligned and stacked on top of each other, and cover plates 1090 positioned to cap the outer-most plate subunits, the plate subunits and cover plates together providing alternating, parallel layers of blood channels and dialysate/filtrate channels. The plate subunits and cover plates may be aligned such that the through holes of the plate subunits and an access port 1096 of the cover plates form a conduit for dialysate/filtrate that is in fluid communication with the dialysate/filtrate channels. The dialysate/filtrate access ports may in some cases be provided on a dialysate/filtrate plate subunit, which may be integrated into the parallel plate assembly, and the access ports may be positioned along the frame of the dialysate/filtrate plate subunit (see also, FIG. 16A).

The end of the parallel plate assembly having the blood channel openings may provide an interface for introducing blood into the blood channels. Thus, the present hemofiltration device may include blood conduit adaptors 1093 that are positioned at the interface of the parallel plate assembly. The adaptor includes an access port 1094 that provides for an inlet or outlet for blood, and is configured to distribute the flow of blood to the blood channels, or collect blood from the blood channels, via an aperture 1095. The blood conduit adaptors may be made of any suitable, biocompatible material, and in some cases, may be an implantable, non-biodegradable material. Suitable material for use as the adaptor includes, without limitation, biocompatible metals (e.g., titanium and alloys thereof), and biocompatible plastics (e.g., polyether ether ketone (PEEK)).

The dimensions of the blood conduit adaptor 1093, the orientation of the access port 1094 relative to the parallel plate assembly, the number of access ports on an adaptor, and the internal shape of the adaptor may be configured in any suitable manner to interface the parallel plate assembly and provide overall hemocompatibility to the device. In some embodiments, the access port is configured such that the blood flows into or out of the device in a direction substantially parallel to the orientation of the blood channels. In some embodiments, the access port is configured such that the blood flows into or out of the device in a direction substantially perpendicular to the orientation of the blood channels.

The access port 1094 may be further configured to attach a vascular graft connector to direct flow of blood to or from a blood vessel in an individual (see also, FIG. 5B). In some embodiments, a spacer 1098 is interposed between the adaptor and the parallel plate assembly.

In some embodiments, the cover plate 1090 includes one or more (e.g., two or more, three or more, four or more, five or more, or six or more) suture tabs 1091 to facilitate anchoring the device in an implantation site. In some cases, the suture tabs are integrated into the cover plate.

Figure 11A:
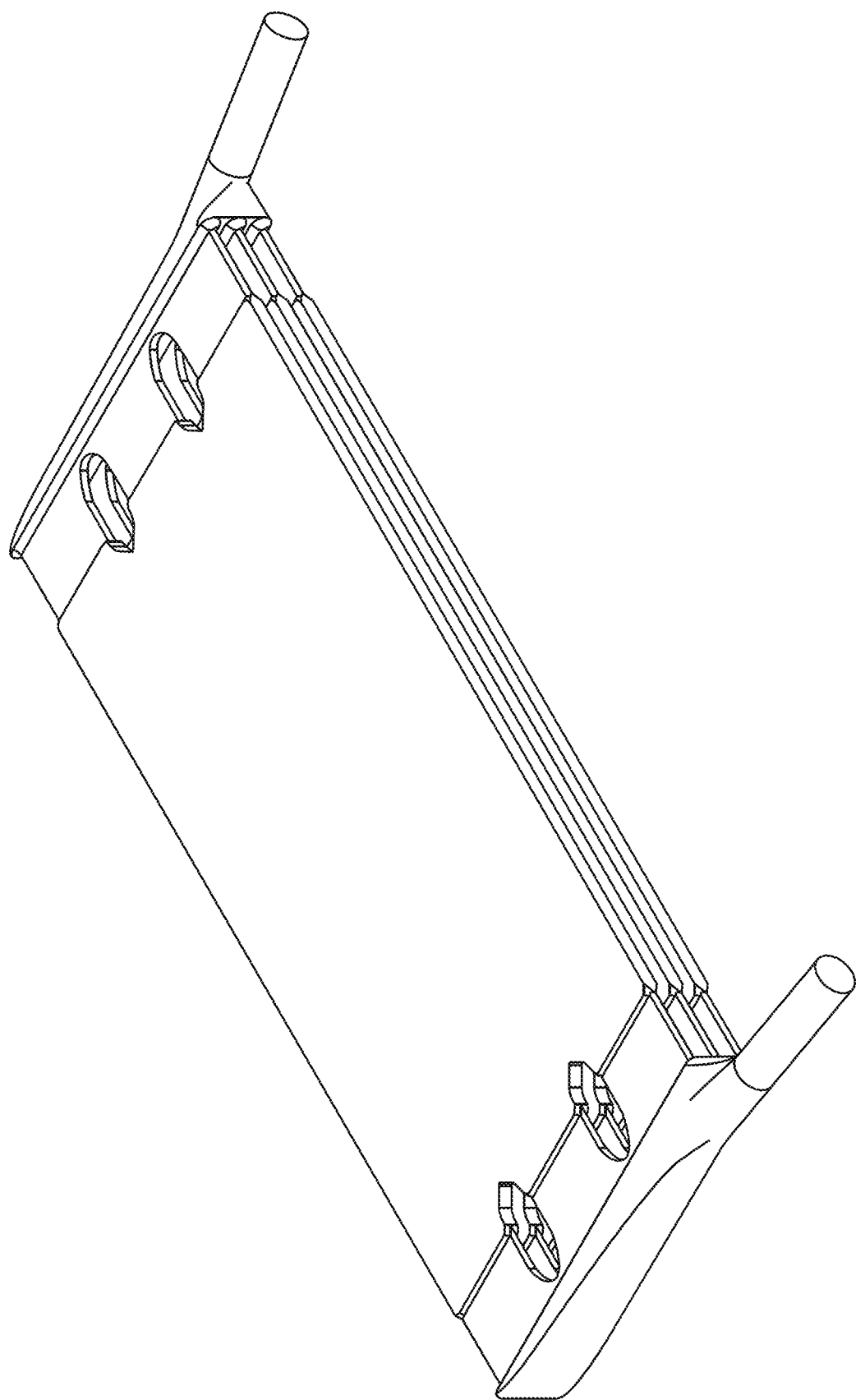
Figure 14A:
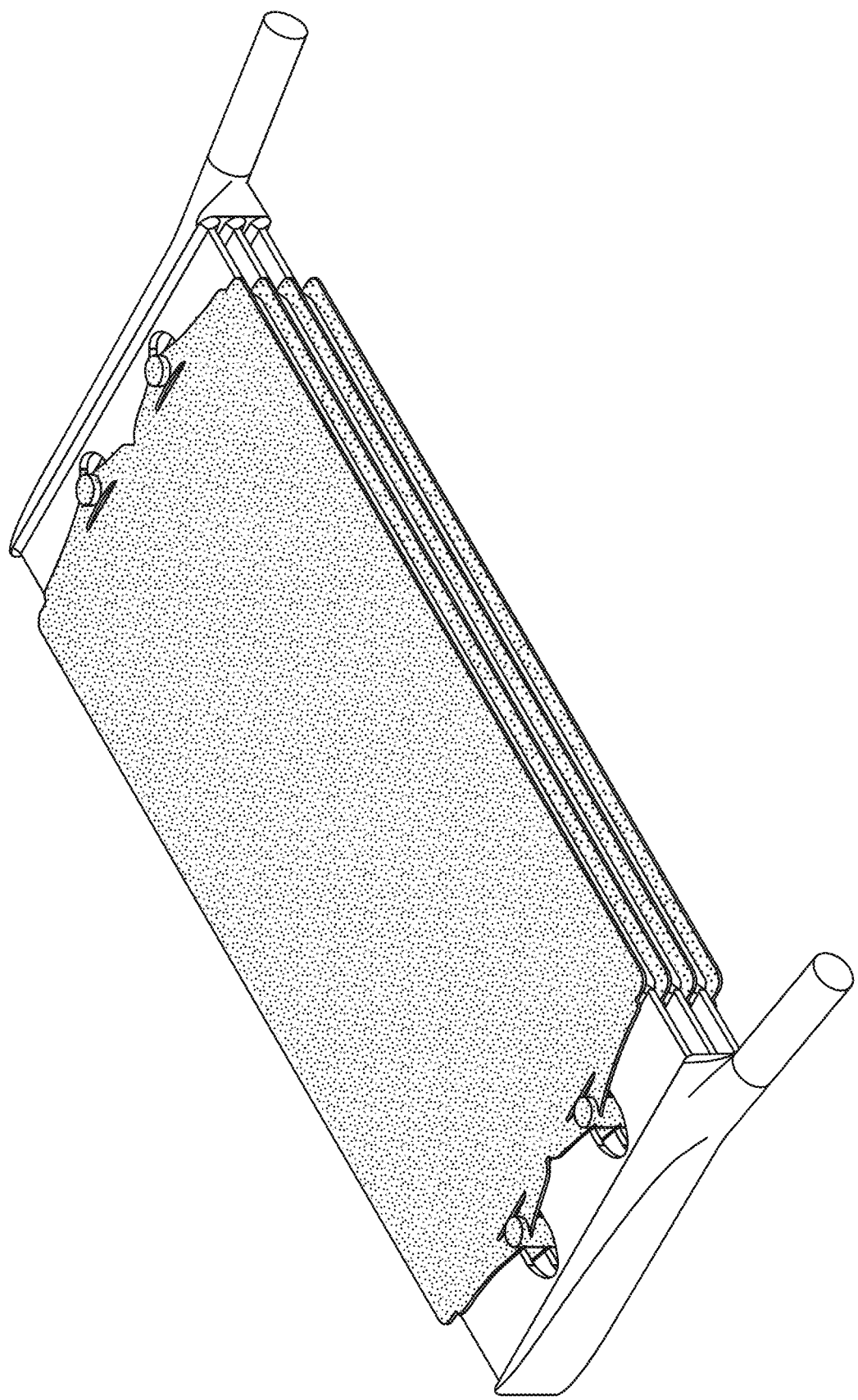

The blood compartments (e.g., the blood channel, the blood conduit in the adaptor, etc.) of a device of the present disclosure is shown in FIGS. 11A-11D. The blood channel may have a central taller segment, where the blood is in contact with the silicon nanoporous membranes, flanked by shorter segments where the blood channel passes through the slot in the struts of the frame. As shown in FIG. 11C, the blood channel may be divided into separate flows at the slots by the pillar structures and/or the support structures of the frame. The blood conduit through the adaptors may have a taper that narrows distally from the blood access port.

With reference to FIG. 12, a partial cutout of a parallel plate assembly 1280 shows the filtrate/dialysate compartment of a device of the present disclosure. Here, cover plates on the top and bottom plate subunits 1200 are not visualized but are considered to be present to provide for the outer-most filtrate/dialysate channels 1270. As described above, each plate subunit provides a blood channel 1260 that is accessible through the slot 1235 at both ends of the plate subunits. Thus, for example, three plate subunits provide three blood channels.

As described above, the filtrate/dialysate channels 1270 are provided by the space bound by a silicon nanoporous membrane 1210 from a first plate subunit 1200 and a silicon nanoporous membrane from a second plate subunit, or a surface of a cover plate. Thus, for example, three plate subunits and two cover plates provide for four filtrate/dialysate channels, having three blood channels 1260 interposed there between in alternating order, where adjacent channels are separated by one of six silicon nanoporous membranes (see also, FIGS. 14A-14D).

The through holes in the frame of the plate subunits 1200 may be aligned to allow distribution of filtrate/dialysate to, or collection of filtrate/dialysate from, each filtrate/dialysate channel 1270.

FIGS. 13A-13D shows the filtrate/dialysate compartment, in isolation of the device depicted in FIGS. 10A-10C.

The blood compartment and the filtrate/dialysate compartment, in isolation of the device, is shown in FIGS. 14A-14D. As the blood channels are provided by the plate subunits in the form of through-channels, and the filtrate/dialysate channels are distributed via through holes integrated into the frame of the plate subunits, the length of the blood channels is in general shorter than the length of the filtrate/dialysate channels.

Figure 15A:
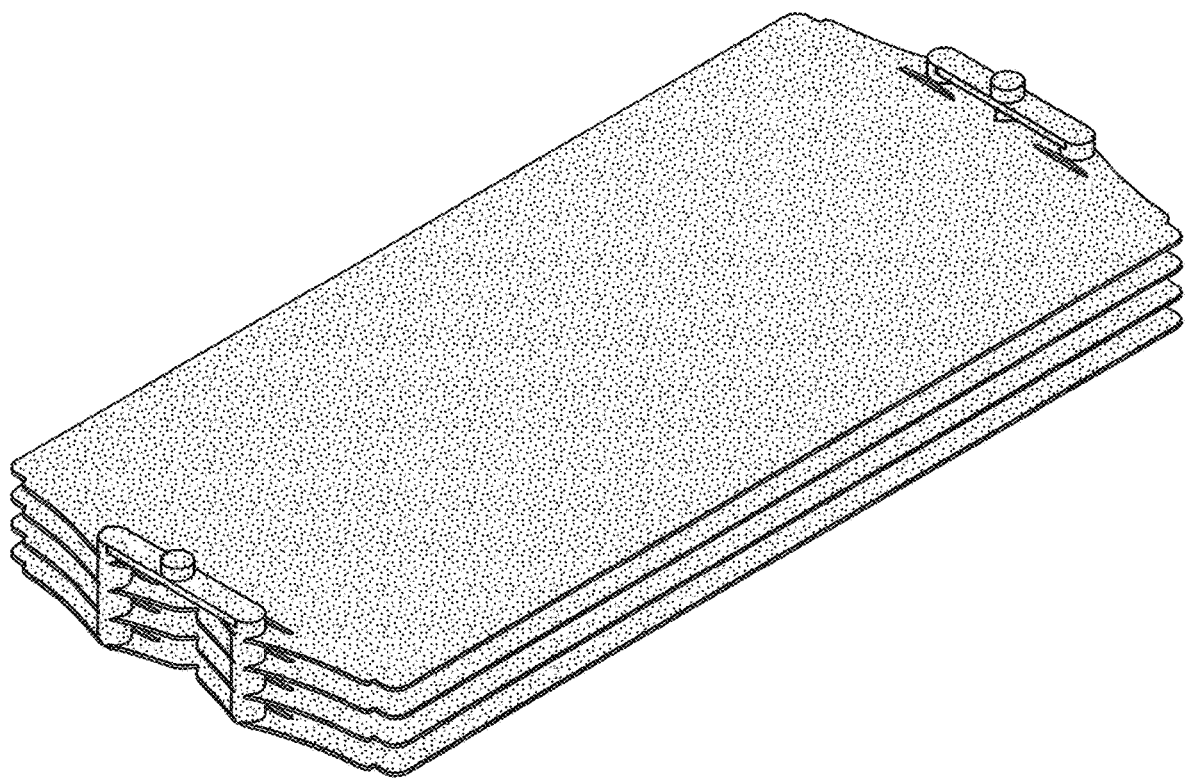
FIGS. 15A and 15B are a collection of drawings showing the filtrate/dialysate compartment of a parallel plate device, according to embodiments of the present disclosure.
Figure 15B:
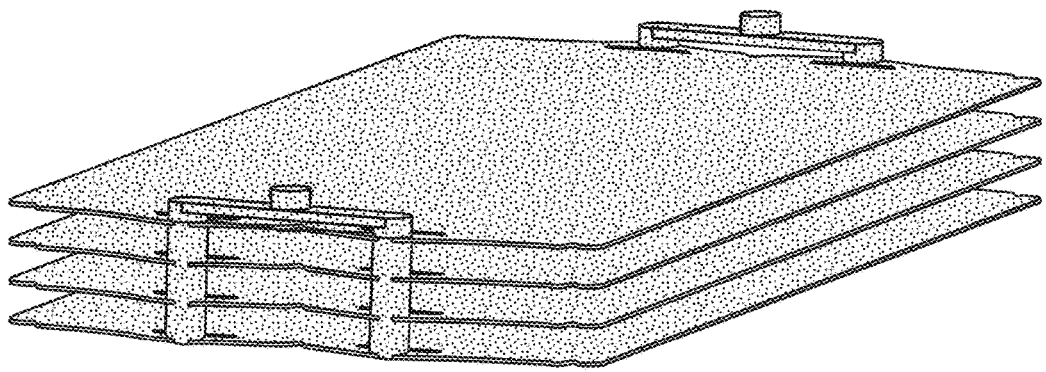

FIGS. 15A and 15B depict the filtrate/dialysate compartment of an embodiment of the present device, where a single filtrate/dialysate access port is provided on each side of the cover plate of a parallel plate assembly. In such cases, an access port be positioned on each side of a cover plate, and the cover plate may be configured to distribute the filtrate/dialysate to the through holes in the interfacing plate subunit.

Figure 16A:
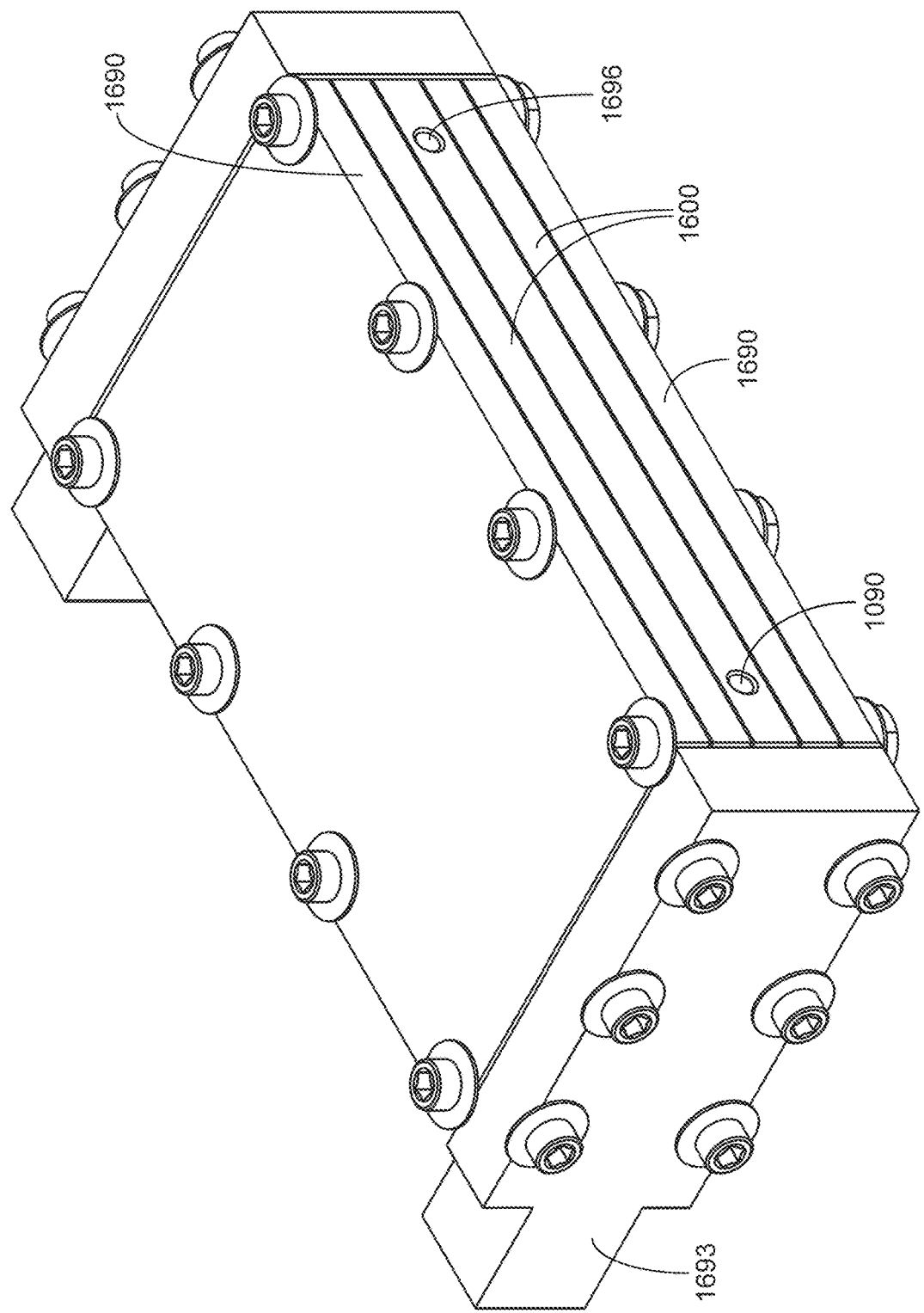
FIGS. 16A-16C are a collection of drawings showing a parallel plate device and the filtrate/dialysate compartment thereof, according to embodiments of the present disclosure.
Figure 16B:
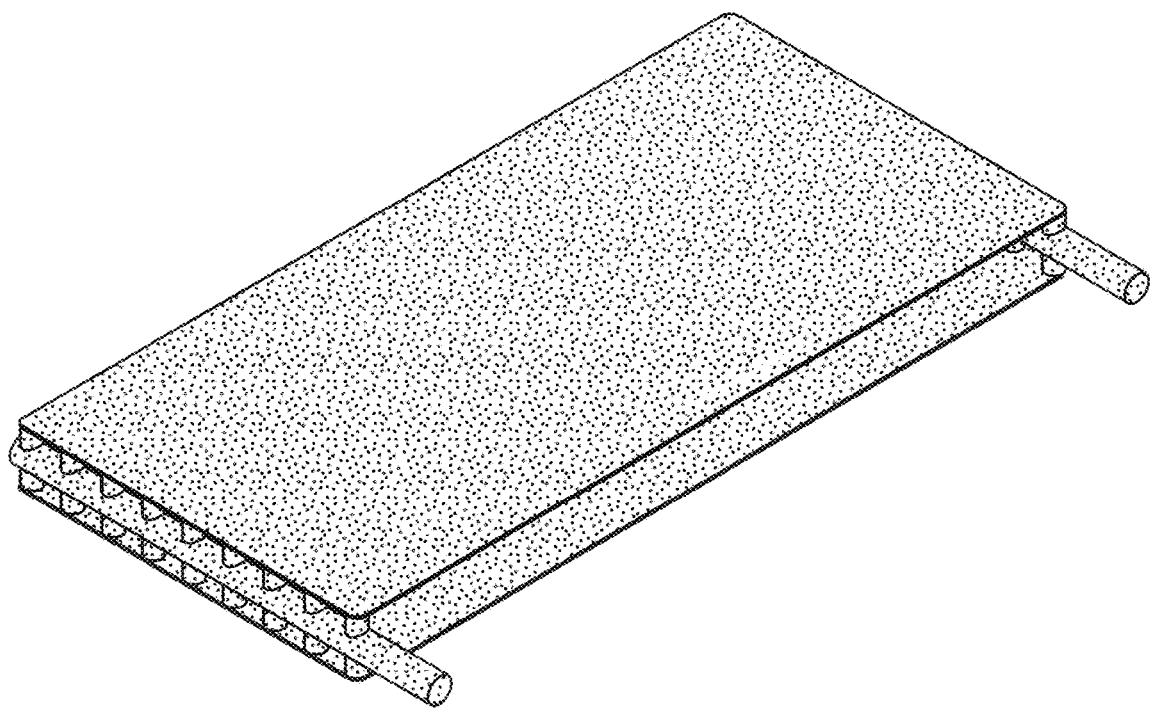
Figure 16C:
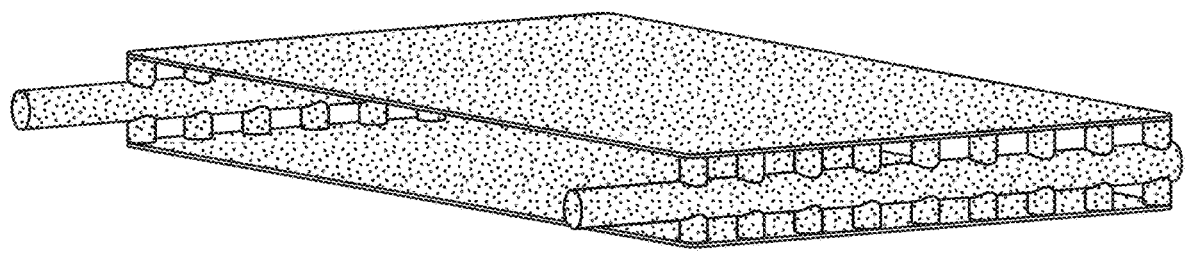

In some embodiments, the device includes a dialysate/filtrate plate subunit 1640 that can be aligned and stacked with the plate subunits 1600 (FIG. 16A). The dialysate/filtrate plate subunit may include filtrate/dialysate access ports 1696 positioned along the frame of the dialysate/filtrate plate subunit, and may be configured to distribute the filtrate/dialysate to the dialysate/filtrate channels. In some cases, the dialysate/filtrate conduit through the dialysate/filtrate plate subunit may include a series of holes that is in fluid communication with a dialysate/filtrate channel (FIGS. 16B and 16C, depicting the filtrate/dialysate compartment of the device shown in FIG. 16A). Thus, in some embodiments, the dialysate/filtrate enters or exits the device at the dialysate/filtrate access port in a direction substantially parallel to the direction in which the blood enters or exits the device at the blood access port. In some cases, the dialysate/filtrate access port(s) and the blood access ports are on the same side of the parallel plate device. (See also, FIG. 17).

A parallel plate hemofiltration device of the present disclosure may further include one or more sensors, e.g., pressure sensors, to monitor the blood pressure of the blood in a blood channel, the pressure of the dialysate or filtrate in a dialysate/filtrate channel, and/or to monitor the pressure difference across a silicon nanoporous membrane.

Systems

Figure 28:
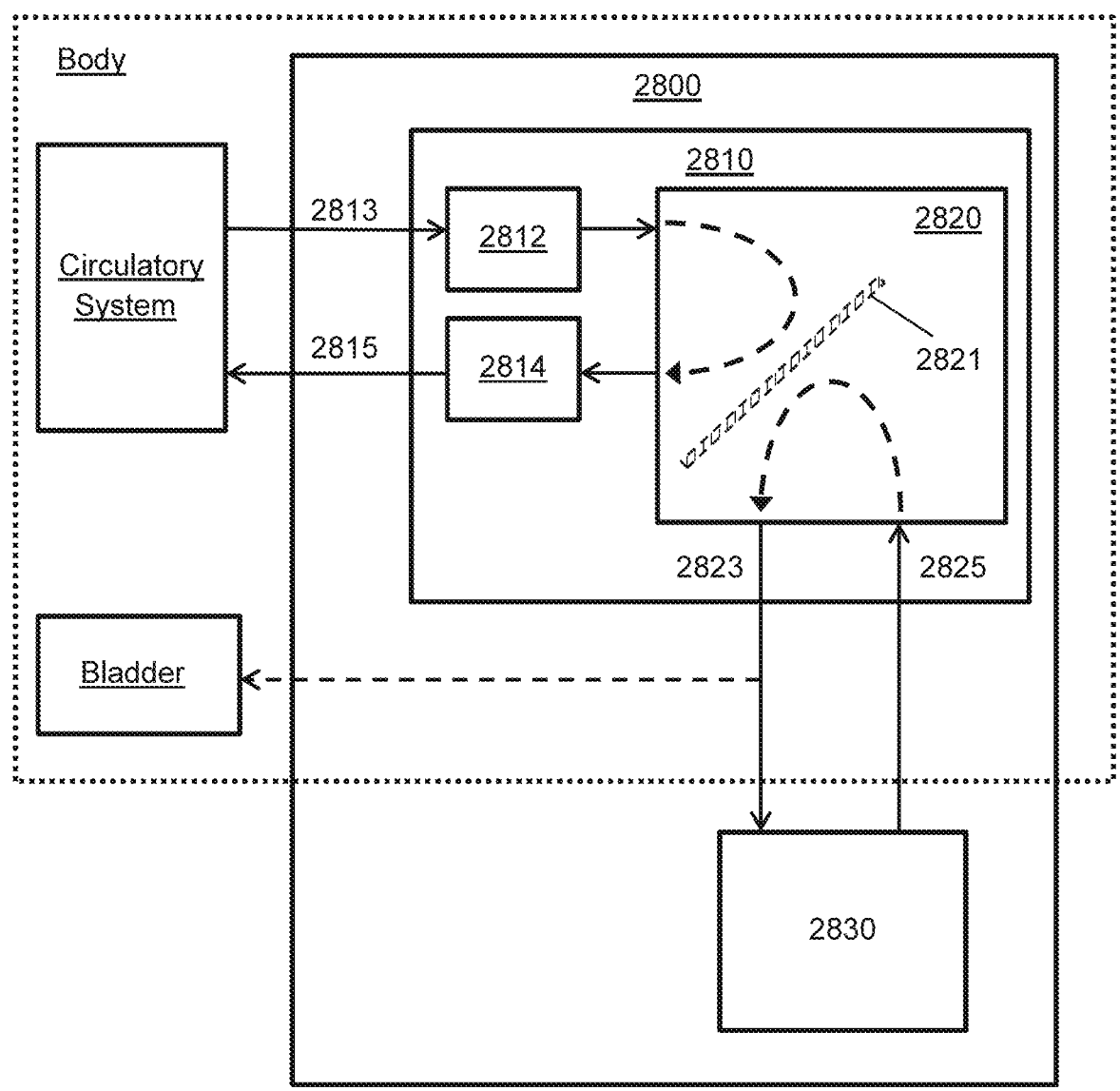
FIG. 28 is a schematic diagram showing an implantable hemofiltration/hemodialysis system, according to embodiments of the present disclosure.

Also provided herein is a system for hemofiltration/hemodialysis that includes a parallel plate hemofiltration device. With reference to FIG. 28, the present system 2800 may include a parallel plate device 2810, as described above, having a parallel plate assembly 2820 with plate subunits 2820 holding silicon nanopore membranes, a filtrate/dialysate outlet, a blood inlet 2812, a blood outlet 2814; vascular graft connectors 2813, 2815 connected to the blood inlet and blood outlet, and configured to direct flow of blood from and back to an individual's circulation, respectively; and a filtrate/dialysate line 2823 (e.g., tubing) connected to the filtrate/dialysate outlet. The blood compartment of the parallel plate device, when connected to the body circulatory system via the vascular graft connectors, forms a pumpless blood circuit that circulates blood without any external pressure source. In other words, the pressure drop across the parallel plate device is sufficiently small such that the blood pressure provided by the circulatory system is sufficient to achieve the desired blood flow rate through the parallel plate device.

The system 2800 may be an implantable system, where at least the parallel plate hemofiltration device and the vascular graft connectors are implanted in the body of an individual. The filtrate/dialysate conduit may be configured to direct filtrate exiting the hemofiltration device to a waste reservoir, where the waste reservoir may be the bladder, or a receptacle external to the body of the individual.

In some cases, the system 2800 is a portable system, where the parallel plate hemofiltration device is located outside of the individual's body, and may be attached to the body (e.g., strapped to the body, attached to a part of clothing, etc.) in any convenient manner.

In some embodiments, the parallel plate assembly 2820 further includes a dialysate inlet and a second dialysate line 2825 may be connected to the dialysate inlet, e.g., where the system is a hemodialysis system. In a hemodialysis system, the filtrate/dialysate line may be connected to a dialysate pump 2830.

The vascular graft connectors 2824, 2826 may include any suitable biocompatible tubing for establishing a blood flow between the individual's circulation and the parallel plate hemofiltration device. In some embodiments, the vascular graft connector includes a polymeric material, including, but not limited to, polyesters, such as polyethylene terephthalate (PET); fluorinated polymers, such as polytetrafluoroethylene (PTFE); polyurethanes and combinations thereof. Suitable polymers include DACRON™ (PET) from DuPont, and FUSION™ (expanded PTFE and PET) from Maquet.

The vascular graft connectors 2813, 2815 may have a suitable stiffness so as to provide flexibility for implanting at an implantation site, and to prevent excessive bending that may collapse the inner passageway (i.e., prevent kinking). In some embodiments, the stiffness of the connector is higher more proximal to the blood inlet 2812 or the blood outlet 2814 than the stiffness of the connector more distal to the blood inlet or the blood outlet of the parallel plate hemofiltration device. The different stiffness may be provided using any suitable method. In some embodiments, the vascular graft connector is a composite connector, having a polymeric tubing that serves as the vascular graft, and a polymeric sleeve attached to the end of the tubing proximal the blood inlet or the blood outlet of the parallel plate hemofiltration device, thereby providing structural reinforcement to the tubing. The polymeric sleeve may be made of any suitable biocompatible polymer, such as, but not limited to, silicone, polysiloxane, poliglecaprone, polydioxanone, polyglactin, caprolactone, polyorthoester, polyethylene glycol, poly terephthalate, tyrosine, poly(ester amide), polyisobutylene, poly(ethylene terephthalate), polytetrafluoroethylene, polyurethane, polystyrene, polyamide, polyimide, bisphenol-alpha-glycidyl methacrylate, triethyleneglycol dimethacrylate, hydroxyethyl methacrylate, poly-p-chloroxylylene, phenolic resins, and the like.

In some cases, the different stiffness along the vascular graft connectors 2813, 2815 may be provided by having a material forming the connector more proximal to the blood inlet 2812 or the blood outlet 2814 that is stiffer than the material forming the distal portions of the connector. In some cases, the vascular graft connectors may include ribbing to provide structural reinforcement, and the density of the ribbing may be higher more proximal to the blood inlet or the blood outlet than the density of the ribbing at more distal portions.

In some embodiments, the system further includes a bioreactor containing cells configured to receive retentate (i.e., blood that has been passed over a filter medium, such as a silicon nanopore membrane) and/or filtrate from the parallel plate hemofiltration device, and to return components of the filtrate to the blood before the blood is returned to the individual's circulation. The cells may express or provide one or more desired factors to a filtered blood that is to be returned to the individual. Suitable bioreactor systems are described in, e.g., US 20090131858, which is incorporated herein by reference. In some cases, a bioartificial kidney includes a parallel plate device of the present disclosure functionally connected to a bioreactor.

A variety of cells may be used in the bioreactor. In some embodiments the cells of the bioreactor are liver, duodenal, intestinal, gastric, pancreatic, thyroid, parathyroid, adrenal, gonadal, pituitary, or hypothalamic cells. In some embodiments the cells of the bioreactor are bone marrow cells. In other embodiments the cells of the bioreactor are stem cells, feeder cells, or other precursor cells. In still other embodiments, the cells of the bioreactor are derived from stem or precursor cells. In still other embodiments, the bioreactor comprises cells that induce the differentiation of nearby cells or attract nearby cells to the organ. In some embodiments, the cells comprise one or more transgenes (e.g., having inducible promoters).

In some embodiments, the cells of the bioreactor are from kidney or associated tissue, such as renal proximal tubule cells. These cells may replace the metabolic, endocrine, and immunologic functions of a damaged kidney. Renal proximal tubule cells may be grown on an appropriate surface in the bioreactor and then exposed to ultrafiltrate. The cell-exposed ultrafiltrate is then returned to the individual. The cell-exposed ultrafiltrate may contain serum and appropriate levels of desired biological components (e.g., 1,25 dihydroxyvitamin D3, sodium, glucose, etc.).

Methods

Methods of Making a Parallel Plate Hemofiltration/Hemodialysis Device

Also provided herein is a method of making a parallel plate device, as described above. The method may generally include stacking a plurality of plate subunits in an aligned orientation to form a stack; capping each outer-most plate subunit of the stack with a cover plate, to form a parallel plate assembly; and attaching a blood conduit adaptor to an end of the parallel plate assembly.

The number of plate subunits may be any suitable number. In some cases, the number of stacked plate subunits is 2 or more, e.g., 3 or more, 4 or more, 5 or more, 7 or more, 10 or more, 15 or more, 20 or more, including 25 or more, and in some cases, is 50 or less, e.g., 40 or less, 35 or less, 30 or less, including 25 or less. In some embodiments, the number of stacked plate subunits is from 2 to 50, e.g., from 2 to 40, from 3 to 35, from 5 to 35, from 10 to 35, including from 15 to 30.

In some cases, attaching the blood conduit adaptor to an end of the parallel plate assembly includes adding a spacer between the adaptor and the end of the parallel plate assembly.

The components of the parallel plate device may be held together using any suitable method. In some cases, the parallel plate assembly is secured together using screws that extend through screw holes in the frame of the plate subunits and in the cover plates and tightening the cover plates together. In some cases, the plate subunits are attached to each other using a suitable adhesive. In some embodiments, the blood conduit adaptor is attached to the parallel plate assembly using screws.

The present method may further include sterilizing one or more components of the parallel plate device before assembly. Any suitable method of sterilizing may be used for components that are not surface modified. Suitable methods of sterilization include, without limitation, autoclaving (e.g., using a standard dry cycle of about 100° C. to about 140° C., for a duration of about 20 minutes to about 60 minutes), exposing to dry heat (e.g., using a temperature of about 140° C. to about 200° C., for a duration of about 60 minutes to about 180 minutes), treating with ethylene oxide (e.g., exposing to ethylene oxide for from 1 hr to 3 hrs, at a temperature of from about 50° C. to about 60° C., at a pressure of about 100 mmBar to about 150 mmBar), treating with hydrogen peroxide (e.g., using Sterrad® using standard protocols) and exposing to x-ray (e.g., a radiation dose of 20-30 kGy).

For sterilizing the plate subunits, the sterilization method may be one that maintains desirable surface properties of the silicon nanoporous membranes. Thus, where the silicon nanoporous membranes are surface-modified by, e.g., coating with polyethylene glycol or poly-sulfobetaine methacrylate to reduce protein adsorption thereto, the sterilization method used may be one that has a sufficiently small effect on the surface modification. Thus, in some cases, suitable methods of sterilization for the plate subunits may include exposing to dry heat, treating with ethylene oxide, and treating with hydrogen peroxide. In some cases, a fully assembled parallel plate device may be sterilized by, e.g., autoclaving.

Methods of Using a Parallel Plate Device

Parallel plate devices of the present disclosure, and systems that includes the same, find use in performing hemodialysis and/or hemofiltration. In general terms, a method for hemodialysis may include connecting a blood inlet and a blood outlet of a parallel plate device to an individual's circulatory system such that blood circulates from the circulatory system, through the parallel plate device, and back into the circulatory system; and connecting the filtrate/dialysate inlet and outlet to a dialysate pump, such that dialysate circulates through the parallel plate device. The connection may be made at a suitable point in the circulatory system, such as, without limitation, the renal artery and vein. Thus, in some embodiments, the blood inlet is connected to the renal artery, and the blood outlet is connected to the renal vein. A suitable vascular graft connector, as described above, may be used to connect the blood inlet and outlet to the circulatory system.

In some embodiments, the parallel plate device connected to the circulatory system forms an extracorporeal blood circuit, where the parallel plate device is outside the body of the individual. In some embodiments, the extracorporeal blood circuit does not include a pump for circulating blood from and to the body via the parallel plate device.

In some cases, the present method includes implanting the parallel plate device in the body of the individual. The parallel plate device may be implanted using any suitable surgical means. In some cases, the parallel plate device includes one or more (e.g., two or more, three or more, or four or more) suture tabs, and the device is positioned in an implantation site by suturing the device to a tissue wall of the implantation site via the suture tabs. In some embodiments, the parallel plate device is enveloped in a biocompatible mesh (e.g., polymeric mesh, such as a polypropylene mesh), and the device is positioned in an implantation site by suturing the device to a tissue wall of the implantation site via the mesh.

Hemofiltration may be achieved using methods as described above, where the filtrate/dialysate inlet is blocked and the filtrate/dialysate outlet is connected to a waste reservoir (e.g., bladder or an extracorporeal waste receptacle).

Kits

Also provided herein are kits that find use in performing hemofiltration and/or hemodialysis using a parallel plate device, as described herein. The present kit may include a parallel plate device of the present disclosure.

The present kit may include any other suitable components for performing hemofiltration and/or hemodialysis, as described herein. In some embodiments, the kit includes one or more vascular graft connectors with or without adaptors for connecting to the blood inlet or outlet of the parallel plate device. In some embodiments, the kit includes one or more polymeric sleeves (e.g., silicone sleeves) for reinforcing the vascular graft connectors.

Components of a subject kit can be in separate containers; or can be combined in a single container. The kit may further include a suitable packaging for holding the parallel plate device and one or more other components, as described above. Any one or more, or all components of the present kit may be substantially sterile.

In some cases, the present kit includes instructions for using the implantable, parallel plate device. The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, digital versatile disc (DVD), flash drive, Blue-ray Disc™ etc. In yet other embodiments, the actual instructions are not present in the kit, but methods for obtaining the instructions from a remote source, e.g. via the internet, are provided. An example of this embodiment is a kit that includes a web address where the instructions can be viewed and/or from which the instructions can be downloaded. As with the instructions, the methods for obtaining the instructions are recorded on a suitable substrate.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

EXAMPLES

The following examples are put forth so as to provide those of ordinary skill in the art with a complete disclosure and description of how to make and use the disclosed subject matter, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Figure 17:
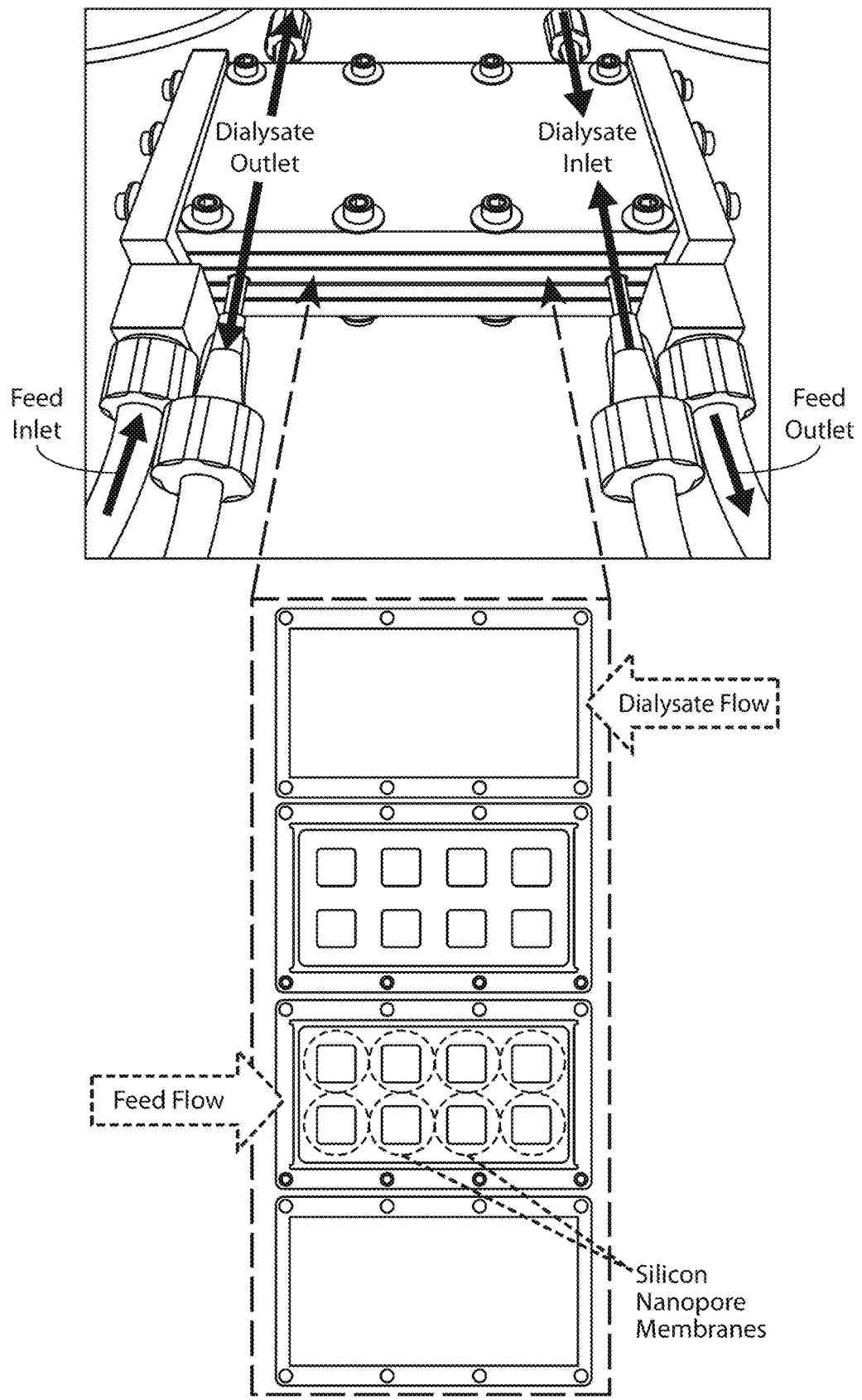
FIG. 17 is a drawing depicting a parallel plate device containing silicon nanoporous membranes, according to embodiments of the present disclosure.

Example 1: Preliminary Diffusive Clearance of Silicon Nanoporous Membranes in a Parallel Plate Configuration for Renal Replacement Therapy Materials and Methods
Membrane Fabrications Silicon nanoporous membranes (SNMs) were fabricated using previously described microfabrication techniques. Membranes were composed of a 300 nm polysilicon layer with an array of rectangular pore slits measuring 4.5 μm×10 nm. The structural support layer was composed of <100>-oriented, n-type crystalline silicon with 400 μm thickness. Wafers were diced into 10×10 mm chips with an effective membrane area of 0.216 cm$^2$. The hydraulic permeability of SNM was tested to verify membrane integrity and determine pore size 12.
Surface Modification Polyethylene glycol (PEG) surface modification was performed on polysilicon surfaces. Briefly, SNM were treated with a 3:1 sulfuric acid to hydrogen peroxide (Piranha) solution to functionalize the polysilicon surface with hydroxyl groups. Membranes were submersed in 25 ml of toluene and 285 μL of PEG-silane (Sigma Aldrich, St. Louis Mo.) at 70° C. for 2 hours. Surface modified membranes were then rinsed at 10 minutes intervals (3×) with toluene (Gelest Morrisville, Pa.), ethanol, and deionized water. Hydraulic permeability was retested following PEG coating to measure the pore size change after surface modification. SNM coating thickness was sub-5 nm.
Parallel Plate Array Flow Cell A two-channel parallel plate flow cell capable of housing and testing multiple SNM chips exposed to blood flow was developed (FIG. 17). It included two titanium (grade 2 commercially pure) inlet and outlet ports, which were positioned perpendicular to the plates for even fluid distribution. The main body of the device included a stacked set of parallel plates (titanium, grade 2 commercially pure), with alternating channels for blood (internal part of each plate) and dialysate flow (in the interfaces between the plates). A single internal blood channel was 60 mm×30 mm×2.4 mm (l×w×h) and defined by: a top plate (solid silicon sheet, 6×3 cm), and bottom plate (8 SNM or solid silicon mounted into the titanium holder with polydimethylsiloxane). The plates were sealed together using high purity silicone gaskets and screws to prevent leakage. Dialysate flow was split into two inlet ports and two outlet ports on the center plate. Uniform dialysate flow in a counter-current direction was achieved via an array of multiple 1 mm diameter channels across the width of the dialysate plate. The dialysate channel was defined by the height of the compressed gasket (0.4 mm) with length of 60 mm and width of 30 mm. The titanium end caps were machined by Hayes Manufacturing Services (Sunnyvale, Calif.) and the remaining components were machined in-house. SolidWorks® software (DS Solidworks, Waltham, Mass.) was used to design all components.
Mechanical Testing Mechanical robustness of SNM were tested at a range of pressures (1448 mmHg) using a syringe pump (KD410, KDS Scientific, Holliston, Mass.) and pressure gauge (DPI 104 30 psi, GE Druck, Leicester, UK). Pressure was ramped at 25.9 mmHg until membrane rupture or 1448 mmHg was reached (n=11).

Static and dynamic leak testing of the parallel plate array was conducted over a range of differential pressures (0-200 mmHg). Pressure drop across the array (inlet to outlet) was measured over a range of flow rates (0-200 ml/min). A Masterflex L/S Digital Drive Peristaltic Pump, (MK-07551-00, Cole Parmer, Vernon Hills, Ill.) was used to drive flow and pressure in the system was monitored using two pressure gauges (DPI 104 10 psi, GE Druck, Leicester, UK) (FIG. 23).

Figure 23:
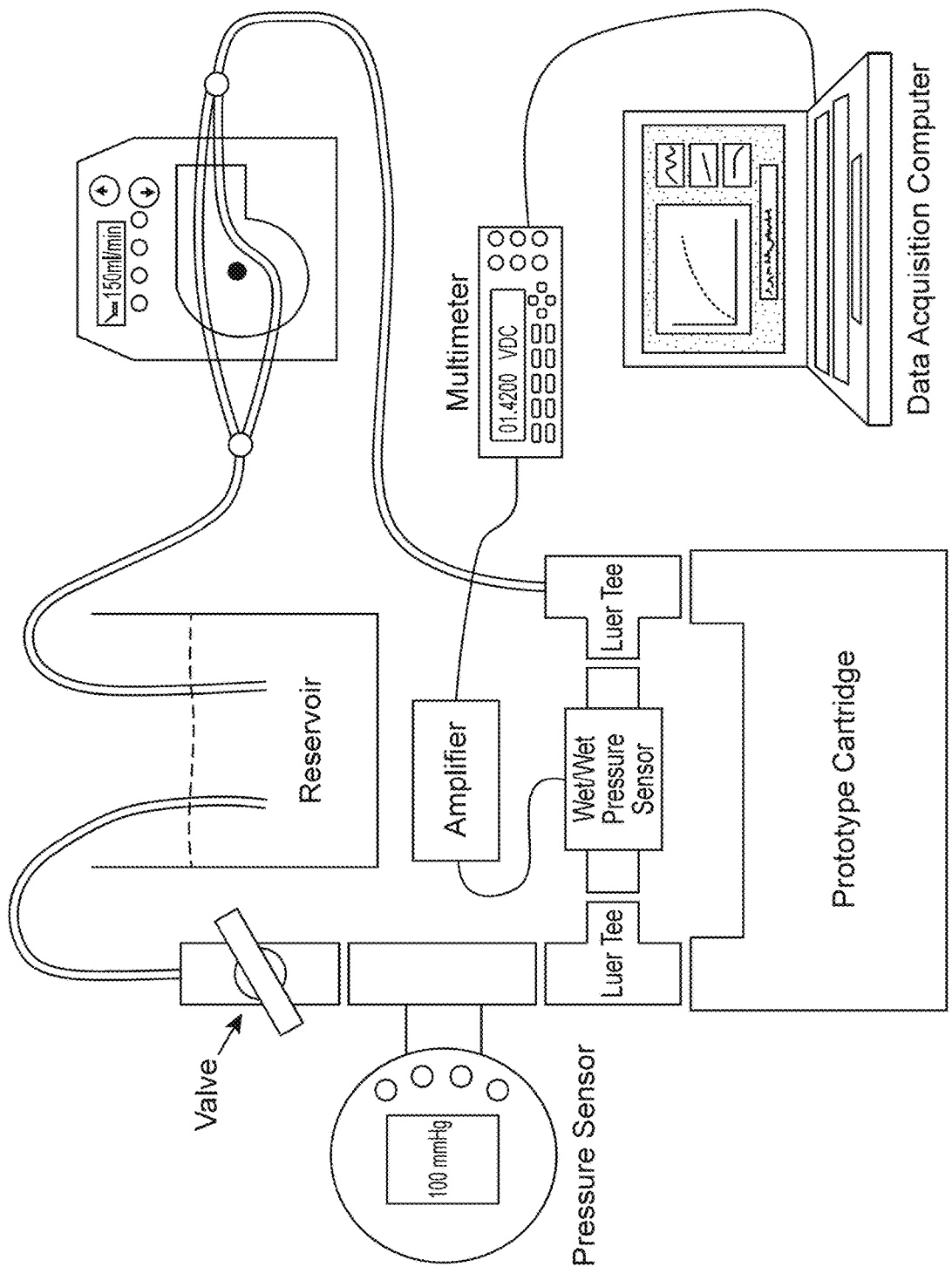
FIG. 23 is a schematic diagram showing a bench-top pressure testing setup for a parallel plate hemofiltration device, according to embodiments of the present disclosure.

FIG. 23. Schematic of a bench-top pressure testing setup. Water is pumped from the reservoir through the parallel plate flow cell. Pressure is measured across the flow cell, amplified, and recorded.
Parallel Plate Array Diffusive Clearance Eight PEG coated SNM chips were mounted onto the blood channel plate of the flow cell. The average pore size of the SNM was 6.5 nm±0.6 and the combined effective membrane surface area was 1.73 cm2. The albumin solution consisted of creatinine 10 mg/dL (Acros Organics, Geel, Belgium), 88 mg/dL blood urea nitrogen (Fisher Scientific, Waltham, Mass.), 5 mg/dL phosphorus (Sigma, St. Louis, Mo.), and 3 g/dL albumin (Sigma, St. Louis, Mo.) in Millipore water (Millipore, Billerica, Mass.) in a volume of 13 ml. Whole blood diffusion experiments were conducted using 30 ml of heparinized (20 units/ml) bovine whole blood (Lampire Biological Laboratories, Pipersville, Pa.). The albumin solution or whole blood was recirculated and 1 L of dialysate (140 mEq of NaCl) was recirculated in a counter-current fashion (FIG. 17). The flow rates for both solutions were set to 25 ml/min using a peristaltic pump to maintain pressures of <30 mmHg and limit transmembrane pressures. The system was preconditioned with the solutions for 30 minutes. Samples of albumin solution or whole blood and dialysate were collected at 0, 2, and 5 hours (n=3). The whole blood experiments were also conducted for 24 hours (n=2). The flow cell was disassembled and evaluated for thrombus formation, membrane fracture, or leaks. The concentrations of the different solutes were measured using an Avida 1800 Chemistry System (Siemens Medical, Erlangen, Germany) at San Francisco General Hospital (San Francisco, Calif.). Solute clearance (K) was calculated by fitting concentrations measured at serial time points an exponential decay function: $C(t)=C_i e^{-Kt/V}$, where C(t) was the concentration at time t, $C_i$ was the initial concentration, t was the time, and V was the volume.

FIG. 17. Assembled parallel plate array with blood inlet/outlet and counter current dialysate inlet/outlet. The stacked parallel plates are shown below with 8 silicon nanoporous membranes outlined in red and 8 solid silicon chips (not outlined). The arrows indicate the flow inlet and direction of the feed and dialysate, respectively.

Extracorporeal Porcine Experiment

Pumpless blood flow characteristic in a parallel plate SNM array within an extracorporeal blood circuit was evaluated in a pig for four hours with University of California, San Francisco Institutional Animal Care and Use Committee approval. A ~20 kg Yorkshire pig was anesthetized and systematic heparin anticoagulation therapy was delivered in bolus (200 IU/kg) followed by continuous infusion (125 IU/kg/hr). The renal artery and vein were cannulated using ultrasound and fluoroscopic guidance, with two single lumen catheters (Deltec Ventra Long-term Central Venous Catheters, Single-Lumen, 9FR, PN 21-2368-01, Smiths Medical, Dublin, Ohio). The inlet of the flow cell was attached to the arterial catheter and outlet was attached to the venous catheter, completing the extracorporeal arterio-venous circuit. Several minutes after the experiment began, a fluoroscopic contrast agent (Omnipaque 300, GE Healthcare, Little Chalfont, UK) was injected. Cine images were obtained during a 90-second dynamic infusion of contrast. Gross qualitative flow through the device was evaluated.

The extracorporeal circuit was run for a total of four hours uninterrupted. At the end of the experiment, with the device still attached, a second bolus of contrast agent was delivered and the device was re-imaged. The contrast front was again visualized flowing across the device. The arterial and venous catheters were then clamped and the device was disconnected from the extracorporeal circuit and drained. In order to prevent the remaining stagnant blood from coagulating, the cartridge was immediately cleared with heparinized saline until it ran clear. It was fully drained and then primed with a solution of 4% paraformaldehyde and deionized water. The device was carefully disassembled in order to examine the device for thrombus formation and leakage.

Cell and Protein Adhesion Studies

Scanning Electron Microscopy (SEM)

The SNM were placed in a solution containing 2% glutaraldehyde (Electron Microscopy Sciences, Fort Washington, Pa.), 3% sucrose (Sigma-Aldrich, St. Louis, Mo.) and 0.1 M of phosphate buffered saline (PBS) at 4° C. and pH 7.4. After 1 h, the substrates were rinsed twice with PBS for 30 min at 4° C. and washed with distilled water for 5 minutes. Dehydration was achieved by placing the substrates in 50% ethanol for 15 minutes while increasing the concentration of ethanol to 60, 70, 80, 90 and finally 100%. Dehydrated samples were then mounted on aluminum stubs, sputter-coated with gold-palladium, and examined using SEM (Ultra55 FEGSEM, ZEISS, Peabody, Mass.).

Immunohistochemistry (IHC)

Platelet adhesion and activation was assessed using immunofluorescence staining for the platelet marker, CD41 (Abcam, Cambridge, Mass.), and blood clot marker, tissue plasminogen activator (t-PA, Abcam, Cambridge, Mass.). Platelets were fixed in 4% paraformaldehyde (Fisher Scientific, Waltham, Mass.) for 15 minutes followed by incubation in 1% bovine serum albumin for 30 minutes to block nonspecific binding. Platelets were double-labeled as follows: substrates were first incubated with primary antibodies (t-PA), diluted 1:50 in PBS for 60 minutes followed by Alexa Fluor 546 donkey anti-mouse antibody (Invitrogen, Carlsbad, Calif.) diluted 1:100 in PBS for 60 minutes. Finally the samples were incubated with anti-human CD41 fluorescein isothiocyanate labeled mouse monoclonal antibody diluted 1:300 in PBS for 60 min. Four images were acquired per replicate using a Nikon Eclipse Ti-E motorized inverted microscope (Nikon Instruments INC., Melville, N.Y.) to obtain a total of 12 images per substrate. The fluorescent intensity of the images was quantified using ImageJ.

Results

Mechanical Testing

All SNM withstood mechanical pressure testing greater than 775.7 mmHg Four out of eleven SNM failed with an average pressure of 910.2±51.7 mmHg and the remaining seven SNM remained intact up to 1448 mmHg. The parallel plate array was tested at varying flow rates up to 200 ml/min without leakage of fluid out of the assembled device or between the individual parallel plates. The measured pressure drop across the flow cell at a flow rate of 200 ml/min was 4.6 mmHg (FIG. 24).

Figure 24:
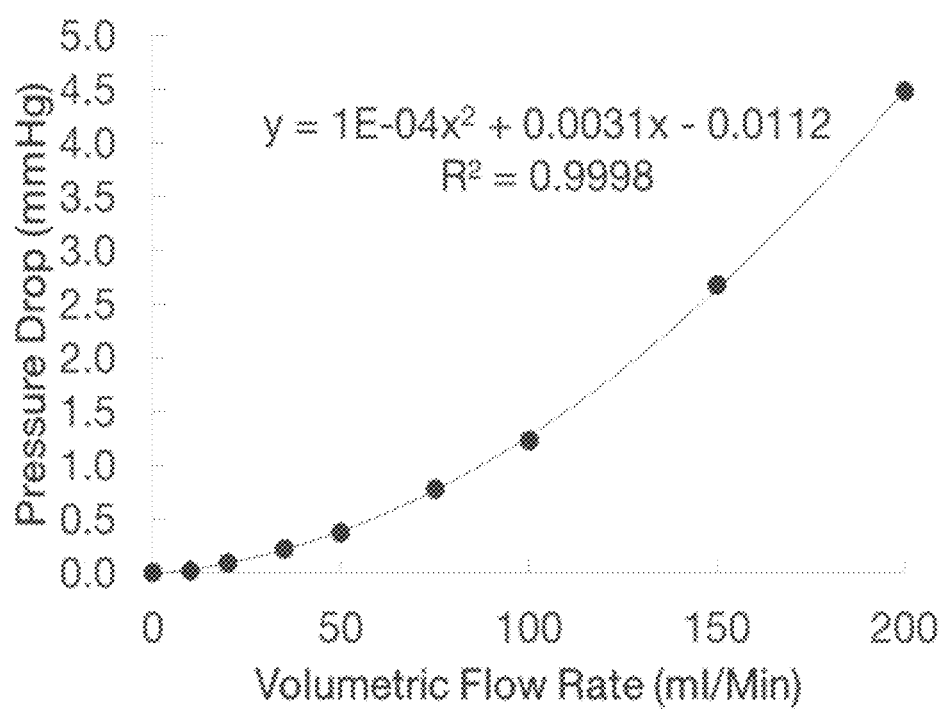
FIG. 24 is a graph showing ΔP vs. flow rate across a parallel plate device measured using water, according to embodiments of the present disclosure.
Figure 25A:
FIGS. 25A and 25B are a collection of images showing an implanted parallel plate device connected to a circulatory system via silicone sleeve-reinforced vascular graft connectors, according to embodiments of the present disclosure.
Figure 25B:
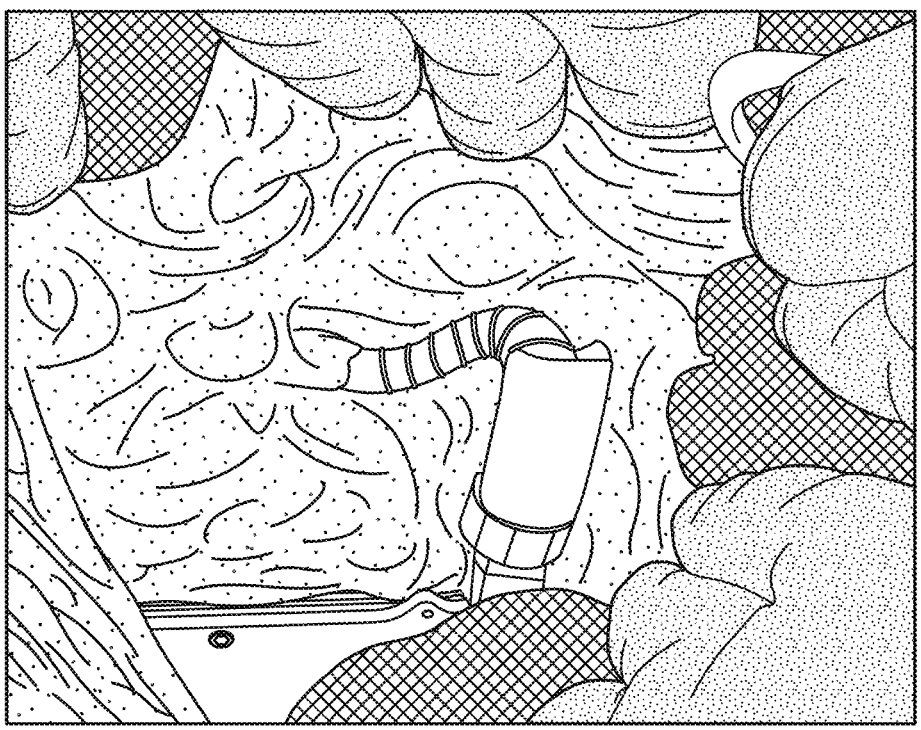
Figure 27A:
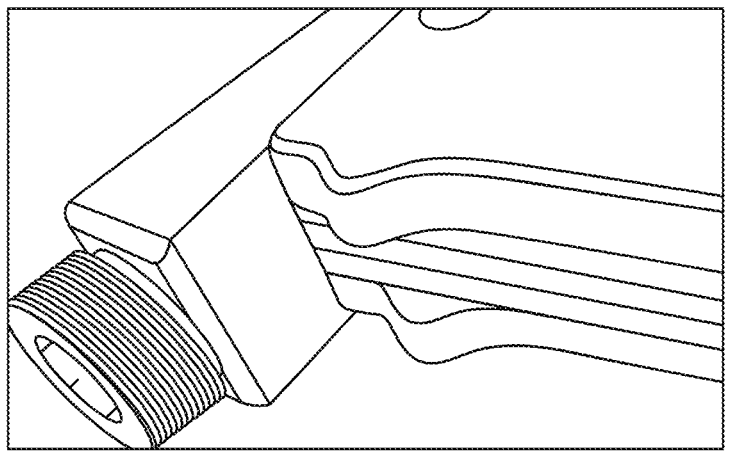
FIGS. 27A-27C are a collection of images showing an implanted parallel plate device anchored to an implantation site through suture tabs, according to embodiments of the present disclosure.
Figure 27B:
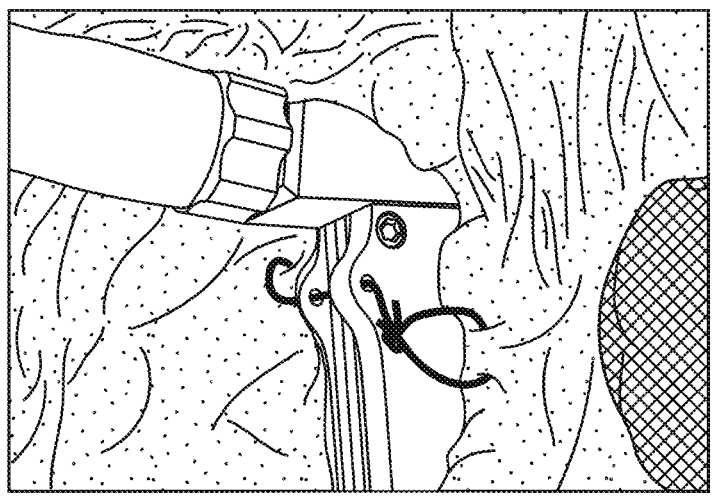
Figure 27C:
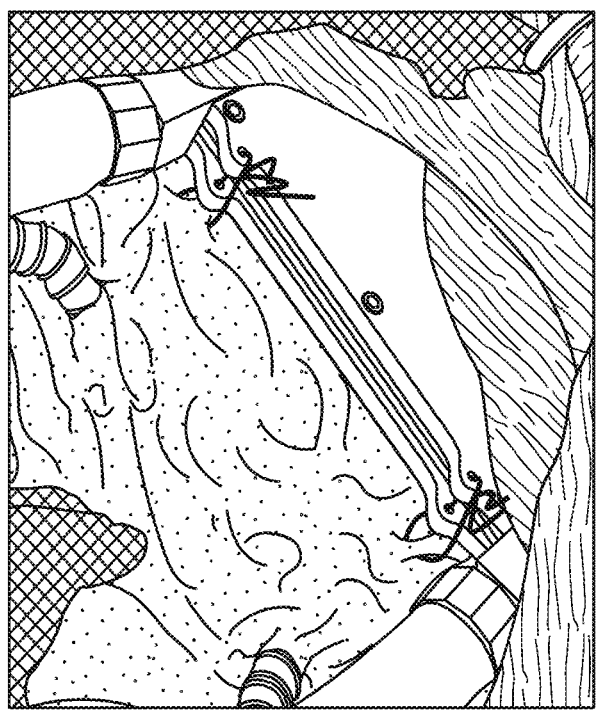

FIG. 24. DP vs. flow rate across the parallel plate flow cell using water.

Diffusive Clearance of SNM Parallel Plate Array

The change in concentration using single-pass measurements was below the level of detection due to the high flow rate indicating that diffusive clearance was no longer dependent on flow rate. Recirculated albumin solution and whole blood concentrations of creatinine, urea and phosphorus followed an exponential decay function characteristic of diffusive clearance. The clearance (K) normalized to SNM surface area for albumin solution and whole blood experiments are shown in Table 1. The initial albumin concentration was 3.17 g/dL±0.05 and 5-hour albumin concentration was 3.13 g/dL±0.12. There was no significant reduction in albumin concentration (p<0.05). Overall, heparinized bovine whole blood experiments showed maintenance of diffusive clearance similar to albumin solution. There was no evidence of clot formation during the 2 and 5 hour collection times. However, there was visible clot formation within the blood reservoir after 24 hours. Upon disassembly of the device, it was found there were no gross thrombi or membrane occlusion after 24 hours of continuous blood circulation (FIGS. 21 and 22).

Figure 21:
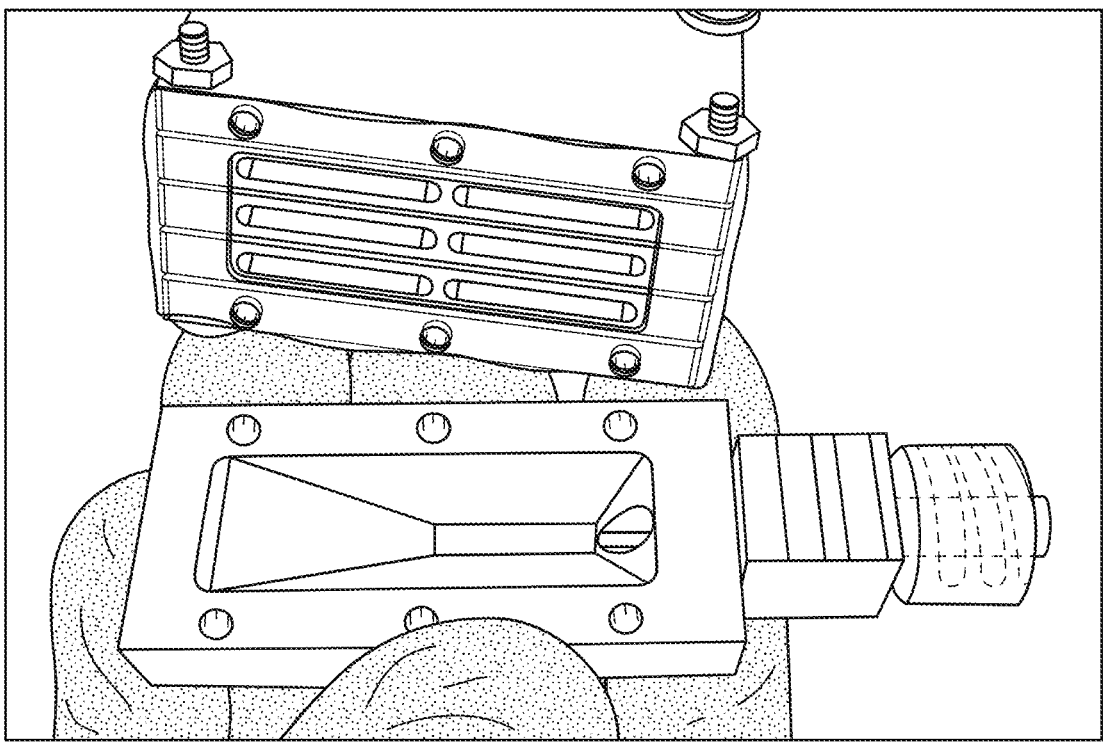
FIG. 21 is an image showing an inlet of a parallel plate device after exposure to blood in an extra-corporeal porcine study, according to embodiments of the present disclosure.

FIG. 21. Inlet of flow cell after 4 hours of blood exposure in an extra-corporeal porcine study. There was no visible clot formation observed upon disassembly.

Figure 22:
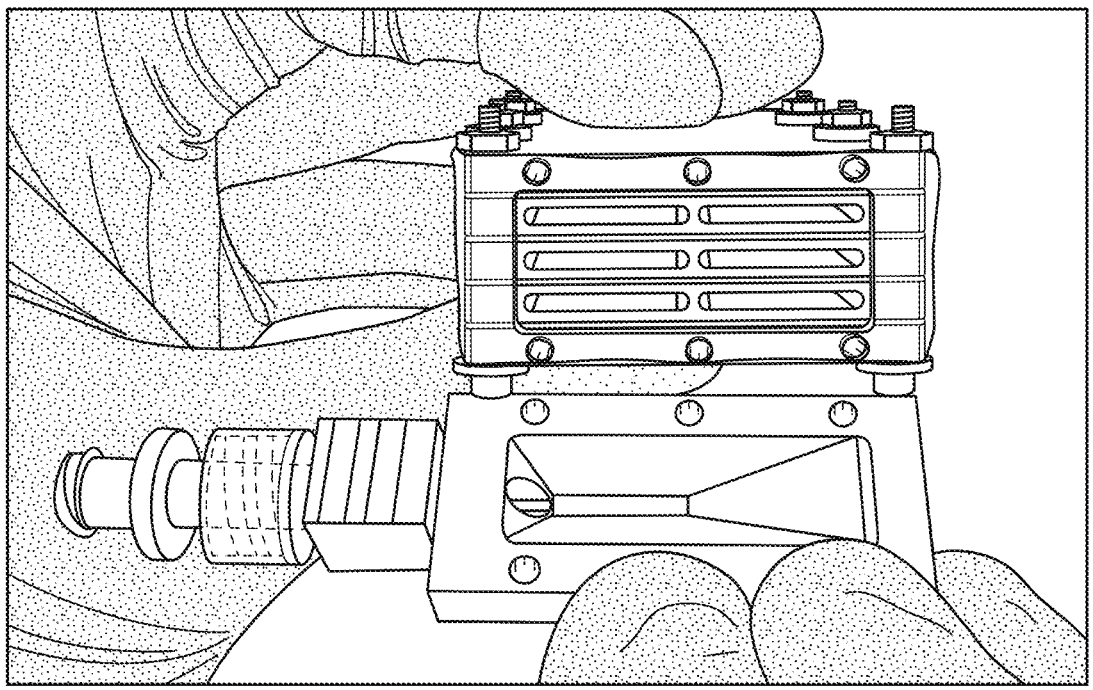
FIG. 22 is an image showing an outlet of a parallel plate device after exposure to blood in an extra-corporeal porcine study, according to embodiments of the present disclosure.

FIG. 22. Outlet of flow cell after 4 hours of blood exposure in an extra-corporeal porcine study. There was no visible clot formation observed upon disassembly.

TABLE 1

Clearance (K) for creatinine, urea, and phosphorus in albumin solution and whole blood.

| | Diffusive Clearance (ml/min/m$^2$) | |
| --- | --- | --- |
| | Parallel Plate Array (Albumin Solution) | Parallel Plate Array (Whole Blood) |
| Creatinine | 84.0 ± 15.3 | 127.6 ± 14.0 |
| Urea | 115.2 ± 17.8 | 117.1 ± 16.0 |
| PO4 | 64.2 ± 14.7 | 56.5 ± 9.6 |

Porcine Extracorporeal Circuit

The preliminary extracorporeal circuit (FIG. 18A) study demonstrated pumpless blood flow through the parallel plate array without complications. The pig tolerated the device well and did not exhibit deterioration of hemodynamic parameters or clinical status. The fluoroscopy images obtained at the start and end of the 4-hour experiment showed no degradation in flow characteristics, with uniform blood flow across the parallel plates (FIG. 18B). There was no evidence of thrombus formation in the cannulated vessels or catheter. Disassembly of the device showed no visible thrombi or debris within the flow cell.

Figure 18A:
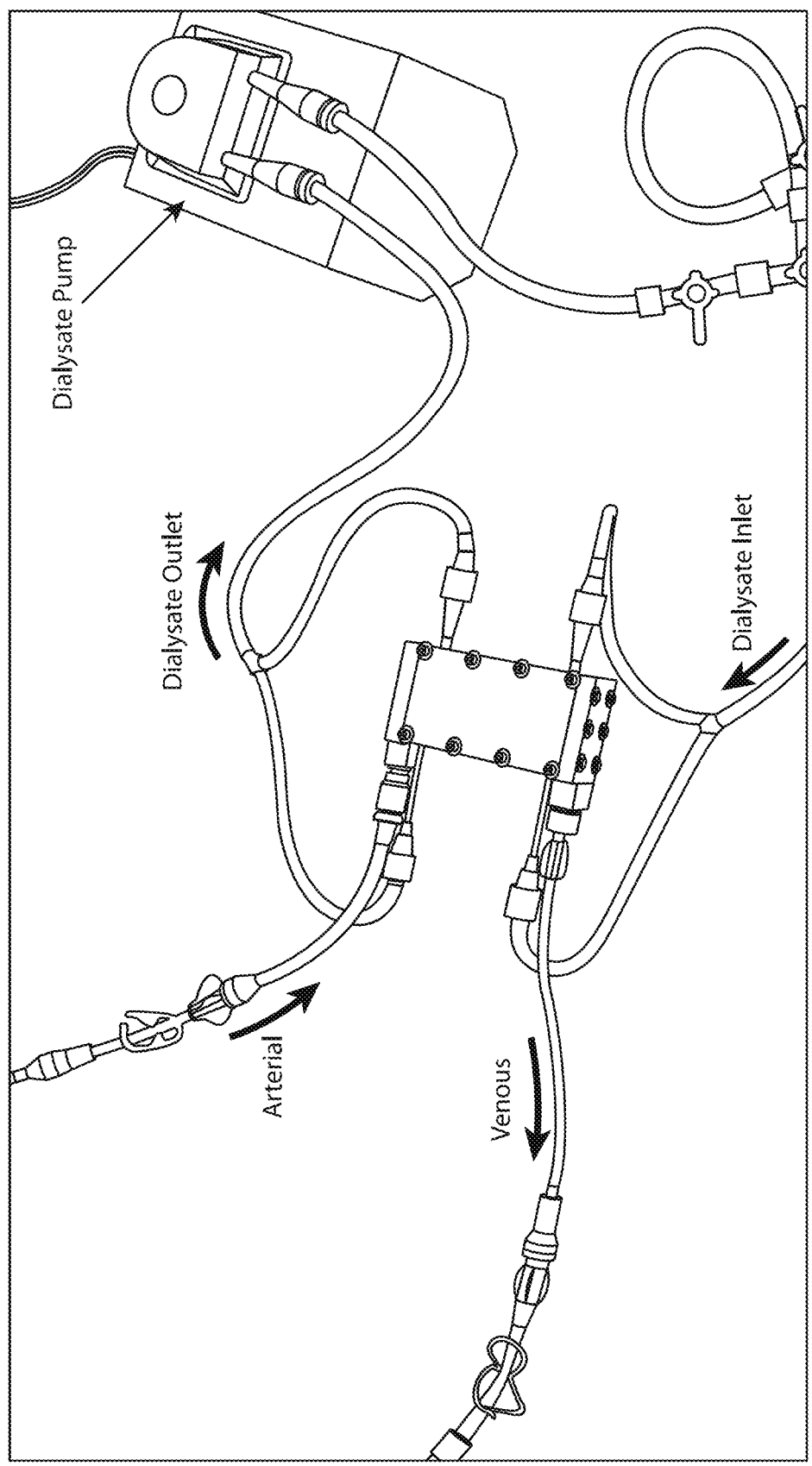
FIGS. 18A and 18B are a collection of drawings and images showing an ex vivo operating parallel plate device, according to embodiments of the present disclosure.
Figure 18B:
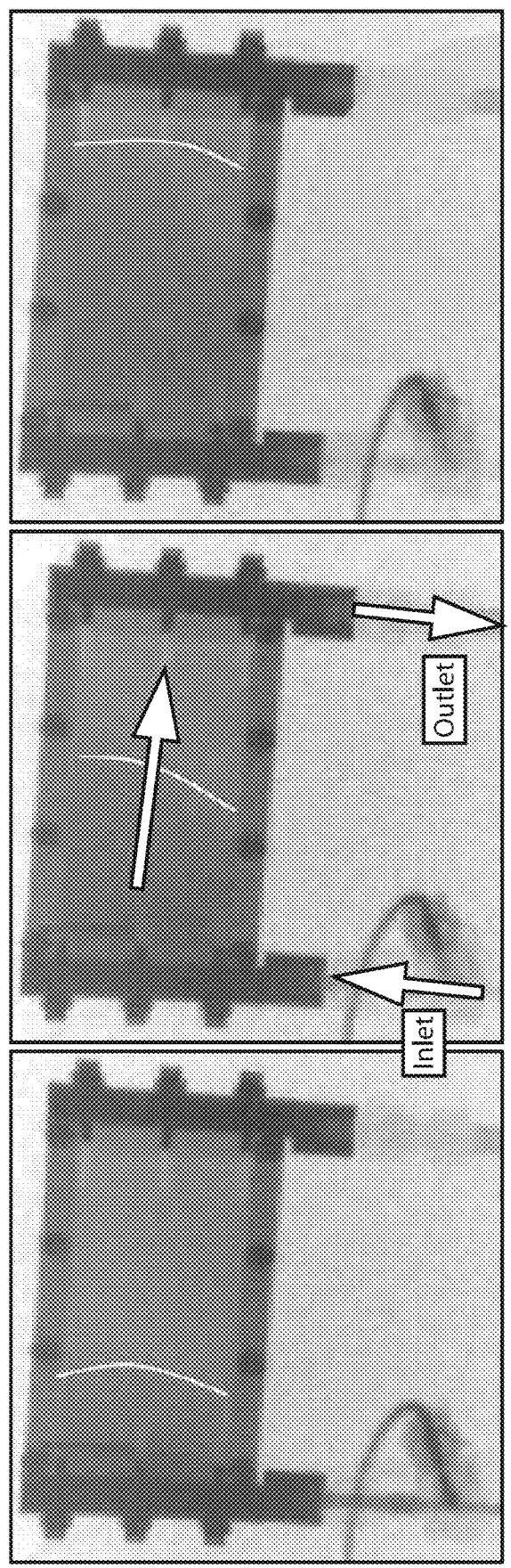

FIG. 18A. Ex vivo porcine experiment. Arterial and venous inlet and outlet labeled with arrows indicating the direction of flow. Dialysate inlet and outlet with arrows indicating the countercurrent flow of dialysate.

FIG. 18B. Fluoroscopy time-lapse images (Top down view). Cine images were obtained following a 90 s dynamic infusion of contrast. Representative images at the start, middle and end of contrast infusion are shown. White lines are labeled to indicate contrast front. Black arrows show direction for blood flow.

Hemocompatibility Assessment

Figure 19:
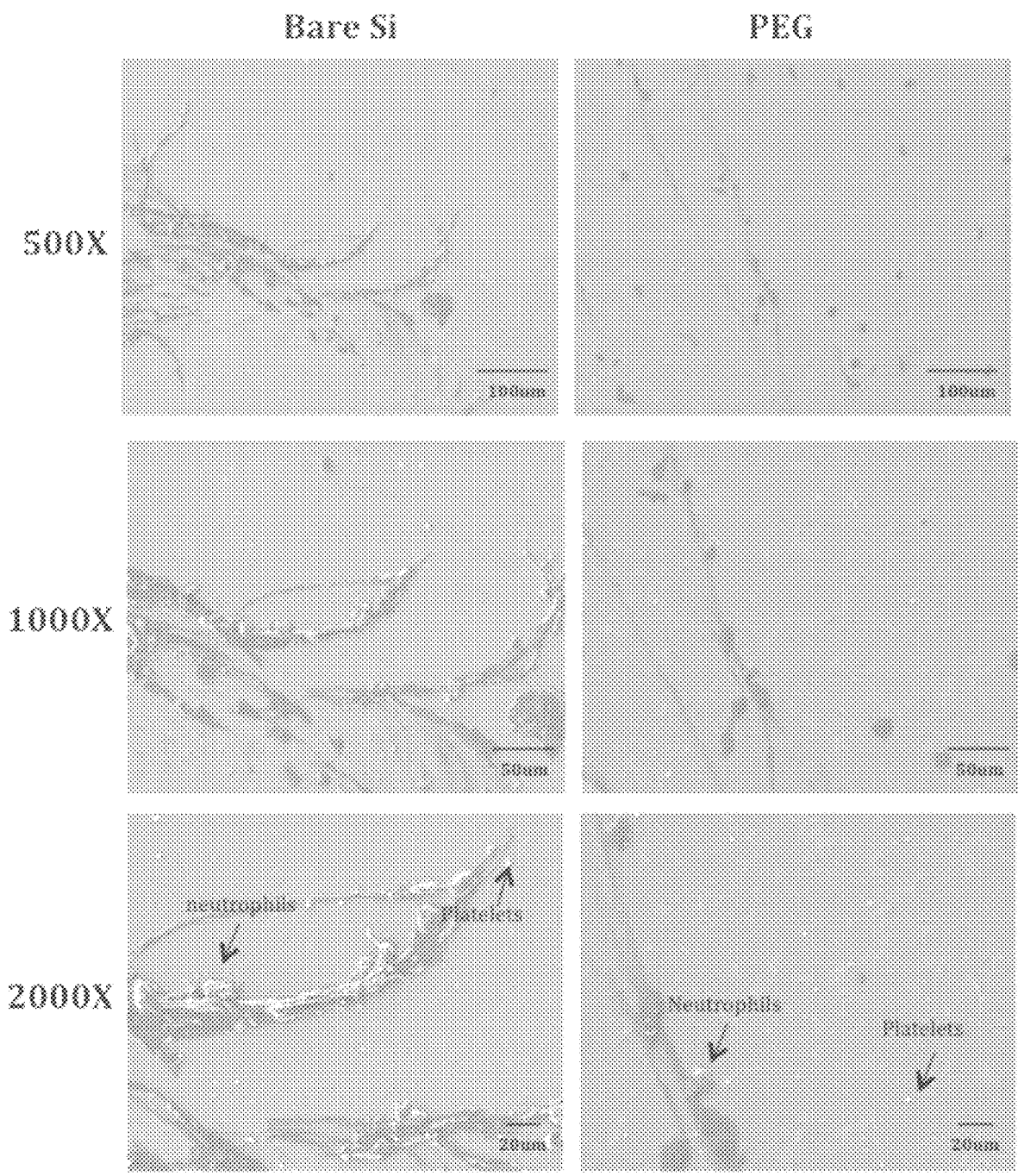
FIG. 19 is a collection of scanning electron micrography (SEM) images showing adhesion of blood cells on silicon substrates, according to embodiments of the present disclosure.
Figure 20:
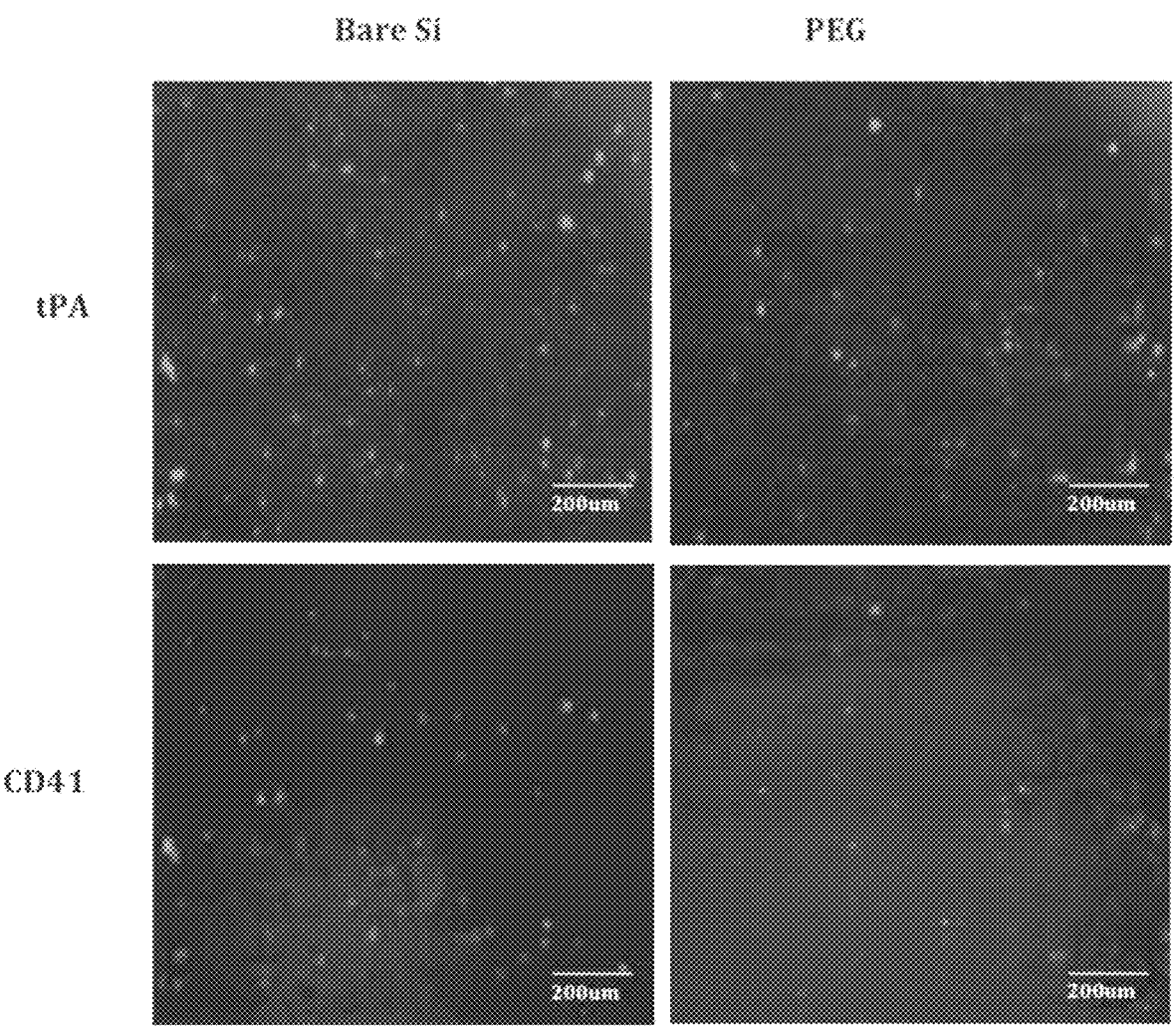
FIG. 20 is a collection of images showing adhesion of blood components to silicon substrates, according to embodiments of the present disclosure.

Following disassembly of the flow cell, the silicon was imaged by SEM. There was cell adhesion on blood-exposed surfaces for both uncoated silicon and PEG-coated silicon. However, there was visually less platelet and neutrophil adhesion on the surface of PEG-coated silicon compared to bare silicon (FIG. 19). Representative images showing platelet adhesion and blood clots were visualized by immunofluorescence staining for CD41 and t-PA on uncoated silicon and PEG-coated silicon surfaces (FIG. 20). Total fluorescent intensity was used to quantify the amount of staining on the surface. Bare silicon surfaces had a 4.1-fold increase in fluorescent intensity for t-PA and a 1.8-fold increase in fluorescent intensity for CD41 compared to PEG coated surfaces.

FIG. 19. SEM images showing neutrophils (average sizes: 12-17 μm), platelets (average sizes: 1-6 μm) and red blood cells (average sizes: 8-10 μm) adhesion on bare silicon (Si) and PEG-coated substrates. Thread like structures represents fibrin formation.

FIG. 20. Representative images showing platelet adhesion and blood clots as visualized by immunofluorescence staining for t-PA (in red, blood clotting marker) and CD41 (in green, platelet marker) and on varying substrates after porcine study; bare silicon (Si), PEG-coated substrates (PEG).

Example 2: Surgical Considerations for an Implantable Renal Replacement System

Surgical and clinical factors for pumpless implantable renal replacement system containing silicon nanoporous membranes were explored through the development of an early-stage implantable prototype and subsequent preclinical feasibility testing in a large animal-model.

Methods

An iterative proof-of-concept study was designed to develop the implantation procedure and to evaluate the blood-flow characteristics of the prototype. A swine model was selected because of the comparably sized vasculature and hematologic similarities with humans.

Results

A prototype was fabricated with a 3 mm inlet and outlet, which was divided into three 1 mm high blood channels defined by silicon parallel plates. The titanium-based device was 9.3 cm×5.7 cm×1.4 cm with a dry weight of 189 g. Autoclave was used for sterilization. Dacron (polyester) grafts with titanium connectors served as the blood conduits. Initial implantations were unsuccessful due to thrombosis. The Dacron grafts were not structurally rigid enough to prevent kinking. Moreover, inadequate anchoring and subsequent device shifting subjected the grafts to additional extrinsic forces. Iterative changes included replacing Dacron with a ringed two-layered graft (Polytetrafluoroethylene (PTFE) bonded to polyester) and reinforced with a silicone strain-relieving sleeve (FIGS. 25A-25B, 26A-26B). Sections of the titanium exoskeleton were replaced with Polyether ether ketone (PEEK), which reduced movement of the implant and resulted in a 40% dry-weight reduction. The anticoagulation regimen was modified to include Coumadin with a lovenox-bridge. These changes, along with refinement of the surgical procedure, allowed for successful implantation of the prototype with flow and patency confirmed via fluoroscopy on post-operative day 3.

Example 3: Impact of Sterilization Techniques on Silicon Nanoporous Membranes

Materials and Methods

Solid 1×1 cm silicon chips were coated with polyethylene glycol (PEG) or poly-sulfobetaine methacrylate (pSBMA) and then exposed to one of five sterilization modalities (autoclave (Standard dry cycle, 121° C. for 30 minutes), dry heat (160° C. for 120 minutes), ethylene oxide (EtO; exposure for 2 hours at 132 mBar and 55° C.), hydrogen peroxide (Sterrad®, standard cycle) and x-ray (Radiation dose: 25-26 kGy)). Validation of sterilization was performed with industry standard process control biological indicators for autoclave, dry heat and ethylene oxide sterilizations. Hydrogen peroxide sterilization was confirmed with a chemical indicator. Dosimetry confirmed a delivered dose range of 25-26 kGy for X-ray irradiation. Uncoated and non-sterilized membranes served as controls. The surface coatings were analyzed by contact angle, x-ray photoelectron spectroscopy (XPS), ellipsometry and ELISA for albumin adsorption.

Sterilized surfaces were then analyzed with the following techniques: Water Contact angle; X-ray photoelectron spectroscopy (XPS) for chemical composition; Ellipsometry for surface coating thickness; and Enzyme-linked immunosorbent assay (ELISA) for protein adsorption.

Results

Figure 29:
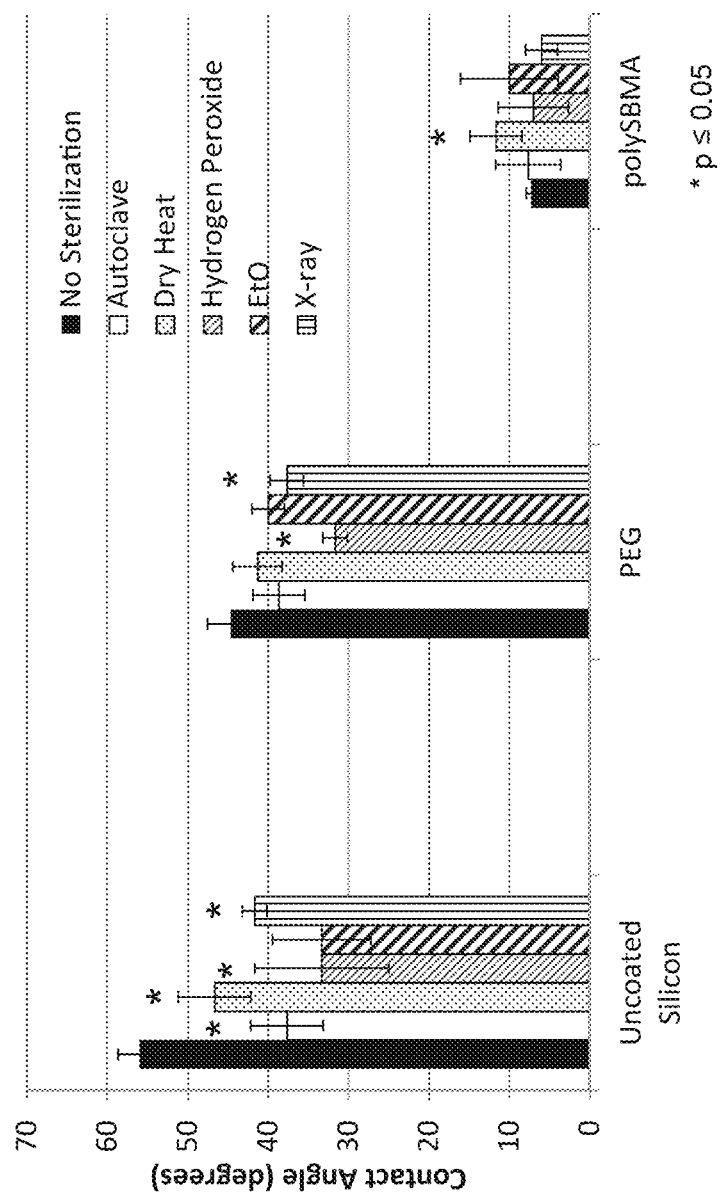
FIG. 29 is a graph showing water contact angle of sterilized coated silicon substrates, according to embodiments of the present disclosure.
Figure 30:
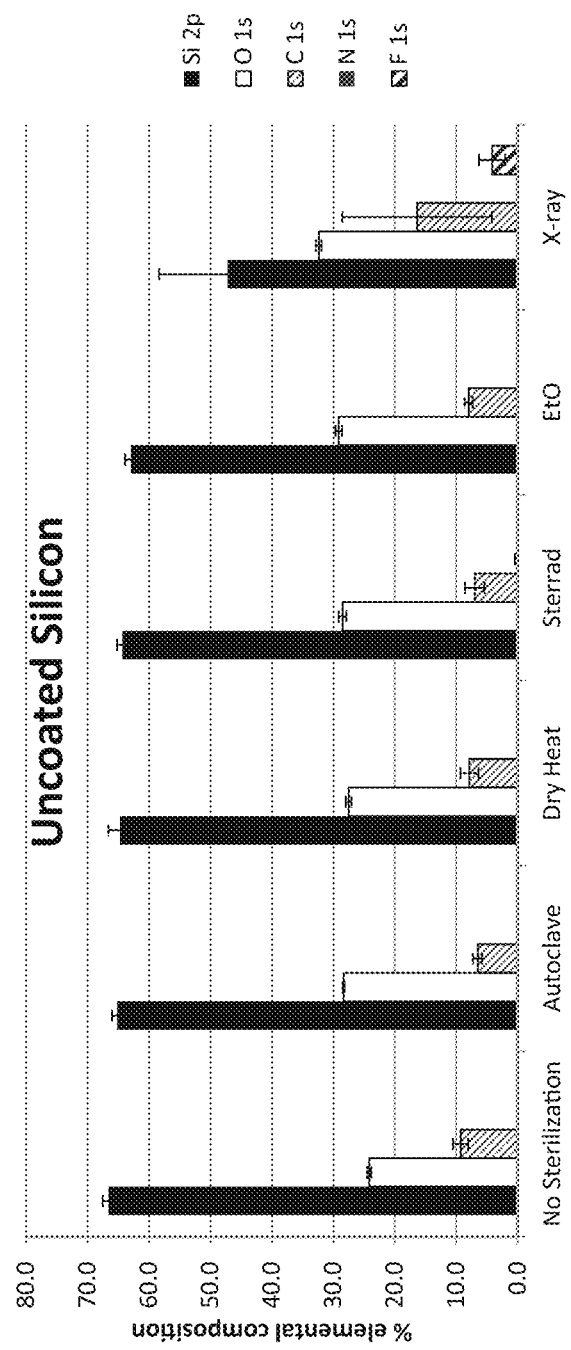
FIG. 30 is a graph showing X-ray photoelectron spectroscopy (XPS) analysis of sterilized uncoated silicon substrates, according to embodiments of the present disclosure.
Figure 31:
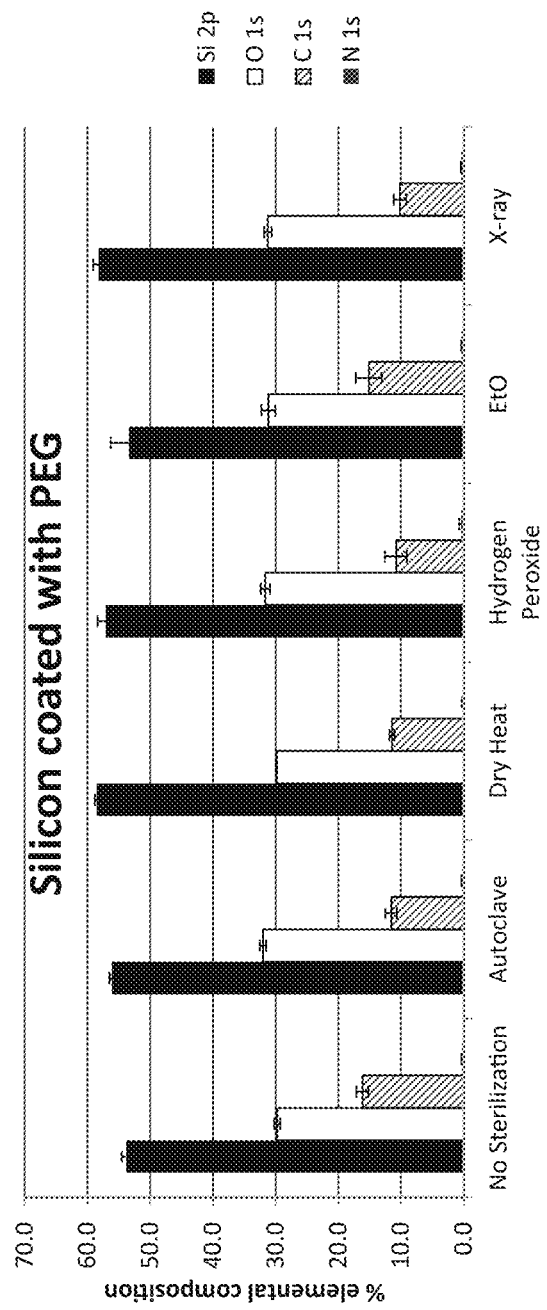
FIG. 31 is a graph showing XPS analysis of sterilized polyethyleneglycol-coated silicon substrates, according to embodiments of the present disclosure.
Figure 32:
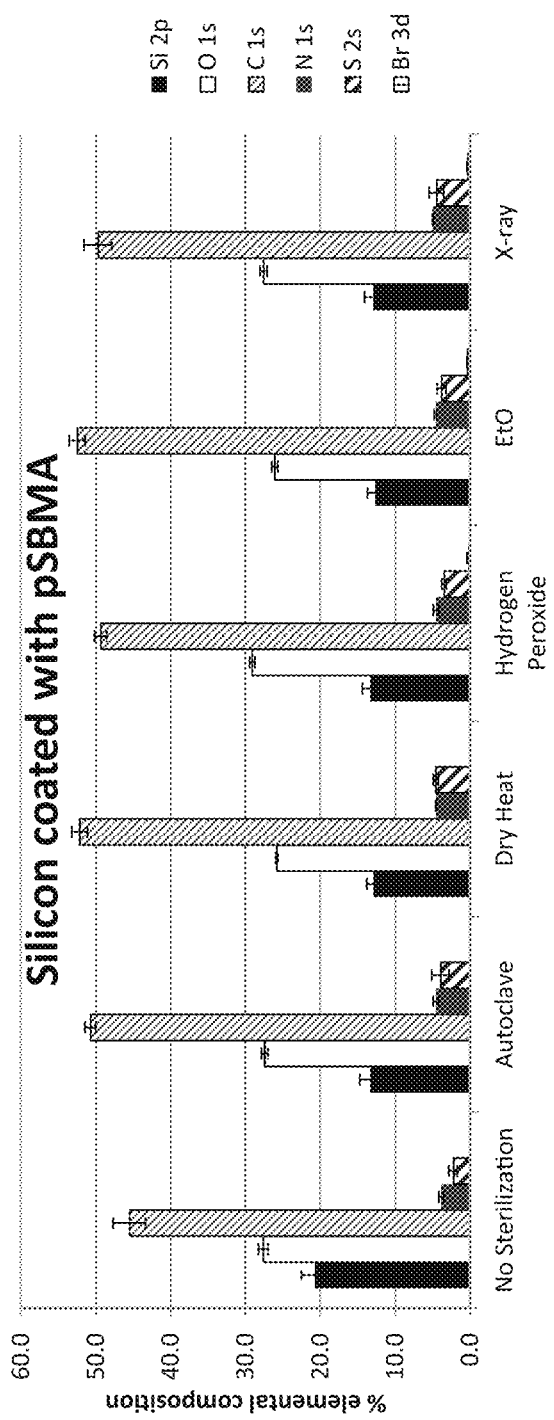
FIG. 32 is a graph showing XPS analysis of sterilized poly-sulfobetaine methacrylate (pSBMA)-coated silicon substrates, according to embodiments of the present disclosure.

After sterilization the presence of PEG and pSBMA was confirmed by contact angle and XPS (FIGS. 30-32). PEG-coated silicon became more hydrophilic (contact angle decreased) after hydrogen peroxide and X-ray irradiation (FIG. 29). Dry heat increased contact angle of pSBMA coated silicon (FIG. 29).

Figure 33:
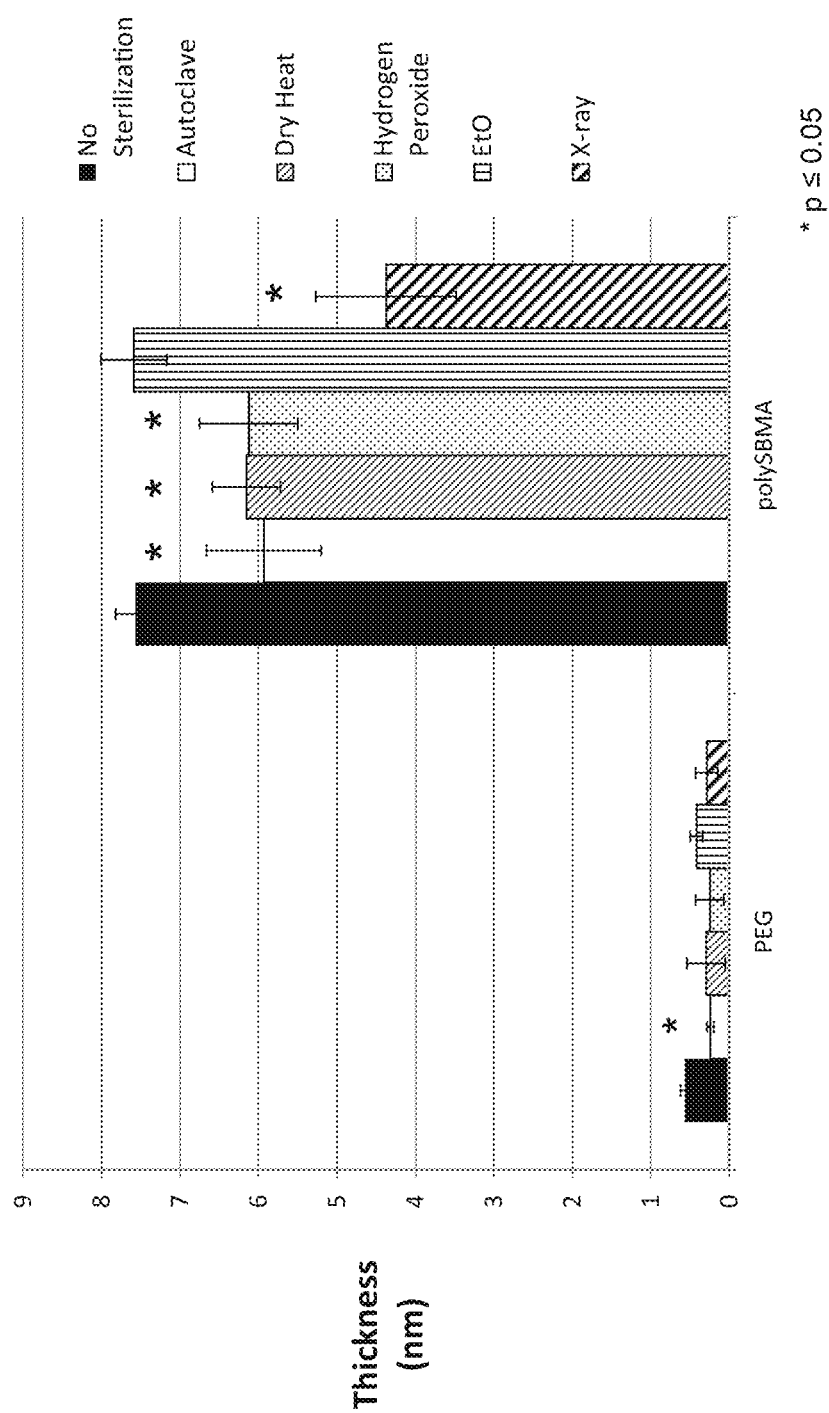
FIG. 33 is a graph showing ellipsometry results of sterilized coated silicon substrates, according to embodiments of the present disclosure.
Figure 34:
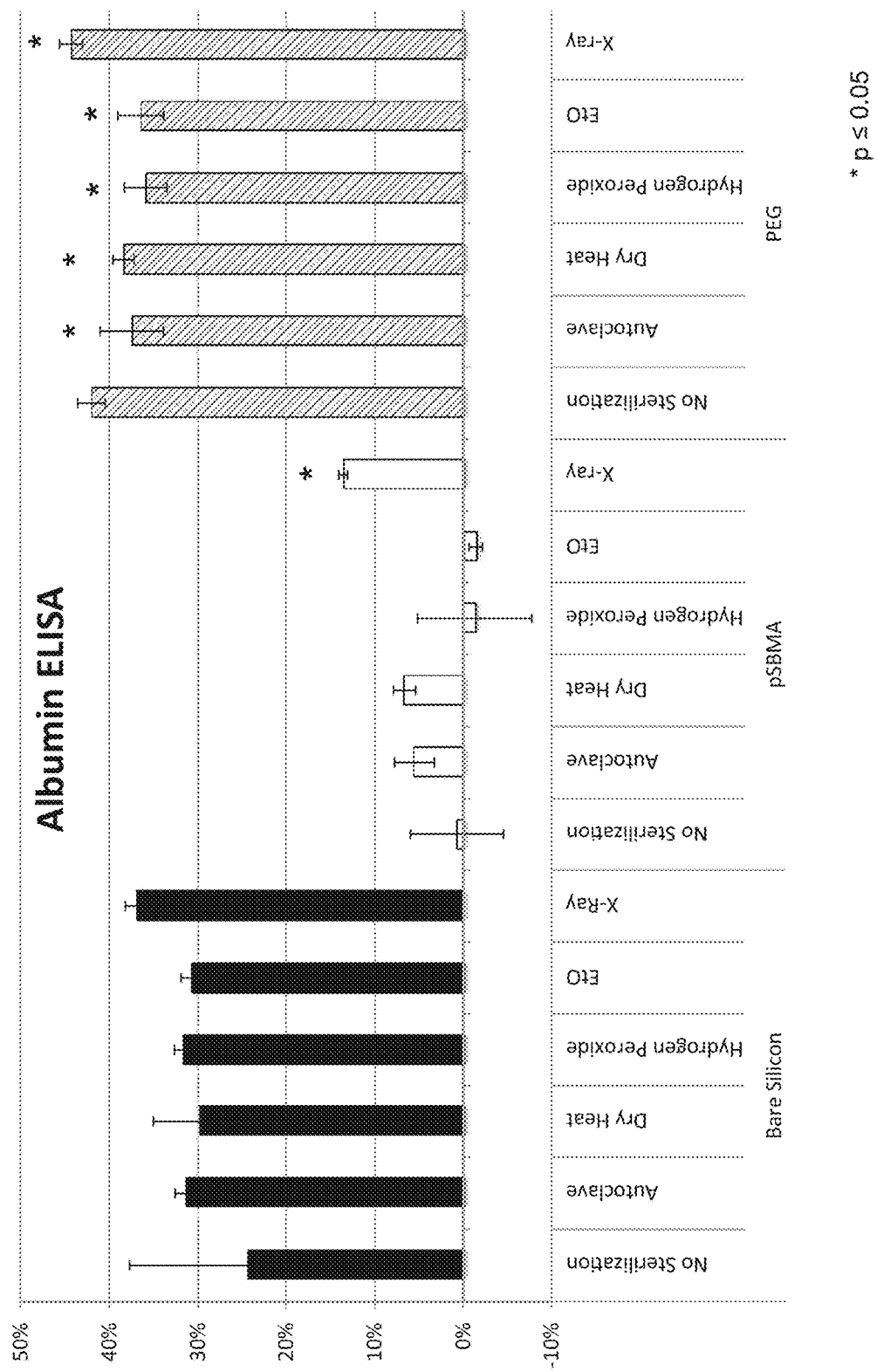
FIG. 34 is a graph showing protein adsorption of sterilized coated silicon substrates, according to embodiments of the present disclosure.

Autoclave was the only technique that caused a significant decrease in the thickness of the PEG layer ($\Delta$0.327 nm, p=0.0013) (FIG. 33). For pSBMA, each sterilization technique caused a significant decrease in thickness except EtO (FIG. 33). X-ray resulted in the largest decrease in pSBMA thickness ($\Delta$3.192 nm, p=0.019) (FIG. 33). Moreover, compared to non-sterilized substrates, x-ray had the largest increase in albumin adsorption, particularly for pSBMA-coated silicon (+12.86%, p=0.0018), while the other modalities each decreased adsorption (FIG. 34).

For untreated silicon, contact angle decreased after each sterilization. Sterilization did not significantly change protein adsorption.

While the present disclosure has been described with reference to the specific embodiments thereof, it should be understood by those skilled in the art that various changes may be made and equivalents may be substituted without departing from the true spirit and scope of the present disclosure. In addition, many modifications may be made to adapt a particular situation, material, composition of matter, process, process step or steps, to the objective, spirit and scope of the present disclosure. All such modifications are intended to be within the scope of the claims appended hereto.

What is claimed is:

1. A stackable plate subunit of a parallel plate device, the stackable plate subunit comprising:
a rectangular frame structure defined by a first strut opposite a second strut and a third strut opposite a fourth strut, wherein the first and second struts are perpendicular to the third and fourth struts,
the first strut and the second strut each comprising a slot that extends substantially along the entire length of each of the first and second struts,
each rectangular frame comprising a planar through channel bound by:
a first side of a first silicon nanoporous membrane,
a first side of a second silicon nanoporous membrane, and the third and fourth struts,
wherein the first silicon nanoporous membrane and the second silicon nanoporous membrane are positioned in the rectangular frame such that the membranes are substantially parallel to each other and in a spaced apart configuration and extend between the first and second struts and between third and fourth struts, wherein
the slot in the first strut forms an opening at a first end of the through channel, and
the slot in the second strut forms an opening at a second end of the through channel, and wherein a planar channel is latently formed along each of
a second side of the first silicon nanoporous membrane opposite the first side, and
a second side of the second silicon nanoporous membrane opposite the first side when the stackable plate subunit is stacked, thereby providing at least two latently formed planar channels,
wherein the second side of the first silicon nanoporous membrane and the second side of the second silicon nanoporous membrane are each recessed from a stacking surface of the frame on a corresponding side, to provide for a height of the latently formed planar channels.

2. The stackable plate subunit of claim 1, wherein the third strut and the fourth strut of the rectangular frame each comprise one or more through holes configured to provide fluidic communication between the planar channels.

3. The stackable plate subunit of claim 1, wherein the first strut and the second strut of the rectangular frame each comprise one or more through holes configured to provide fluidic communication between the planar channels and wherein the through holes pass through a pillar structure interposed in each of the first and second struts.

4. The stackable plate subunit of claim 2, wherein the through holes have a diameter in the range of about 0.1 mm to about 5.0 mm.

5. The stackable plate subunit of claim 1, wherein the stacking surface of the stackable frame comprises a groove configured to hold a gasket.

6. The stackable plate subunit of claim 1, wherein the slots are configured such that the through channel has substantially the same width from the first end to the second end.

7. The stackable plate subunit of claim 1, wherein the height of the slots is less than a distance between the first silicon nanoporous membrane and the second silicon nanoporous membrane.

8. The stackable plate subunit of claim 1, wherein the first silicon nanoporous membrane and the second silicon nanoporous membrane each comprises a plurality of effective membrane areas.

9. The stackable plate subunit of claim 8, wherein the effective membrane areas have a thickness from about 50 nm to about 1,000 nm.

10. The stackable plate subunit of claim 1, wherein the first silicon nanoporous membrane and the second silicon nanoporous membrane each have a thickness from about 10 µm to about 1,000 µm.

11. The stackable plate subunit of claim 1, wherein the first silicon nanoporous membrane and the second silicon nanoporous membrane each comprises nanoporous slits.

12. The stackable plate subunit of claim 11, wherein the nanoporous slits have a length of from about 1.0 µm to about 50 µm or wherein the nanoporous slits have a width of from about 1.0 nm to about 100 nm.

13. The stackable plate subunit of claim 1, wherein the planar through channel has a height of from about 0.5 mm to about 5.0 mm, or wherein the planar through channel has a length of from about 10 mm to about 100 mm, or wherein the planar through channel has a width of from about 10 mm to about 100 mm.

14. A parallel plate device for hemofiltration/hemodialysis, comprising:
a parallel plate assembly comprising:
an aligned stack of n stackable plate subunits of claim 1, wherein n is an integer of 2 or greater, wherein the opposite openings of the planar through channels define two ends of the parallel plate assembly; and
a cover plate capping each outer-most stackable plate subunit of the aligned stack,
wherein the parallel plate assembly comprises the latently formed planar channels on each side of n planar through channels; and
a blood conduit adaptor comprising a blood access port and attached to the parallel plate assembly at each of the two ends, wherein a lumen of the blood conduit adaptor is in fluid communication with each of the planar through channels.

15. The device of claim 14, wherein n is from 2 to 50.

16. The device of claim 14, wherein the latently formed planar channels have a height from about 0.1 mm to about 5.0 mm or wherein the latently formed planar channels have a width of from about 10 mm to about 100 mm.

17. The device of claim 14, wherein the latently formed planar channels have a length that is shorter than a length of the planar through channels by from about 1.0 mm to about 10 mm.

18. The device of claim 14 wherein the parallel plate assembly comprises a dialysate/filtrate plate subunit comprising one or more access ports proximal to each end of the parallel plate assembly, wherein the access ports are in fluidic communication with the latently formed planar channels.

19. The device of claim 14, wherein each cover plate comprises one or more access ports proximal to each end of the parallel plate assembly, wherein the access ports are in fluidic communication with the latently formed planar channels.

20. The device of claim 14, wherein each cover plate comprises polyether ether ketone (PEEK).

21. The device of claim 14, wherein each cover plate comprises a suture tab.

22. The device of claim 14, wherein the device comprises a spacer interposed between the blood conduit adaptor and each of the two ends of the parallel plate device.

23. A method of dialyzing blood, comprising
establishing a blood circuit comprising planar through channels of the parallel plate device of claim 18 with a circulatory system of an individual; and
establishing a dialysate circuit comprising:
the latently formed planar channels of the parallel plate device; and
a dialysate pump.

24. The stackable plate subunit of claim 3, wherein the through holes have a diameter in the range of about 0.1 mm to about 5.0 mm.

25. The stackable plate subunit of claim 2, the third and fourth struts each comprise a recessed area around each of the through holes.

26. The stackable plate subunit of claim 3, the first and second struts each comprise a recessed area around each of the through holes.

* * * * *

UNITED STATES PATENT AND TRADEMARK OFFICE
CERTIFICATE OF CORRECTION

PATENT NO.           : 11,185,824 B2                                Page 1 of 1
APPLICATION NO.      : 16/098708
DATED                : November 30, 2021
INVENTOR(S)          : Shuvo Roy It is certified that error appears in the above-identified patent and that said Letters Patent is hereby corrected as shown below:

On the Title Page

Column 1, please add --(73) Assignee: The Regents of the University of California, Oakland, CA (US)--.

<div style="text-align: right;">

Signed and Sealed this
Fourth Day of January, 2022

Drew Hirshfeld
*Performing the Functions and Duties of the
Under Secretary of Commerce for Intellectual Property and
Director of the United States Patent and Trademark Office*

</div>